US010960020B2

(12) United States Patent
Aikawa et al.

(10) Patent No.: US 10,960,020 B2
(45) Date of Patent: Mar. 30, 2021

(54) MODULATION OF PCSK9 AND LDLR THROUGH DRP1 INHIBITION

(71) Applicant: THE BRIGHAM AND WOMEN'S HOSPITAL, INC., Boston, MA (US)

(72) Inventors: Elena Aikawa, Chestnut Hill, MA (US); Maximillian Rogers, Boston, MA (US); Masanori Aikawa, Chestnut Hill, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 7 days.

(21) Appl. No.: 16/333,460

(22) PCT Filed: Sep. 12, 2017

(86) PCT No.: PCT/US2017/051130
§ 371 (c)(1),
(2) Date: Mar. 14, 2019

(87) PCT Pub. No.: WO2018/052891
PCT Pub. Date: Mar. 22, 2018

(65) Prior Publication Data
US 2019/0209603 A1 Jul. 11, 2019

Related U.S. Application Data

(60) Provisional application No. 62/394,799, filed on Sep. 15, 2016.

(51) Int. Cl.
| | |
|---|---|
| *A61K 31/7105* | (2006.01) |
| *A61K 45/06* | (2006.01) |
| *A61K 31/7088* | (2006.01) |
| *A61P 3/06* | (2006.01) |
| *C12N 15/113* | (2010.01) |
| *C12N 15/115* | (2010.01) |
| *A61K 48/00* | (2006.01) |
| *A61K 31/47* | (2006.01) |
| *A61K 31/22* | (2006.01) |

(52) U.S. Cl.
CPC .......... *A61K 31/7105* (2013.01); *A61K 31/22* (2013.01); *A61K 31/47* (2013.01); *A61K 31/7088* (2013.01); *A61K 45/06* (2013.01); *A61K 48/00* (2013.01); *A61P 3/06* (2018.01); *C12N 15/115* (2013.01); *C12N 15/1137* (2013.01)

(58) Field of Classification Search
None
See application file for complete search history.

(56) References Cited

U.S. PATENT DOCUMENTS

2008/0306015 A1  12/2008  Khvorova et al.
2015/0017262 A1   1/2015  Qian et al.

OTHER PUBLICATIONS

Devay et al., "Characterization of Proprotein Convertase Subtilisin/Kexin Type 9 (PCSK9) Trafficking Reveals a Novel Lysosomal Targeting Mechanism via Amyloid Precursor-like Protein 2 (APLP2)", The Journal of Biological Chemistry 288:15 10805-10818 (2013).
Girard et al., "The Dynamin Chemical Inhibitor Dynasore Impairs Cholesterol Trafficking and Sterol-Sensitive Genes Transcription in Human HeLa Cells and Macrophages" PLoS One 6:12 1-13 (2011).
Guo et al., "Potential Neurogenesis of Human Adipose-Derived Stem Cells on Electrospun Catalpol-Loaded Composite Nanofibrous Scaffolds", Annals of Biomedical Engineering 43:10 2597-2608 (2015).
Macia et al., "Dynasore, a Cell-Permeable Inhibitor of Dynamin" Developmental Cell 10:6 839-850 (2006).
Tavori et al., "Alirocumab: PCSK9 inhibitor for LDL cholesterol reduction" Expert Review of Cardiovascular Therapy 12:10 1137-1144 (2014).
Xu, et al., "Mitochondrial fusion/tission process involved in the improvement of catalpol on high-glucose-induced hepatic mitochondrial dysfunction" Acta Biochimica 47:9 730-740 (2015).

*Primary Examiner* — Tracy Vivlemore
(74) *Attorney, Agent, or Firm* — Nixon Peabody LLP

(57) ABSTRACT

Provided herein are methods for reducing levels of blood cholesterol, low-density lipoprotein (LDL), and/or the treatment of diseases associated with high cholesterol, hyperlipidemia, dyslipidemia, or high levels of low-density lipoprotein (LDL), wherein the methods comprise administering a DRP1 inhibitor to a subject in need thereof. In certain embodiments, the subject is selected for treatment as described herein when the subject exhibits intolerance to conventional statin therapy. Also contemplated herein are the use of DRP1 inhibitors in the treatment of cancer and inflammatory disease.

14 Claims, 39 Drawing Sheets
Specification includes a Sequence Listing.

α-TUBULIN Phalloidin DAPI

MODULATION OF PCSK9 AND LDLR THROUGH DRP1 INHIBITION

CROSS-REFERENCE TO RELATED APPLICATIONS

This Application is a 35 U.S.C. § 371 National Phase Entry Application of International Application No. PCT/US2017/051130 filed Sep. 12, 2017, which designates the U.S. and which claims benefit under 35 U.S.C. § 119(e) of the U.S. Provisional Application No. 62/394,799, filed Sep. 15, 2016, the contents of each of which are incorporated herein by reference in their entirety.

SEQUENCE LISTING

The instant application contains a Sequence Listing which as been submitted electronically in ASCII format and is hereby incorporated by reference in its entirety. Said ASCII copy, created on Sep. 28, 2017, is named 043214-087441-PCT_SL.txt and is 2,208 bytes in size.

FIELD OF THE DISCLOSURE

The present disclosure relates to the treatment of diseases and/or disorders comprising high cholesterol, hyperlipidemia, or high levels of low-density lipoprotein (LDL).

BACKGROUND

Atherosclerotic coronary heart disease (CHD) is a major cause for death and cardiovascular morbidity in the western world. Risk factors for atherosclerotic coronary heart disease include, but are not limited to, hypertension, diabetes mellitus, family history, male gender, cigarette smoke, high serum cholesterol, high low density lipoprotein (LDL) cholesterol levels and low high density lipoprotein (HDL) cholesterol levels. Clinical studies have shown that elevated levels of total cholesterol or LDL cholesterol can play a role in the pathogenesis of human atherosclerosis, thus lipid lowering agents are an important therapy for the treatment and/or prevention of atherosclerosis.

LDL cholesterol levels can be lowered by administration of HMG-CoA reductase inhibitors. This class of drugs inhibits the enzyme HMG-CoA reductase, which is rate-limiting in cholesterol synthesis by the liver. In addition, these agents increase the number of hepatic LDL receptors on the cell-surface to enhance uptake and catabolism of LDL. One potential drawback of HMG-CoA reductase inhibitors is the side-effect profile, including, e.g., liver toxicity.

PCSK9 (proprotein convertase subtilisin/kexin type 9) is a serine protease family member that binds to and regulates LDL receptor expression on the surface of cells. Inhibition of the LDL receptor-PCSK9 interaction is an attractive alternative approach to the treatment of cholesterol disorders. While substantial effort has been made to find agents that target PCSK9, small molecule PCSK9 inhibitor development has, so far, been unsuccessful.

SUMMARY

The present invention was discovered, in part, by the observation that inhibition of dynamin-related protein 1 (DRP1) causes a significant reduction in the amount of PCSK9 protein secreted from cells and further causes an increase in expression of a low-density lipoprotein receptor (LDLR). Accordingly, provided herein are methods for reducing levels of blood cholesterol, low-density lipoprotein (LDL), and/or the treatment of diseases associated with high cholesterol, hyperlipidemia, dyslipidemia, or high levels of low-density lipoprotein (LDL), wherein the methods comprise administering a DRP1 inhibitor to a subject in need thereof. In certain embodiments, the subject is selected for treatment as described herein when the subject exhibits intolerance to conventional statin therapy.

Further, inhibition of DRP1 is contemplated for the treatment of inflammatory disorders and/or cancer.

Accordingly, one aspect described herein relates to a method for reducing blood cholesterol levels, the method comprising administering an effective amount of an inhibitor of dynamin-related protein 1 (DRP1) or administering an effective amount of a composition comprising an inhibitor of DRP1 to a human or non-human subject in need thereof.

In one embodiment of this aspect and all other aspects provided herein, the subject exhibits intolerance to conventional statin treatment.

In another embodiment of this aspect and all other aspects provided herein, the DRP1 inhibitor is added as an adjunct treatment to an existing therapeutic protocol (e.g., conventional statin therapy).

In another embodiment of this aspect and all other aspects provided herein, the inhibitor of DRP1 inhibits DRP1 expression.

In another embodiment of this aspect and all other aspects provided herein, the inhibitor of DRP1 expression is selected from a small molecule and a nucleic acid.

In another embodiment of this aspect and all other aspects provided herein, the small molecule is an organic or inorganic compound having a molecular weight of less than about 10,000 grams per ole or a salt or ester or other pharmaceutically acceptable form of the compound, a peptide, a peptidomimetic, an amino acid, an amino acid analog, a nucleic acid, a nucleotide, or a nucleotide analog. In another embodiment of this aspect and all other aspects provided herein, the small molecule is a heterorganic compound or an organometallic compound.

In another embodiment of this aspect and all other aspects provided herein, the small molecule inhibitor is Mdivi-1 (also known in the art as 3-(2,4-Dichloro-5-methoxyphenyl)-2,3-dihydro-2-thioxo-4(1H)-quinazolinone, 3-(2,4-Dichloro-5-methoxyphenyl)-2-sulfanyl-4(3H)-quinazolinone). Mdivi-1 has the chemical structure of Formula I:

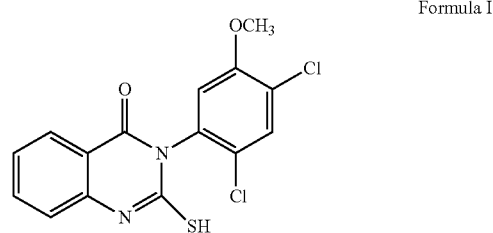

Formula I

In another embodiment of this aspect and all other aspects provided herein, the nucleic acid is a DRP1-specific RNA interference agent, or a vector encoding a DRP1-specific RNA interference agent.

In another embodiment of this aspect and all other aspects provided herein, the RNA interference agent comprises an siRNA, an miRNA, an shRNA, etc.

In another embodiment of this aspect and all other aspects provided herein, the siRNA comprises a sequence selected from the group consisting of: 5'-GGAGGCGCTAATTC-CTGTCAT-3' (SEQ ID NO. 1), 5'-GCAACTGGTCCAT-GTTTCACA-3' (SEQ ID NO. 2), 5'-GCTGCTCA-GTATCAGTCTCTT-3' (SEQ ID NO. 3), and 5'-GAA-TCTGCTCATGTGGAGACT-3' (SEQ ID NO. 4).

In another embodiment of this aspect and all other aspects provided herein, the DRP1-specific RNA interference agent is targeted for delivery to the liver.

In another embodiment of this aspect and all other aspects provided herein, the inhibitor of DRP1 inhibits DRP1 activity.

In another embodiment of this aspect and all other aspects provided herein, the inhibitor of DRP1 activity is selected from the group consisting of an antibody against DRP1 or an antigen-binding fragment thereof, a small molecule, and a nucleic acid.

In another embodiment of this aspect and all other aspects provided herein, the small molecule is an organic or inorganic compound having a molecular weight of less than about 10,000 grams per ole or a salt or ester or other pharmaceutically acceptable form of the compound, a peptide, a peptidomimetic, an amino acid, an amino acid analog, a nucleic acid, a nucleotide, or a nucleotide analog. In another embodiment of this aspect and all other aspects provided herein, the small molecule is a heterorganic compound or an organometallic compound.

In another embodiment of this aspect and all other aspects provided herein, the small molecule inhibitor is Mdivi-1 (also known in the art as 3-(2,4-Dichloro-5-methoxyphenyl)-2,3-dihydro-2-thioxo-4(1H)-quinazolinone, 3-(2,4-Dichloro-5-methoxyphenyl)-2-sulfanyl-4(3H)-quinazolinone) Mdivi-1 has the chemical structure of Formula I:

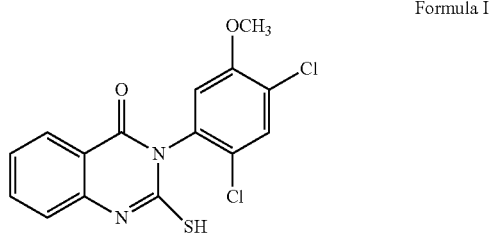 [SMILES: COc1cc(-n2c(S)nc3ccccc3c2=O)c(Cl)cc1Cl]

Formula I

In another embodiment of this aspect and all other aspects provided herein, the nucleic acid is a DRP1-specific RNA interference agent, a vector encoding a RNA interference agent, or an aptamer that binds DRP1.

In another embodiment of this aspect and all other aspects provided herein the siRNA comprises a sequence selected from the group consisting of: 5'-GGAGGCGCTAAT-TCCTGTCAT-3' (SEQ ID NO. 1), 5'-GCAACTGGTC-CATGTTTCACA-3' (SEQ ID NO. 2), 5'-GCTGC-TCAGTATCAGTCTCTT-3' (SEQ ID NO. 3), and 5'-GAATCTGCTCATGTGGAGACT-3' (SEQ ID NO. 4).

In another embodiment of this aspect and all other aspects provided herein, the DRP1 inhibitor is administered with a pharmaceutically acceptable carrier.

In another embodiment of this aspect and all other aspects provided herein, the DRP1 inhibitor is administered with at least one additional cholesterol lowering agent.

In another embodiment of this aspect and all other aspects provided herein, the at least one additional cholesterol lowering agent is selected from the group consisting of: statin, 7-alpha hydroxylase, liver X receptor agonist, bile acid binding resins, cholesterol absorption inhibitors, fibrates, niacin, omega-3 fatty acids, and pterostilbene.

In another embodiment of this aspect and all other aspects provided herein, the DRP1 inhibitor causes a reduction of low density lipoprotein in the subject.

In another embodiment of this aspect and all other aspects provided herein, the DRP1 inhibitor causes a reduction of serum proprotein convertase subtilisin/kexin type 9 (PCSK9) in the subject.

In another embodiment of this aspect and all other aspects provided herein, the DRP1 inhibitor causes a reduction of PCSK9 mRNA in cells of the subject.

In another embodiment of this aspect and all other aspects provided herein, the DRP1 inhibitor causes an increase in low density lipoprotein receptor (LDLR) expression on the cell (e.g., liver cell, human liver cell etc.).

In another embodiment of this aspect and all other aspects provided herein, the subject has a high level of cholesterol or a high level of low density lipoprotein.

Another aspect provided herein relates to a pharmaceutical composition comprising an effective amount of an inhibitor of dynamin-related protein 1 (DRP1), and a pharmaceutically acceptable carrier.

Also provided herein, in another aspect, is a method for reducing the secretion and expression of proprotein convertase subtilisin/kexin type 9 (PCSK9) in a cell, the method comprising: contacting the cell with an effective amount of a composition comprising an inhibitor of dynamin-related protein 1 (DRP1) or a an effective amount of a composition comprising an inhibitor of DRP1, whereby the level of PCSK9 expression and/or secretion is decreased in the cell relative to the level of PCSK9 expression and/or secretion in the cell prior to contacting with the DRP1 inhibitor.

In another embodiment of this aspect and all other aspects provided herein, the DRP1 inhibitor causes an increase in low density lipoprotein receptor (LDLR) expression on the cell (e.g., liver cell, human liver cell etc.).

Another aspect provided herein relates to a method for decreasing proprotein convertase subtilisin/kexin type 9 (PCSK9) serum levels in a mammal in need thereof, the method comprising the step of contacting a cell in the mammal with an effective amount of a composition comprising an inhibitor of dynamin-related protein 1 (DRP1) or a an effective amount of a composition comprising an inhibitor of DRP1, whereby the level of PCSK9 expression and/or secretion is decreased in said mammal, relative to the level of PCSK9 expression and/or secretion prior to said contacting.

Another aspect provided herein relates to a method for increasing low density lipoprotein receptor (LDLR) expression on the surface of a cell in a mammal in need thereof, the method comprising the step of contacting a cell in the mammal with an effective amount of a composition comprising an inhibitor of dynamin-related protein 1 (DRP1) or a an effective amount of a composition comprising an inhibitor of DRP1, whereby the level of LDLR expression on the cell is increased in said mammal, relative to the level of LDLR expression prior to said contacting.

In one embodiment, the cell is a liver cell (e.g., a human liver cell or hepatocyte).

Also provided herein, in another aspect, is a dynamin-related protein 1 (DRP1) inhibitor for use in the treatment of elevated cholesterol in a subject.

A further aspect provided herein relates to a dynamin-related protein 1 (DRP1) inhibitor for use in the manufacture of a medicament for the treatment of elevated cholesterol in a subject.

Another aspect provided herein relates to the use of a dynamin-related protein 1 (DRP1) inhibitor for the treatment of elevated cholesterol in a subject. Another aspect provided herein relates to the use of a dynamin-related protein 1 (DRP1) inhibitor in the manufacture of a medicament for the treatment of elevated cholesterol in a subject.

Also provided herein is a method for treating cancer or an inflammatory disease or disorder, the method comprising administering an effective amount of an inhibitor of dynamin-related protein 1 (DRP1) or administering an effective amount of a composition comprising an inhibitor of DRP1 to a human or non-human subject in need thereof, thereby treating the cancer of inflammatory disease/disorder in the subject.

Another aspect provided herein relates to the use of a dynamin-related protein 1 (DRP1) inhibitor in the manufacture of a medicament for the treatment of cancer in a subject.

Another aspect provided herein relates to the use of a dynamin-related protein (DRP1) inhibitor in the manufacture of a medicament for the treatment of an inflammatory disease or disorder.

Also provided herein is a dynamin-related protein 1 (DRP1) inhibitor for use in the treatment of cancer or an inflammatory disease/disorder in a subject.

Definitions

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic compositions described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques. In one embodiment, the "pharmaceutically acceptable" carrier does not include in vitro cell culture media.

In one embodiment, the term "pharmaceutically acceptable" refers to an ingredient approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration.

A "subject," as used herein, can include humans, laboratory animals (such as mouse, rat, rabbit, or guinea pig), farm animals, racing animals, and domestic animals or pets (such as a cat or dog), among others. Non-human primates and, preferably, human patients, are specifically contemplated for treatment as described herein.

As used herein, the terms "hyperlipidemia" or "dyslipidemia" refer to a condition(s) associated with abnormally elevated levels of lipids, such as low-density lipoprotein (LDL), free cholesterol, cholesterol esters, phospholipids and triglycerides, in blood. Although hyperlipidemia does not show specific symptoms by itself, excessive lipids in blood adhere to the blood vessel walls to reduce the blood vessel size and cause atherosclerosis by inflammatory reactions. For this reason, coronary heart disease, cerebrovascular disease, obstruction of peripheral blood vessels, etc., can occur in subjects having hyperlipidemia. Thus, the DRP1 inhibitors described herein can be used for the treatment of not only hyperlipidemia, fatty liver disease or atherosclerosis, but also coronary heart disease, cerebrovascular disease, or obstruction of peripheral blood vessels.

In one embodiment, as used herein "treatment" or "treating," includes any beneficial or desirable effect on the symptoms or pathology of a disease or pathological condition, and may include even minimal reductions in one or more measurable markers of the disease or condition being treated. In another embodiment, treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

In one embodiment, as used herein, "prevent," and similar words such as "prevented," "preventing" etc., indicate an approach for preventing, inhibiting, or reducing the likelihood of the occurrence or recurrence of, a disease or condition. In another embodiment, the term refers to delaying the onset or recurrence of a disease or condition or delaying the occurrence or recurrence of the symptoms of a disease or condition. In another embodiment, as used herein, "prevention" and similar words includes reducing the intensity, effect, symptoms and/or burden of a disease or condition prior to onset or recurrence of the disease or condition.

A "therapeutically effective amount" of an agent may vary according to factors such as the disease state, age, sex, and weight of the individual, and the potency of the agent to elicit a desired response in the individual (e.g., reduce serum LDL levels by at least 10%). A therapeutically effective amount is also one in which any toxic or detrimental effects of the DRP1 inhibitor are outweighed by the therapeutically beneficial effects. The term "therapeutically effective amount" includes an amount that is effective to "treat" a subject (e.g., a patient).

As used herein, a "humanized" antibody refers to forms of non-human (e.g., murine) antibodies that are chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. Preferably, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in WO 99/58572. Other forms of humanized antibodies have one or more CDRs (CDR L1, CDR L2, CDR L3, CDR H1, CDR H2, and/or CDR H3) which are altered with respect to the original antibody, which are also termed one or more CDRs "derived from" one or more CDRs from the original antibody.

The phrase "combination therapy" embraces the administration of a DRP1 inhibitor in combination with administration of a second agent (e.g., a statin) as part of a specific treatment regimen intended to provide a beneficial effect from the co-action of these therapeutic agents. "Combination therapy" generally is not intended to encompass the administration of two or more of these therapeutic agents as part of separate monotherapy regimens that incidentally and arbitrarily result in the combinations of the present invention. "Combination therapy" is intended to embrace administration of these therapeutic agents in a substantially simultaneous or sequential manner, that is, wherein each therapeutic agent is administered at the same or a different time. Substantially simultaneous administration can be accomplished, for example, by administering to the subject a single composition having a fixed ratio of each therapeutic agent or in multiple, single compositions for each of the therapeutic agents. Sequential or substantially simultaneous administration of each therapeutic agent can be effected by any appropriate route including, but not limited to, intrahepatic routes, intravenous routes, and parenteral routes. The therapeutic agents can be administered by the same route or by different routes. For example, a first therapeutic agent of the combination selected can be administered by intravenous injection while the other therapeutic agents of the combination can be administered by intra-hepatic injection. Alternatively, for example, all therapeutic agents can be administered by direct injection into the liver or all therapeutic agents may be administered by intravenous injection. In some embodiments, the sequence in which the therapeutic agents are administered is not narrowly critical. "Combination therapy" can also embrace the administration of DRP1 inhibitors in further combination with other biologically active ingredients (such as, but not limited to, a second and different agent for treatment hyperlipidemia or cardiovascular disease) and non-drug therapies (such as, but not limited to, surgery and lifestyle interventions). Combination agents can include drugs that are used to reduce or eliminate risk factors of e.g., cardiovascular disease, for example, reduce hypercholesterolemia by co-treatment with a statin agent, or reduce diabetic symptoms by administration of metformin.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention.

BRIEF DESCRIPTION OF THE DRAWINGS

(FIG. 1A) Volcano plot statistical analysis of HepG2 secreted protein changes 24 hours after Mdivi-1 treatment (50 µmol/L), identified by SILAC mass spectrometry. (FIG. 1B) Secreted PCSK9 ELISA using HepG2 media collected 24 hours after adding vehicle (0.01% DMSO), Mdivi-1 (50 µmol/L), pitavastatin (1 µmol/L), T0901317 (1 µmol/L), chloroquine (50 µmol/L), MG132 (0.3 µmol/L); and (FIG. 1C) HepG2 cellular PCSK9 protein. (FIG. 1D) HepG2 CRISPR/Cas9 DRP1 western blot and secreted PCSK9 ELISA. (FIG. 1E) Secreted PCSK9 ELISA and PCSK9 and LDLR mRNA from primary human hepatocytes treated for 24 hours; and (FIG. 1F) primary human hepatocyte cellular PCSK9 protein. n=pooled data from at least three experiments or donors. Error bars, STDEV; ns=not significant, * P<0.05, <0.01, *<0.001, ****<0.0001.

(FIG. 2A) HepG2 SREBP-2, SREBP-1a, SREBP-1c, HNF1a mRNA following 24-hour treatment with vehicle (0.01% DMSO) or Mdivi-1 (50 µmol/L). (FIG. 2B) HepG2 LDLR protein and mRNA following 24-hour treatment with vehicle, Mdivi-1, pitavastatin (1 µmol/L), and/or T0901317 (1 µmol/L); and (FIG. 2C) HepG2 HMGCR protein. (FIG. 2D) JUN mRNA and representative c-Jun western blots from HepG2 and primary human hepatocytes. n=pooled data from at least 3 experiments or donors. Error bars, STDEV; ns=not significant, * P<0.05, <0.01, *<0.001, ****<0.0001.

(FIG. 3A) Cytoskeleton-related mRNA panel showing no significant differences from HepG2 and primary human hepatocytes treated for 24 hours with vehicle (0.01% DMSO) or Mdivi-1 (50 µmol/L). (FIG. 3B) Representative HepG2 α-TUBULIN and phalloidin confocal immunofluorescence after 24-hour Mdivi-1 treatment; Bar, 10 µm. (FIG. 3C) HepG2 CRISPR/Cas9 electron microscopy representative ER morphology images; Bar, 500 nm. (FIG. 3D) DRP1 immunogold labeling representative HepG2 electron microscopy images; arrows indicate examples of DRP1 at ER exit sites, and arrow heads examples of DRP1 at cytosolic vesicles; Bar, 100 nm. Error bars, STDEV; n=3 experiments or donors.

(FIG. 4A) p (S349) p62, p62, LC3, BECLIN1, and BCL-XL western blots from HepG2 treated for 24 hours with vehicle (0.01% DMSO), Mdivi-1 (50 µmol/L), chloroquine (50 µmol/L), and/or MG132 (0.3 µmol/L). (FIG. 4B) LC3 and p62 confocal immunofluorescence 24 hours after adding vehicle, Mdivi-1, chloroquine, and/or MG132. White arrows indicate examples of perinuclear p62 aggregates. (FIG. 4C) Lysosomal-associated membrane protein 1 (LAMP1) and p62 confocal immunofluorescence 24 hours after adding MG132 with Mdivi-1. White arrow heads indicate examples of p62/LAMP1-positive perinuclear aggregates. Error bars, STDEV; ns=not significant, * P<0.05, <0.01, *<0.001, ****<0.0001; n=3 experiments.

(FIG. 5A) Weight, serum concentrations, and (FIG. 5B) plasma lipoprotein profiles from 1-month-old non-fasted chow fed male mice. (FIG. 5C) Liver LDLR, PCSK9, HMGCR protein and mRNA. n=5 mice/group. Error bars, STDEV; ns=not significant, * P<0.05, **<0.01.

(FIG. 6A) Liver SREBP2, (FIG. 6B) SREBP1, and (FIG. 6C) HNF1α protein and mRNA from 1-month-old non-fasted chow fed male mice. n=5 mice/group. Error bars, SEM. ns=not significant. n=5 mice/group. Error bars, STDEV; ns=not significant.

(FIG. 7A) Liver p62 and LC3 protein from 1-month-old non-fasted chow fed male mice. n=5 mice/group. Error bars, STDEV; ns=not significant, *** P<0.001. (FIG. 7B) Proposed working model: Mdivi-1 may inhibit PCSK9 in HepG2 partially via reduction of SREBP-1c-mediated transcriptional regulation. DRP1 inhibition may reduce PCSK9 secretion more broadly in human liver cells and mice via regulation of proteostasis involving impaired autophagic flux leading to PCSK9 ER retention and degradation via the proteasome.

(FIG. 8A) Anti-human PCSK9 antibody (antibody 1; R&D systems) human PCSK9 detection confirmation using HEK293 cells with native human PCSK9 overexpression, HeLa cells with CRISPR/Cas9-mediated PCSK9 knockout (KO), and liver lysate from mice with murine PCSK9 overexpression via adeno-associated virus (AAV)-mediated overexpression. (FIG. 8B) Anti-mouse/rat PCSK9 antibody (antibody 2; R&D systems) human and mouse PCSK9 detection confirmation, and LDLR antibody (BioVision Inc.) confirmation using C57BL/6 and LDLR-deficient (Ldlr−/−) liver lysate western blots.

(FIG. 9A) HepG2 total and phosphorylated (S637, S616) DRP1 protein following 24-hour treatment with vehicle (0.01% DMSO), Mdivi-1 (50 µmol/L), pitavastatin (1 µmol/L), and/or T0901317 (1 µmol/L). (FIG. 9B) HepG2 viability after 24-hour Mdivi-1 treatment. (FIG. 9C) Primary human hepatocytes DRP1, apolipoprotein E (APOE), ABC binding cassette transporter 1 (ABCA1), and (FIG. 9D) SREBP-2, SREBP-1a, SREBP-1c, and HNF1A mRNA. Error bars, STDEV. ns=not significant, * P<0.05, <0.01, *<0.001, ****<0.0001; n=at least 3 experiments or donors.

(FIG. 10A) Mitochondria (anti-mitochondria antibody) and protein disulfide-isomerase (PDI; ER marker) confocal immunofluorescence, and (FIG. 10B) mitochondrial membrane potential in HepG2 treated with vehicle (0.01% DMSO) or Mdivi-1 (50 µmol/L) for 24 hours.

(FIG. 11A) HepG2 and primary human hepatocytes BECLIN1 and BCL2 mRNA. (FIG. 11B) Representative western blot showing BCL2 protein was below detection in the experimental conditions used: HepG2 treated for 24 hours with vehicle (0.01% DMSO), Mdivi-1 (50 µmol/L), chloroquine (50 µmol/L), and/or MG132 (0.3 µmol/L). THP1 (human monocytic cell line) lysate was used as a BCL2 western blot positive control. (FIG. 11C) Human liver S9 fraction (containing cytosol and ER) DRP1 and BCL-XL western blot. (FIG. 11D) HepG2 BCL2L1 mRNA following 24-hour treatment. Error bars, STDEV. ns=not significant,  P<0.01, **<0.0001; n=3 experiments for HepG2, and pooled lysate from 50 donors for human liver S9 fraction analysis.

DETAILED DESCRIPTION

Figure 1A:
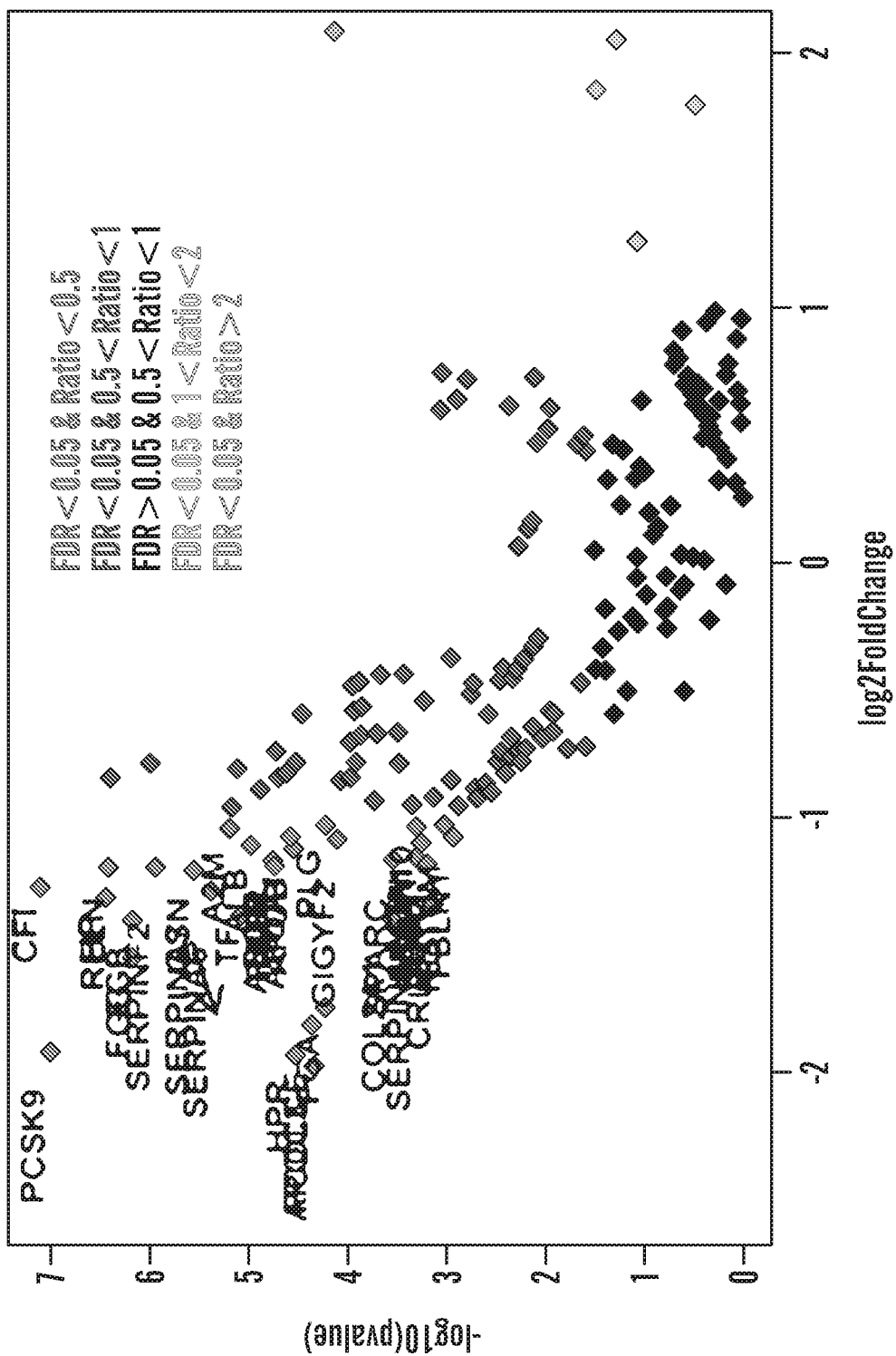
FIGS. 1A-1F DRP1 inhibition reduces PCSK9 secretion in human liver cells.

Provided herein are methods and compositions for reducing blood cholesterol levels, the method comprising administering an effective amount of an inhibitor of dynamin-related protein 1 (DRP1) or administering an effective amount of a composition comprising an inhibitor of DRP1 to a human or non-human subject in need thereof. The present invention relates to the treatment of diseases and/or disorders comprising high LDL cholesterol by administering an inhibitor of DRP1. In some embodiments, the methods and compositions described herein are useful for the treatment of subjects that exhibit intolerance to traditional statin therapy. The methods and compositions provided herein restore sensitivity of such subjects to statin therapy. Thus, it is further contemplated herein that inhibitors of DRP1 or compositions thereof can be used as an adjunct therapy to conventional statin therapy.

Hyperlipidemias/Dyslipidemias

Hyperlipidemia or dyslipidemia refers to a condition associated with elevated levels of lipids, such as free cholesterol, cholesterol esters, phospholipids and triglycerides, in blood. Hyperlipidemia can appear in three forms: (1) hypercholesterolemia, (2) hypertriglyceridemia, and (3) combined hyperlipidemia (hypercholesterolemia and hypertriglyceridemia). Hyperlipidemia is generally classified into primary hyperlipidemia and secondary hyperlipidemia. Primary hyperlipidemia is generally caused by genetic defects, whereas secondary hyperlipidemia is caused by various disease conditions, drugs and dietary habits. In addition, hyperlipidemia is also caused by a combination of the primary and secondary causes of hyperlipidemia. As criteria for the diagnosis of hyperlipidemia, a total cholesterol level of 220 mg/dl or higher and a triglyceride level of 150 mg/dl or higher are generally used.

There are various forms of cholesterol that naturally occur in mammals. Low-density (LDL) cholesterol is known to be harmful to health, and it is known that an increase in LDL cholesterol increases the risk of heart disease (Assman et al., Am. J. Card, 1996). In addition, high-density (HDL) cholesterol is regarded as good cholesterol and is essential for health, because it prevents atherosclerosis or the like. Reduction of LDL cholesterol is currently the primary goal of dyslipidemia management.

Although hyperlipidemia does not show specific symptoms by itself, excessive lipids in blood adhere to the blood vessel walls to reduce the blood vessel size and cause atherosclerosis by inflammatory reactions. For this reason, coronary heart disease, cerebrovascular disease, obstruction of peripheral blood vessels, etc., can occur (E. Falk et al., Circulation, 1995). In addition, excessive blood lipids are accumulated in liver tissue, and thus can cause fatty liver disease. The fatty liver refers to a condition in which the ratio of fats in the weight of the liver is more than 5%. The fatty liver can be caused not only by excessive intake of fats, but also by intake of alcohol.

Current methods that are used to reduce blood lipid levels include dietary therapy, exercise therapy and drug therapy. However, dietary therapy or excise therapy is difficult to strictly control and perform, and the therapeutic effect thereof is also limited.

Drugs for reducing lipid levels, particularly low-density lipoprotein, developed to date include bile acid binding resins, cholesterol-lowering drugs such as HMG-CoA reductase inhibitors important in cholesterol biosynthesis, triglyceride-lowering drugs such as fibric acid derivatives and nicotinic acid, etc. However, these drugs were reported to have side effects such as hepatic toxicity, gastrointestinal disorder and carcinogenesis. Thus, there is an urgent need for the development of drugs that can be used to treat hyperlipidemia and related diseases (e.g., atherosclerosis and fatty liver disease) while having less significant side effects.

The decision to start lipid-lowering treatment is typically made on a case-by-case basis. It is important to note that hyperlipidemia itself is asymptomatic and thus needs to be diagnosed with one or more laboratory tests, such as total cholesterol levels, low-density lipoprotein (LDL) levels, high-density lipoprotein (HDL) levels, ratios of LDL:HDL, etc. One of skill in the art can consider current lipid levels, the presence or absence of cardiovascular disease (CVD), and other risk factors for CVD to inform treatment. Guidelines provided by e.g., The American Heart Association can be used to guide treatment of individuals having hyperlipidemia based on their risk factors, current health status, etc. In particular, The American Heart Association recommends that subjects that fall into one or more of the following categories should be treated with a lipid lowering therapy, such as a statin. One of skill in the art will recognize that these subjects are at high risk of adverse effects associated with hyperlipidemia and as such, that treatment as described herein with a DRP1 inhibitor is likely to be beneficial.

---

Adults with LDL cholesterol of 70-189 mg/dL and a 7.5 percent or higher risk for having a heart attack or stroke within 10 years.
People with a history of a cardiovascular event (heart attack, stroke, stable or unstable angina, peripheral artery disease, transient ischemic attack, or coronary or other arterial revascularization).

People 21 and older who have a very high level of LDL cholesterol (190 mg/dL or higher).
People with diabetes and a LDL cholesterol level of 70-189 mg/dL who are 40 to 75 years old.

In one embodiment, a subject is selected for treatment with a DRP1 inhibitor following the diagnosis of elevated low-density lipoprotein in blood, or the diagnosis of a disease or disorder comprising elevated blood LDL.

In one embodiment, a subject is selected for treatment with a DRP1 inhibitor following intolerance to conventional statin therapy. In another embodiment, a subject is treated with combination therapy comprising DRP1 and a second lipid-lowering agent e.g., a statin.

Cancer

DRP1 inhibition is beneficial in the treatment of lung cancer in human cells and in animal models. Accordingly, provided herein is a method for treating cancer comprising the administration of a composition containing a DRP1 inhibitor. Essentially any cancer or cancer cell population or cancer cell can be treated according to the methods described herein. Exemplary cancers include, but are not limited to, bladder cancer; breast cancer; brain metastases; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS associated leukemias and adult T-cell leukemia lymphoma; intraepithelial neoplasms including Bowen's disease and Paget's disease, liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilm's tumor.

Inflammatory Disorders

Inhibition of PCSK9 has been suggested to have a pro-inflammatory function. Thus, it is contemplated herein that inhibition of PCSK9 through DRP1 inhibition can reduce inflammation, thereby treating inflammatory diseases or disorders. Essentially any immune disease or disorder can be treated using the methods and compositions described herein. The term "immune disease or disorder" is intended to encompass both acute and chronic inflammation.

In some embodiments, the term "immune disease or disorder" refers to diseases and conditions associated with inflammation which include but are not limited to: (1) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., myositis, inflammatory CNS disorders such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Bechet's syndrome).

In other embodiments, the term "immune disease or disorder" refers to a state of acute or chronic inflammation. An acute inflammatory response is an immediate response by the immune system to a harmful agent. The response includes vascular dilatation, endothelial and neutrophil activation. An acute inflammatory response will either resolve or develop into chronic inflammation.

Chronic inflammation is an inflammatory response of prolonged duration, weeks, months, or even indefinitely, whose extended time course is provoked by the persistence of the causative stimulus to inflammation within the tissue or the development of an autoimmune disorder. The inflammatory process inevitably causes tissue damage. The exact nature, extent and time course of chronic inflammation is variable, and depends on a balance between the causative agent and the attempts of the body to remove it. Agents producing chronic inflammation include, but are not limited to: infectious organisms that can avoid or resist host defenses and so persist in the tissue for a prolonged period; infectious organisms that are not innately resistant but persist in damaged regions where they are protected from host defenses; irritant non-living foreign material that cannot be removed by enzymatic breakdown or phagocytosis; or where the stimuli is a "normal" or "self" tissue component, causing an auto-immune disease. There is a vast array of diseases exhibiting a chronic inflammatory component. These include but are not limited to: inflammatory joint diseases (e.g., rheumatoid arthritis, osteoarthritis, polyarthritis and gout), chronic inflammatory connective tissue diseases (e.g., systemic lupus erythematosus, scleroderma, Sjorgen's syndrome, poly- and dermatomyositis, vasculitis, mixed connective tissue disease (MCTD), tendonitis, synovitis, bacterial endocarditis, osteomyelitis and psoriasis); chronic inflammatory lung diseases (e.g., chronic respiratory disease, pneumonia, fibrosing alveolitis, chronic bronchitis, bronchiectasis, emphysema, silicosis and other pneumoconiosis and tuberculosis); chronic inflammatory bowel and gastro-intestinal tract inflammatory diseases (e.g., ulcerative colitis and Crohn's disease); chronic neural inflammatory diseases (e.g., chronic inflammatory demyelinating polyradiculoneuropathy, chronic inflammatory demyelinating polyneuropathy, multiple sclerosis, Guillain-Barre Syndrome and myasthenia gravis); other inflammatory diseases (e.g., mastitis, laminitis, laryngitis, chronic cholecystitis, Hashimoto's thyroiditis, inflammatory breast disease); chronic inflammation caused by an implanted foreign body in a wound; and including chronic inflammatory renal diseases including crescentic glomerulonephritis, lupus nephritis, ANCA-associated glomerulonephritis, focal and segmental necrotizing glomerulonephritis, IgA nephropathy, membranoproliferative glomerulonephritis, cryoglobulinaemia and tubulointerstitial nephritis. Diabetic nephropathy may also have a chronic inflammatory component and chronic inflammatory responses are involved in the rejection of transplanted organs. Other non-limiting examples of diseases with symptoms of chronic inflammation include obesity, inflammatory bowel diseases such as Crohn's disease and ulcerative colitis, psoriasis, sarcoidosis, atherosclerosis including plaque rupture, Sjogrens disease, acne rosacea, syphilis, chemical burns, bacterial ulcers, fungal ulcers, Behcet's syndrome, Stevens-Johnson's disease, Mycobacteria infections, Herpes simplex infections, Herpes zoster infections, protozoan infections, Mooren's ulcer, leprosy, Wegener's sarcoidosis, pemphigoid, lupus, systemic lupus erythematosis, polyarteritis, Lyme's disease, Bartonelosis, tuberculosis, histoplasmosis and toxoplasmosis.

Essentially any disease or disorder characterized by, caused by, resulting from, or becoming affected by inflammation can be treated with the methods and compositions described herein. Other diseases or disorders contemplated for treatment with the methods described herein include, but are not limited to, acne, angina, arthritis, aspiration pneumonia, empyema, gastroenteritis, necrotizing enterocolitis, pelvic inflammatory disease, pharyngitis, pleurisy, chronic inflammatory demyelinating polyneuropathy, chronic inflammatory demyelinating polyradiculoneuropathy, and chronic inflammatory demyelinating polyneuropathy, among others.

PCSK9

PCSK9, also known as NARC-1, was first identified as a protein with a genetic mutation in some forms of familial hypercholesterolemia. PCSK9 is synthesized as a zymogen that undergoes autocatalytic processing at the motif LVFAQ in the endoplasmic reticulum. Population studies have shown that some PCSK9 mutations are "gain-of-function" and are found in individuals with autosomal dominant hypercholesterolemia, while other "loss-of-function" (LOF) mutations are linked with reduced plasma cholesterol. Morbidity and mortality studies in this group clearly demonstrated that reducing PCSK9 function significantly diminished the risk of cardiovascular disease.

Of significant importance to the treatment of cardiovascular disease, a loss of function mutation may sensitize humans to statins, allowing for efficacy at a lower dose (hence, improving risks associated with safety and tolerance) and potentially achieving lower plasma cholesterol levels than with current therapies.

PCSK9 is secreted into the plasma predominantly by hepatocytes. Genetic modulation of PCSK9 in mice confirmed the ability of PCSK9 to regulate blood lipids, and suggested that it acts to down-regulate hepatic LDLR protein levels.

Without wishing to be bound by theory, when overexpressed, PCSK9 may act both within the hepatocyte and as a secreted ligand for LDLR. There is strong evidence that extracellular PCSK9 binds to cell surface LDLR and promotes LDLR degradation at an intracellular site. However, it is also possible that PCSK9 could interact with the LDLR when the two proteins are translated within the endoplasmic reticulum (ER) and traffic through endosomal compartments towards the cell membrane.

With respect to therapeutic inhibition of PCSK9, antibodies directed against PCSK9 have been shown to be effective lipid lowering agents. However, the use of PCSK9 antibodies has certain drawbacks including that they are expensive to make, difficult to store, and require administration by injection, which can reduce patient compliance. However, targeting of PCSK9 activity by inhibiting the upstream protein DRP1 instead of using PCSK9 antibodies can result in far fewer clinical drawbacks.

In addition, PCSK9 has been shown to have a pro-inflammatory function, thus inhibition of PCSK9, for example using DRP1 inhibitors as described herein, is an important therapeutic strategy for the treatment of inflammatory disorders and/or autoimmune disease. Further, there is a growing understanding that improper and pro-inflammatory mediators play a role in cancer development and progression, thus inhibition of the DRP1/PCSK9 axis would be expected to mediate anti-cancer effects.

The study described herein in the working Examples indicates that inhibition of dynamin-related protein 1 (DRP1) reduces PCSK9 activity, in part by reducing the secretion of PCSK9 from hepatocytes. In addition, DRP1 inhibitors also cause an increase in LDLR expression on the surface of liver cells. Thus, DRP1 inhibitors are contemplated to inhibit DRP1, which in turn prevents PCSK9 secretion and reduces levels of low-density lipoprotein (LDL) in blood, for example, by increasing LDL uptake by enhanced LDLR expression.

DRP1 Inhibitors

DRP1 inhibitors can include, but are not limited to, antibody or antibody fragments, RNA interference agents, and small molecules. One of skill in the art can easily determine if a candidate agent comprises DRP1 inhibitory activity by measuring DRP1 activity in an in vitro assay, such as those described by e.g., Qi et al. (2013) *J. Cell Sci* 126:789-802 and Leonard et al. (2005) *Methods Enzymol* 404:490-503, among others. Provided herein below are DRP1 inhibitors specifically contemplated for treatment of hyperlipidemias and/or formulation as pharmaceutical compositions as described herein.

Antibodies to DRP1:

In one embodiment, a therapeutic antibody that binds to e.g., DRP1 is used herein in the treatment of an disease or disorder comprising hyperlipidemia (e.g., elevated low-density lipoprotein (LDL).

An "antibody" that can be used according to the methods described herein includes complete immunoglobulins, antigen binding fragments of immunoglobulins, as well as antigen binding proteins that comprise antigen binding domains of immunoglobulins. Antigen binding fragments of immunoglobulins include, for example, Fab, Fab', F(ab')2, scFv and dAbs. Modified antibody formats have been developed which retain binding specificity, but have other characteristics that may be desirable, including for example, bispecificity, multivalence (more than two binding sites), and compact size (e.g., binding domains alone). Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies. Multiple single chain antibodies, each single chain having one VH and one VL domain covalently linked by a first peptide linker, can be covalently linked by at least one or more peptide linker to form multivalent single chain antibodies, which can be monospecific or multispecific.

Each chain of a multivalent single chain antibody includes a variable light chain fragment and a variable heavy chain fragment, and is linked by a peptide linker to at least one other chain. The peptide linker is composed of at least fifteen amino acid residues. The maximum number of linker amino acid residues is approximately one hundred. Two single chain antibodies can be combined to form a diabody, also known as a bivalent dimer. Diabodies have two chains and two binding sites, and can be monospecific or bispecific. Each chain of the diabody includes a VH domain connected to a VL domain. The domains are connected with linkers that are short enough to prevent pairing between domains on the same chain, thus driving the pairing between complementary domains on different chains to recreate the two antigen-binding sites. Three single chain antibodies can be combined to form triabodies, also known as trivalent trimers. Triabodies are constructed with the amino acid terminus of a VL or VH domain directly fused to the carboxyl terminus of a VL or VH domain, i.e., without any linker sequence. The triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific. Thus, antibodies useful in the methods described herein include, but are not limited to, naturally occurring antibodies, bivalent fragments such as (Fab')2, monovalent fragments such as Fab, single chain antibodies, single chain Fv (scFv), single domain antibodies, multivalent single chain antibodies, diabodies, triabodies, and the like that bind specifically with an antigen (e.g., DRP1).

Antibodies can also be raised against a polypeptide or portion of a polypeptide by methods known to those skilled in the art. Antibodies are readily raised in animals such as rabbits or mice by immunization with the gene product, or a fragment thereof. Immunized mice are particularly useful for providing sources of B cells for the manufacture of hybridomas, which in turn are cultured to produce large quantities of monoclonal antibodies. Antibody manufacture methods are known in the art and are not described in detail herein. While both polyclonal and monoclonal antibodies can be used in the methods described herein, it is preferred that a monoclonal antibody is used where conditions require increased specificity for a particular protein.

Useful monoclonal antibodies and fragments can be derived from any species (including humans) or can be formed as chimeric proteins which employ sequences from more than one species. Human monoclonal antibodies or "humanized" murine antibodies are also used in accordance with the methods and assays described herein. For example, a murine monoclonal antibody can be "humanized" by genetically recombining the nucleotide sequence encoding the murine Fv region (i.e., containing the antigen binding sites) or the complementarity determining regions thereof with the nucleotide sequence encoding a human constant domain region and an Fc region. Humanized targeting moieties are recognized to decrease the immunoreactivity of the antibody or polypeptide in the host recipient, permitting an increase in the half-life and a reduction of the possibly of adverse immune reactions. The murine monoclonal antibodies should preferably be employed in humanized form. Antigen binding activity is determined by the sequences and conformation of the amino acids of the six complementarity determining regions (CDRs) that are located (three each) on the light and heavy chains of the variable portion (Fv) of the antibody. The 25-kDa single-chain Fv (scFv) molecule is composed of a variable region (VL) of the light chain and a variable region (VH) of the heavy chain joined via a short peptide spacer sequence. Techniques have been developed to display scFv molecules on the surface of filamentous phage that contain the gene for the scFv. scFv molecules with a broad range of antigenic-specificities can be present in a single large pool of scFv-phage library.

Chimeric antibodies are immunoglobin molecules characterized by two or more segments or portions derived from different animal species. Generally, the variable region of the chimeric antibody is derived from a non-human mammalian antibody, such as a murine monoclonal antibody, and the immunoglobulin constant region is derived from a human immunoglobulin molecule. In some embodiments, both regions and the combination have low immunogenicity as routinely determined.

Nucleic Acid Inhibitors of DRP1 Expression:

A powerful approach for inhibiting the expression of selected target polypeptides is through the use of RNA interference agents. RNA interference (RNAi) uses small interfering RNA (siRNA) duplexes that target the messenger RNA encoding the target polypeptide for selective degradation. siRNA-dependent post-transcriptional silencing of gene expression involves cleaving the target messenger RNA molecule at a site guided by the siRNA. "RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18): 9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease will be of at least 10%, 20%, 30%, 40%, 50%, 60%, 70%, 80%, 90%, 95% or 99% or more as compared to the expression of a target gene or the activity or level of the protein encoded by a target gene which has not been targeted by an RNA interfering agent.

The terms "RNA interference agent" and "RNA interference" as they are used herein are intended to encompass those forms of gene silencing mediated by double-stranded RNA, regardless of whether the RNA interfering agent comprises an siRNA, miRNA, shRNA or other double-stranded RNA molecule. "Short interfering RNA" (siRNA), also referred to herein as "small interfering RNA" is defined as an RNA agent which functions to inhibit expression of a target gene, e.g., by RNAi. An siRNA can be chemically synthesized, can be produced by in vitro transcription, or can be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and can contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety). The target gene or sequence of the RNA interfering agent can be a cellular gene or genomic sequence, e.g. the DRP1 sequence. An siRNA can be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target. The siRNA preferably targets only one sequence. Each of the RNA interfering agents, such as siRNAs, can be screened for potential off-target effects by, for example, expression profiling. Such methods are known to one skilled in the art and are described, for example, in Jackson et al. Nature Biotechnology 6:635-637, 2003. In addition to expression profiling, one can also screen the potential target sequences for similar sequences in the sequence databases to identify potential sequences which can have off-target effects. For example, according to Jackson et al. (Id.), 15, or perhaps as few as 11 contiguous nucleotides, of sequence identity are sufficient to direct silencing of non-targeted transcripts. Therefore, one can initially screen the proposed siRNAs to avoid potential off-target silencing using the sequence identity analysis by any known sequence comparison methods, such as BLAST. siRNA sequences are chosen to maximize the uptake of the antisense (guide) strand of the siRNA into RISC and thereby maximize the ability of RISC to target human GGT mRNA for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the mRNA. siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatizes with a variety of groups. Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases can also be modified. Any modified base useful for inhibiting or interfering with the expression of a target sequence can be used. For example, halogenated bases, such as 5-bromouracil and 5-iodouracil can be incorporated. The bases can also be alkylated, for example, 7-methylguanosine can be incorporated in place of a guanosine residue. Non-natural bases that yield successful inhibition can also be incorporated. The most preferred siRNA modifications include 2'-deoxy-2'-fluorouridine or locked nucleic acid (LAN) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

In a preferred embodiment, the RNA interference agent is delivered or administered in a pharmaceutically acceptable carrier. Additional carrier agents, such as liposomes, can be added to the pharmaceutically acceptable carrier. In another embodiment, the RNA interference agent is delivered by a vector encoding small hairpin RNA (shRNA) in a pharmaceutically acceptable carrier to the cells in an organ of an individual. The shRNA is converted by the cells after transcription into siRNA capable of targeting, for example, DRP1.

In one embodiment, the vector is a regulatable vector, such as a tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In one embodiment, the RNA interference agents used in the methods described herein are taken up actively by cells in vivo following intravenous injection, e.g., hydrodynamic injection, without the use of a vector, illustrating efficient in vivo delivery of the RNA interfering agents. One method to deliver the siRNAs is by topical administration in an appropriate pharmaceutically acceptable carrier. Other strategies for delivery of the RNA interference agents, e.g., the siRNAs or shRNAs used in the methods of the invention, can also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles. The RNA interference agents, e.g., the siRNAs targeting DRP1 mRNA, can be delivered singly, or in combination with other RNA interference agents, e.g., siRNAs, such as, for example siRNAs directed to other cellular genes. siRNAs can also be administered in combination with other pharmaceutical agents which are used to treat or prevent diseases or disorders comprising inflammation of the skin. Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) Nature 411:494-498; Elbashir, S. M., W. Lendeckel and T. Tuschl (2001) Genes & Development 15:188-200; Harborth, J. et al. (2001) J. Cell Science 114:4557-4565; Masters, J. R. et al. (2001) Proc. Natl. Acad. Sci., USA 98:8012-8017; and Tuschl, T. et al. (1999) Genes & Development 13:3191-3197). Alternatively, several commercial RNA synthesis suppliers are available including, but not limited to, Proligo™ (Hamburg, Germany), Dharmacon™ Research (Lafayette, Colo., USA), Pierce Chemical™ (part of Perbio Science™, Rockford, Ill., USA), Glen Research™ (Sterling, Va., USA), ChemGenes™ (Ashland, Mass., USA), and Cruachem™ (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al. (2002) Genes Dev. 16:948-958; McManus, M. T. et al. (2002) RNA 8:842-850; Paul, C. P. et al. (2002) Nat. Biotechnol. 20:505-508; Miyagishi, M. et al. (2002) Nat. Biotechnol. 20:497-500; Sui, G. et al. (2002) Proc. Natl. Acad. Sci., USA 99:5515-5520; Brummelkamp, T. et al. (2002) Cancer Cell 2:243; Lee, N. S., et al. (2002) Nat. Biotechnol. 20:500-505; Yu, J.Y., et al. (2002) Proc. Natl. Acad. Sci., USA 99:6047-6052; Zeng, Y., et al. (2002) Mol. Cell 9:1327-1333; Rubinson, D. A., et al. (2003) Nat. Genet. 33:401-406; Stewart, S. A., et al. (2003) RNA 9:493-501). These vectors generally have a polIII promoter upstream of the dsRNA and can express sense and antisense RNA strands separately and/or as a hairpin structure. Within cells, Dicer processes the short hairpin RNA (shRNA) into effective siRNA. The targeted region of the siRNA molecule of the present invention can be selected from a given target gene sequence, e.g., a DRP1 coding sequence, beginning from about 25 to 50 nucleotides, from about 50 to 75 nucleotides, or from about 75 to 100 nucleotides downstream of the start codon. Nucleotide sequences can contain 5' or 3' UTRs and regions nearby the start codon. One method of designing a siRNA molecule as described herein involves identifying the 23 nucleotide sequence motif AA(N19)TT (SEQ. ID. NO. 1) (where N can be any nucleotide) and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search can be extended using the motif NA(N21), where N can be any nucleotide. In this situation, the 3' end of the sense siRNA can be converted to TT to allow for the generation of a symmetric duplex with respect to the sequence composition of the sense and antisense 3' overhangs. The antisense siRNA molecule can then be synthesized as the complement to nucleotide positions 1 to 21 of the 23 nucleotide sequence motif. The use of symmetric 3' TT overhangs can be advantageous to ensure that the small interfering ribonucleoprotein particles (siRNPs) are formed with approximately equal ratios of sense and antisense target RNA-cleaving siRNPs (Elbashir et al., (2001) supra and Elbashir et al., 2001 supra). Analysis of sequence databases, including but not limited to the NCBI, BLAST, Derwent and GenSeq as well as commercially available oligosynthesis companies such as Oligoengine®, can also be used to select siRNA sequences against EST libraries to ensure that only one gene is targeted.

siRNA sequences to target DRP1 can also be obtained commercially from e.g., INVITROGEN, THERMO SCIENTIFIC, ORIGENE, among others. In another embodiment, the siRNA against DRP1 comprises a sequence selected from the group consisting of: 5'-GGAGGCGCTAAT-TCCTGTCAT-3' (SEQ ID NO. 1), 5'-GCAACTGGTC-CATGTTTCACA-3' (SEQ ID NO. 2), 5'-GCTG-CTCAGTATCAGTCTCTT-3' (SEQ ID NO. 3), and 5'-GAATCTGCTCATGTGGAGACT-3' (SEQ ID NO. 4).

Delivery of RNA Interfering Agents:

Methods of delivering RNA interference agents, e.g., an siRNA, or vectors containing an RNA interference agent, to the target cells, e.g., hepatocytes, or other desired target cells, for uptake include topical administration or injection of a composition containing the RNA interference agent, e.g., an siRNA, or directly contacting the cell, e.g., a hepatocyte, with a composition comprising an RNA interference agent, e.g., an siRNA. In another embodiment, RNA interference agent, e.g., an siRNA can be injected directly into any blood vessel, such as a vein, artery, venule or arteriole, via, e.g., hydrodynamic injection or catheterization. Administration can be by a single injection or by two or more injections. The RNA interference agent is delivered in a pharmaceutically acceptable carrier. One or more RNA interference agents can be used simultaneously. In one embodiment, a single siRNA that targets human DRP1 is used. In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNA interference effectively into cells. For example, an antibody-protamine fusion protein when mixed with siRNA, binds siRNA and selectively delivers the siRNA into cells expressing an antigen recognized by the antibody, resulting in silencing of gene expression only in those cells that express the antigen. In one example, the RNA interference molecule(s) are fused to a liver cell targeting moiety, however it should be noted that delivery to hepatocytes does not always require the use of a targeting moiety since the agents are subject to the first pass effect with certain modes of administration, and as such they enter the liver prior to other organs and are taken up by hepatocytes readily. The siRNA or RNA interference-inducing molecule binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein. A viral-mediated delivery mechanism can also be employed to deliver siRNAs to cells in vitro and in vivo as described in Xia, H. et al. (2002) Nat Biotechnol 20(10):1006). Plasmid- or viral-mediated delivery mechanisms of shRNA can also be employed to deliver shRNAs to cells in vitro and in vivo as described in Rubinson, D. A., et al. ((2003) Nat. Genet. 33:401-406) and Stewart, S. A., et al. ((2003) RNA 9:493-501). The RNA interference agents, e.g., the siRNAs or shRNAs, can be introduced along with components that perform one or more of the following activities: enhance uptake of the RNA interfering agents, e.g., siRNA, by the cell, e.g., lymphocytes or other cells, inhibit annealing of single strands, stabilize single strands, or otherwise facilitate delivery to the target cell and increase inhibition of the target gene, e.g., DRP1. The dose of the particular RNA interfering agent will be in an amount necessary to effect RNA interference, e.g., post translational gene silencing (PTGS), of the particular target gene, thereby leading to inhibition of target gene expression or inhibition of activity or level of the protein encoded by the target gene.

Small Molecule Inhibition of DRP1 Activity or Expression:

As used herein, the term "small molecule" refers to a chemical (e.g., organic or inorganic) agent including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Essentially any small molecule inhibitor of DRP1 expression and/or activity can be used in the treatment of a disease comprising hyperlipidemia (e.g., elevated LDL) using the methods described herein. Screening assays are provided herein for identifying candidate small molecule agents that inhibit DRP1 expression and/or activity.

In one embodiment, the DRP1 inhibitor is a small molecule. In one embodiment, the DRP1 inhibitor comprises Mdivi-1 (also known in the art as 3-(2,4-Dichloro-5-methoxyphenyl)-2,3-dihydro-2-thioxo-4(1H)-quinazolinone). In another embodiment, the DRP1 inhibitor is the peptide inhibitor P110 (see e.g., Qi et al. (2013) J Cell Sci 126:789-802). In other embodiments, the DRP1 inhibitor comprises 3-Hydroxynaphthalene-2-carboxylic acid-(3,4-dihydroxybenzylidene)-hydrazide, or 3-Hydroxynaphthalene-2-carboxylic acid (3,4-dihydroxybenzylidene)hydrazide.

Pharmaceutical Compositions

A DRP1 inhibitor can be formulated in any number of ways and can be tailored for a particular mode of administration, dose or other pharmacokinetic or pharmacodynamic property desired.

In some embodiments, the compositions described herein are formulated with a pharmaceutically acceptable carrier. In alternative embodiments, the pharmaceutical compositions and formulations of the invention can be administered parenterally, topically, orally or by local administration, such as by aerosol, intranasally, or transdermally. The pharmaceutical compositions can be formulated in any desired manner and can be administered in a variety of unit dosage forms depending upon the condition or disease (e.g., dyslipidemia), the degree of illness, the general medical condition of each patient, the resulting preferred method of administration and the like. Details on techniques for formulation and administration of pharmaceuticals are well described in the scientific and patent literature, see, e.g., the latest edition of Remington's Pharmaceutical Sciences, Maack Publishing Co, Easton Pa. ("Remington's").

Compositions as described herein can be administered alone or as a component of a pharmaceutical formulation. The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Compositions as described herein include those suitable for intradermal, inhalation, oral/nasal, topical, parenteral, rectal, and/or intravaginal administration. The formulations can be presented in unit dosage form and can be prepared by any methods well known in the art of pharmacy. The amount of active ingredient (e.g., DRP1 inhibitor(s)) which can be combined with a carrier material to produce a single dosage form will vary depending upon the host being treated, the particular mode of administration, e.g., oral, injection, intravenous, or inhalation. The amount of active ingredient which can be combined with a carrier material to produce a single dosage form will generally be that amount of the compound which produces a therapeutic effect, e.g., blood LDL cholesterol lowering effect.

Pharmaceutical formulations of the compositions described herein can be prepared according to any method known to the art for the manufacture of pharmaceuticals. Such drugs can contain sweetening agents, flavoring agents, coloring agents and preserving agents. A formulation can be admixed with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; and proteins, e.g., gelatin and collagen. Disintegrating or solubilizing agents can be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., DRP1 inhibitor) in an admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In one embodiment, oil-based pharmaceuticals are used for administration. Oil-based suspensions can be formulated by suspending an active agent (e.g., DRP1 inhibitor) in a vegetable oil, such as arachis oil, olive oil, sesame oil or coconut oil, or in a mineral oil such as liquid paraffin; or a mixture of these. Such oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid.

Pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical formulations described herein can also be administered by intranasal, intraocular and intravaginal routes including suppositories, insufflation, powders and aerosol formulations. Suppository formulations can be prepared by mixing the drug with a suitable non-irritating excipient which is solid at ordinary temperatures but liquid at body temperatures and will therefore melt in the body to release the drug. Such materials can be cocoa butter and polyethylene glycols. When treating chronic conditions, such as a detrimental inflammatory response or an autoimmune disease, oral administration may be preferred to ensure proper patient compliance with the therapeutic regimen.

The pharmaceutical compounds comprising a DRP1 inhibitor can be delivered transdermally, by a topical route, formulated as applicator sticks, solutions, suspensions, emulsions, gels, creams, ointments, pastes, jellies, paints, powders, and aerosols.

The pharmaceutical formulations described herein can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

Pharmaceutical formulations can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose, any bland fixed oil can be employed including synthetic mono- or diglycerides. In addition, fatty acids such as oleic acid can likewise be used in the preparation of injectables. These solutions are sterile and generally free of undesirable matter. These formulations can be sterilized by conventional, well known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and are selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The pharmaceutical compounds and formulations described herein can be lyophilized. Thus, provided herein are stable, lyophilized formulations comprising a composition as described herein, which can be made by lyophilizing a solution comprising a pharmaceutical of the invention and a bulking agent, e.g., mannitol, trehalose, raffinose, and sucrose or mixtures thereof.

The compositions and formulations comprising a DRP1 inhibitor can be delivered by the use of liposomes. By using liposomes, particularly where the liposome surface carries ligands specific for target cells (e.g., hepatocytes), or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587.

It is also contemplated herein that DRP1 inhibitors are administered directly to the site of a tumor, for example, by intratumoral injection. Alternatively, for the treatment of cancer a DRP1 inhibitor can be administered systemically or by any other route as described herein or known in the art for the treatment of cancer.

It will also be appreciated that the compounds and pharmaceutical compositions described herein can be formulated and employed in combination therapies, that is, the compounds and pharmaceutical compositions can be formulated with or administered concurrently with, prior to, or subsequent to, one or more other desired therapeutics, lifestyle interventions (e.g., weight loss, exercise etc.) or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a compound comprising a DRP1 inhibitor may be administered concurrently with another cholesterol-lowering or cardiovascular drug), or they may achieve different effects (e.g., control of any adverse effects of the DRP1 inhibitor).

The methods described herein can further comprise co-administration of the compositions comprising DRP1 inhibitors with other drugs or pharmaceuticals, e.g., compositions for treating a disease or disorder comprising elevated low-density lipoprotein. For example, the methods and/or compositions and formulations of the invention can be co-administered with a statin, a cholesterol absorption inhibitor, a bile acid binding resin, an anti-hypertension agent, statin, liver X receptor antagonist, 7-alpha hydroxylase, pterostilbine, fibrates, niacin, omega-3 fatty acids and any combinations thereof.

Useful combination therapies will be understood and appreciated by those of skill in the art. Potential advantages of such combination therapies include the ability to use less of each of the individual active ingredients to minimize toxic side effects, synergistic improvements in efficacy, improved ease of administration or use, and/or reduced overall expense of compound preparation or formulation.

In some embodiments, a combination of a DRP1 inhibitor with at least one additional agent herein can be used to maximize the effect of the compositions administered in an additive or synergistic manner. The effective amount of the compositions described herein can be administered to a selected human subject as a single daily dose, or alternatively, in more than one divided doses per day via any suitable administration route, e.g., oral administration.

Dosage and Administration

Therapeutic compositions or pharmaceutical compositions can be formulated for any desired conventional route of administration. Contemplated herein are routes known to be advantageous for treatment with a desired agent(s). In some embodiments, a route of administration can involve passage through the blood-brain barrier or direct contact with the endothelium. In some embodiments, the compositions can be formulated for systemic delivery. In some embodiments, the compositions can be formulated for delivery to specific organs, for example, the liver, spleen, bone marrow, and skin. Therapeutic compositions or pharmaceutical compositions can be formulated for aerosol application by inhalation for delivery to the lung or for systemic absorption via the lung. Alternatively, the therapeutic compositions or pharmaceutical compositions can also be formulated for a transdermal delivery, e.g., a skin patch. Therapeutic compositions or pharmaceutical compositions can be enteric coated and formulated for oral delivery. Therapeutic compositions or pharmaceutical compositions can be encapsulated in liposomes or nanoparticles and formulated for slow sustained delivery in vivo. Alternatively, the therapeutic compositions or pharmaceutical compositions can be formulated for targeted delivery, e.g., encapsulated in liposomes or nanoparticles that are designed and feature at least one targeting moiety on the liposomes or nanoparticles.

The DRP1 inhibitors and/or compositions as described herein can be administered by any known or desired route. By way of example, the DRP1 inhibitors described herein can be administered by a mucosal, pulmonary, topical, oral, intravenous, intratumoral, or other localized or systemic route (e.g., enteral and parenteral), among others. The DRP1 inhibitors can be administered by any desired route, for example by infusion or bolus injection, by absorption through epithelial or mucocutaneous linings (e.g., oral mucosa, rectal and intestinal mucosa, etc.) and may be administered together with other biologically active agents.

Routes of administration include, but are not limited to aerosol, direct injection, intradermal, transdermal (e.g., in slow release polymers), intravitreal, intramuscular, intraperitoneal, intravenous, subcutaneous, intranasal, epidural, topical, oral, transmucosal, buccal, rectal, vaginal, transdermal, intranasal and parenteral routes. "Parenteral" refers to a route of administration that is generally associated with injection, including but not limited to intraorbital, infusion, intraarterial, intracapsular, intracardiac, intradermal, intrahepatic, intrarogan, intramuscular, intraperitoneal, intrapulmonary, intraspinal, intrasternal, intrathecal, intrauterine, intravenous, intratumoral, subarachnoid, subcapsular, subcutaneous, transmucosal, or transtracheal. Any other therapeutically efficacious route of administration can be used, for example, infusion or bolus injection, absorption through epithelial or mucocutaneous linings, or by gene therapy wherein a DNA molecule encoding the therapeutic protein or peptide is administered to the patient, e.g., via a vector, which causes the protein or peptide to be expressed and secreted at therapeutic levels in vivo. In various embodiments, administration can be inhaled into the lung via aerosol administration, e.g., with nebulization. Administration also can be systemic or local.

In some embodiments, the DRP1 inhibitors (or compositions thereof) can be administered as a formulation adapted for delivery to a specific organ(s), for example, the liver. In addition, the DRP1 inhibitors described herein can be administered together with other components or biologically active agents, such as pharmaceutically acceptable surfactants (e.g., glycerides), excipients (e.g., lactose), carriers, diluents and vehicles.

The compositions comprising a DRP1 inhibitor as described herein can be administered therapeutically to a subject prior to, simultaneously with (in the same or different compositions) or sequentially with the administration of e.g., at least one lipid lowering therapy, cholesterol synthesis inhibitor, vitamin, high density lipoprotein (HDL) augmenter, anti-atherosclerotic agent, blood pressure lowering agent, blood thinner, or other cardiovascular agent. For example, the additional agent can be an HMG-CoA reductase inhibitor, a statin, 7-alpha hydroxylase, liver X receptor agonist, pterostilbine, bile acid binding resin, cholesterol absorption inhibitor, fibrates, niacin, or omega-3 fatty acids. The compositions comprising a DRP1 inhibitor as described herein can be administered as adjunctive and/or concomitant therapy to a lipid lowering or cardiovascular therapy.

In other embodiments, compositions comprising a DRP1 inhibitor can be administered therapeutically to a subject prior to, simultaneously with (in the same or different compositions) or sequentially with the administration of an anti-cancer therapy, for example, radiation, chemotherapy, cancer immunotherapy or surgical methods. Such therapies can either directly target a tumor (e.g., by inhibition of a tumor cell protein or killing of highly mitotic cells) or act indirectly, e.g., to provoke or accentuate an anti-tumor immune response. Exemplary anti-cancer agents that can be used in combination with DRP1 inhibitors for the treatment of cancer or inflammatory disorders include, but are not limited to, alkylating agents such as thiotepa and CYTOXAN™; cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas, such as carmustine, chlorozotocin, fotemustine, lomustine, nimustine, and ranimnustine; antibiotics such as the enediyne antibiotics (e.g., calicheamicin, especially calicheamicin gamma and calicheamicin omega); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN™, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK; polysaccharide complex (JHS Natural Products™ Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL™ paclitaxel (Bristol-Meyers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE™ doxetaxel (Rhone-Poulenc Rorer, Antony, France); chloranbucil; GEMZAR™, gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE™, vinorelbine; novantrone; teniposide; edatrexate; daunomycin; aminopterin; xeloda; ibandronate; irinotecan (CAMPTOSAR™, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX™); lapatinib (TYKERB™); inhibitors of PKC-alpha, Raf, H-Ras, EGFR (e.g., erlotinib (TARCEVA™)) and VEGF-A that reduce cell proliferation, and pharmaceutically acceptable salts, acids or derivatives of any of the above. In addition, the methods of treatment can further include the use of radiation.

In other embodiments, it is contemplated herein that a DRP1 inhibitor is administered in combination with other anti-inflammatory agents such as nonsteroidal anti-inflammatory drugs (NSAIDs) analgesics (e.g., diclofenac, ibuprofen, ketoprofen, and naproxen); corticosteroids (e.g., betamethasone, beclomethasone, cortisone, hydrocortisone, prednisone, and dexamethasone), and sulfasalazine, among others.

For parenteral (e.g., intravenous, subcutaneous, intramuscular) administration, the DRP1 inhibitor compositions described herein can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and non-aqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by commonly used techniques.

The dosage administered to a subject will vary depending upon a variety of factors, including the pharmacodynamic characteristics of the particular agents, and its mode and route of administration; size, age, sex, health, body weight and diet of the recipient; nature and extent of symptoms of the disease being treated, type of concurrent treatment, frequency of treatment, and the effect desired.

Usually a daily dosage of active ingredient can be about 0.01 to 500 milligrams per kilogram of body weight. Ordinarily 1 to 40 milligrams per kilogram per day given in divided doses 1 to 6 times a day or in sustained release form is effective to obtain desired results. The active ingredient will ordinarily be present in an amount of about 0.5-95% by weight based on the total weight of the composition. Second or subsequent administrations can be administered at a dosage which is the same, less than or greater than the initial or previous dose administered to the individual.

The skilled artisan will appreciate that certain factors may influence the dosage and timing required to effectively treat a subject, including but not limited to, the severity of the disease or disorder, previous treatments, the general health and/or age of the subject, and other diseases present.

The dosage range for the agent depends upon the potency, and includes amounts large enough to produce the desired effect, e.g., reduction in at least one symptom of e.g., high LDL, high total cholesterol, or atherosclerosis. The dosage should not be so large as to cause unacceptable adverse side effects. Generally, the dosage will vary with the type of inhibitor (e.g., an antibody or fragment, small molecule, siRNA, etc.) and with the age, condition, and sex of the patient. The dosage can be determined by one of skill in the art and can also be adjusted by the individual physician in the event of any complication. Typically, the dosage ranges from 0.1 mg/kg body weight to 1 g/kg body weight. In some embodiments, the dosage range is from 0.1 mg/kg body weight to 1 g/kg body weight, from 0.1 mg/kg body weight to 500 mg/kg body weight, from 0.1 mg/kg body weight to 250 mg/kg body weight, from 0.1 mg/kg body weight to 100 mg/kg body weight, from 0.1 mg/kg body weight to 50 mg/kg body weight, from 0.1 mg/kg body weight to 10 mg/kg body weight, from 10 mg/kg to 100 mg/kg, from 15 mg/kg to 100 mg/kg, from 20 mg/kg to 100 mg/kg, from 25 mg/kg to 100 mg/kg, from 30 mg/kg to 100 mg/kg, from 40 mg/kg to 100 mg/kg, from 50 mg/kg to 100 mg/kg, from 60 mg/kg to 100 mg/kg, from 70 mg/kg to 100 mg/kg, from 75 mg/kg to 100 mg/kg, from 25 mg/kg to 50 mg/kg, from 50 mg/kg to 200 mg/kg, from 75 mg/kg to 250 mg/kg, from 100 mg/kg to 300 mg/kg, from 100 mg/kg to 200 mg/kg, from 100 mg/kg to 400 mg/kg, from 100 mg/kg to 500 mg/kg, from 100 mg/kg to 750 mg/kg from 200 mg/kg to 1000 mg/kg, from 300 mg/kg to 1000 mg/kg, from 400 mg/kg to 1000 mg/kg, from 500 mg/kg to 1000 mg/kg, from 600 mg/kg to 1000 mg/kg, from 700 mg/kg to 1000 mg/kg, from 800 mg/kg to 1000 mg/kg, from 900 mg/kg to 1000 mg/kg, from 250 mg/kg to 750 mg/kg, from 300 mg/kg to 600 mg/kg, or any range therebetween.

Administration of the doses recited above can be repeated for a limited period of time. In some embodiments, the doses are given once a day, or multiple times a day, for example but not limited to three times a day. In another embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

A therapeutically effective amount is an amount of an agent that is sufficient to produce a statistically significant, measurable change in at least one symptom of a disease or disorder comprising high LDL levels (see "Efficacy Measurement" below). Such effective amounts can be gauged in clinical trials as well as animal studies for a given agent. In one embodiment, efficacy can be measured by assessing sensitivity of the subject to conventional statin therapy.

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. An agent can be targeted by means of a targeting moiety, such as e.g., an antibody or targeted liposome technology. In some embodiments, an agent can be targeted to a tissue by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. The addition of an antibody to an agent permits the agent to accumulate additively at the desired target site (e.g., the liver). Antibody-based or non-antibody-based targeting moieties can be employed to deliver a ligand or the inhibitor to a target site. Preferably, a natural binding agent for an unregulated or disease associated antigen is used for this purpose.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent injection or other administration. Alternatively, continuous intravenous infusion sufficient to maintain concentrations in the blood or skeletal muscle tissue in the ranges specified for in vivo therapies are contemplated.

Efficacy Measurement

Efficacy testing can be performed during the course of treatment using the methods described herein. Measurements of the degree of severity of a number of symptoms associated with a particular ailment are noted prior to the start of a treatment and then at a second, specific time period after the start of the treatment.

The efficacy of a given treatment for a disorder comprising elevated levels of low-density lipoprotein as described herein can be determined by the skilled clinician. However, a treatment is considered "effective treatment," as the term is used herein, if any one or all of the signs or symptoms of the disease or disorder is/are altered in a beneficial manner (e.g., reduced blood LDL levels, reduced total cholesterol in blood, restored sensitivity to statin therapy, reduced deposition of cholesterol in vessels and/or reduced atherosclerotic plaque size, etc.), other clinically accepted symptoms or markers of disease are improved, or even ameliorated, e.g., by at least 10% following treatment with an agent comprising a DRP1 inhibitor. Efficacy can also be measured by failure of an individual to worsen as assessed by stabilization of the disease or disorder, hospitalization or need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing progression of abnormal bone growth; or (2) relieving the disease, e.g., causing regression of symptoms; and (3) preventing or reducing the likelihood of the development of a disease (e.g., development of atherosclerosis, myocardial infarction or stroke).

An effective amount for the treatment of a disease means that amount which, when administered to a mammal in need thereof, is sufficient to result in effective treatment as that term is defined herein, for that disease. Efficacy of an agent can be determined by assessing blood levels of low-density lipoprotein or total cholesterol.

The present invention may be as defined in any one of the following numbered paragraphs.

1. A method for reducing blood cholesterol levels, the method comprising administering an effective amount of an inhibitor of dynamin-related protein 1 (DRP1) or administering an effective amount of a composition comprising an inhibitor of DRP1 to a human or non-human subject in need thereof, thereby reducing blood cholesterol levels in the subject.

2. The method of paragraph 1, wherein the inhibitor of DRP1 inhibits DRP1 expression.

3. The method of paragraph 1 or 2, wherein the inhibitor of DRP1 expression is selected from a small molecule or a nucleic acid.

4. The method of paragraph 1, 2, or 3, wherein the nucleic acid is a DRP1 specific RNA interference agent, or a vector encoding a DRP1-specific RNA interference agent.

5. The method of any one of paragraphs 1-4, wherein the DRP1-specific RNA interference agent is targeted for delivery to the liver.

6. The method of any one of paragraphs 1-5, wherein the inhibitor of DRP1 inhibits DRP1 activity.

7. The method of paragraph 6, wherein the inhibitor of DRP1 activity is selected from the group consisting of an antibody against DRP1 or an antigen-binding fragment thereof, a small molecule, and a nucleic acid.

8. The method of paragraph 7, wherein the nucleic acid is a DRP1-specific RNA interference agent, a vector encoding a RNA interference agent, or an aptamer that binds DRP1.

9. The method of any one of paragraphs 1-8, wherein the DRP1 inhibitor is administered with a pharmaceutically acceptable carrier.

10. The method of any one of paragraphs 1-9, wherein the DRP1 inhibitor is administered with at least one additional cholesterol lowering agent.

11. The method of any one of paragraphs 1-10, wherein the at least one additional cholesterol lowering agent is selected from the group consisting of: statin, 7-alpha hydroxylase, liver X receptor agonist, bile acid binding resins, cholesterol absorption inhibitors, fibrates, niacin, omega-3 fatty acids, and pterostilbene.

12. The method of any one of paragraphs 1-11, wherein the DRP1 inhibitor causes a reduction of low density lipoprotein in the subject.

13. The method of any one of paragraphs 1-12, wherein the DRP1 inhibitor causes a reduction of serum proprotein convertase subtilisin/kexin type 9 (PCSK9) in the subject.

14. The method of any one of paragraphs 1-13, wherein the DRP1 inhibitor causes a reduction of PCSK9 mRNA in cells of the subject.

15. The method of any one of paragraphs 1-14, wherein the subject has a high level of cholesterol or a high level of low density lipoprotein.

16. The method of any one of paragraphs 1-15, wherein the subject has exhibited intolerance to conventional statin therapy.

17. A pharmaceutical composition comprising an effective amount of an inhibitor of dynamin-related protein 1 (DRP1), and a pharmaceutically acceptable carrier.

18. A method for reducing the secretion and expression of proprotein convertase subtilisin/kexin type 9 (PCSK9) in a cell, the method comprising: contacting the cell with an effective amount of a composition comprising an inhibitor of dynamin-related protein 1 (DRP1) or a an effective amount of a composition comprising an inhibitor of DRP1, whereby the level of PCSK9 expression and/or secretion is decreased in the cell relative to the level of PCSK9 expression and/or secretion in the cell prior to contacting with the DRP1 inhibitor.

19. A method for decreasing proprotein convertase subtilisin/kexin type 9 (PCSK9) serum levels in a mammal in need thereof, the method comprising the step of contacting a cell in the mammal with an effective amount of a composition comprising an inhibitor of dynamin-related protein 1 (DRP1) or a an effective amount of a composition comprising an inhibitor of DRP1, whereby the level of PCSK9 expression and/or secretion is decreased in said mammal, relative to the level of PCSK9 expression and/or secretion prior to said contacting.

20. A method for increasing the expression of low-density lipoprotein receptor (LDLR) on a cell, the method comprising: contacting the cell with an effective amount of a composition comprising an inhibitor of dynamin-related protein 1 (DRP1) or a an effective amount of a composition comprising an inhibitor of DRP1, whereby the level of LDLR expression is increased in the cell relative to the level of LDLR expression in the cell prior to contacting with the DRP1 inhibitor.

21. A method for treating cancer or an inflammatory disease or disorder, the method comprising administering an effective amount of an inhibitor of dynamin-related protein 1 (DRP1) or administering an effective amount of a composition comprising an inhibitor of DRP1 to a human or non-human subject in need thereof, thereby treating the cancer of inflammatory disease/disorder in the subject.

22. The method of paragraph 21, wherein the DRP1 inhibitor is administered in combination with at least one anti-inflammatory agent and/or anti-cancer agent.

23. A dynamin-related protein 1 (DRP1) inhibitor for use in the treatment of elevated cholesterol in a subject.

24. A dynamin-related protein 1 (DRP1) inhibitor for use in the manufacture of a medicament for the treatment of elevated cholesterol in a subject.

25. Use of a dynamin-related protein 1 (DRP1) inhibitor for the treatment of elevated cholesterol in a subject.

26. Use of a dynamin-related protein 1 (DRP1) inhibitor in the manufacture of a medicament for the treatment of elevated cholesterol in a subject.

27. Use of a dynamin-related protein (DRP1) inhibitor in the manufacture of a medicament for the treatment of cancer.

28. Use of a dynamin-related protein (DRP1) inhibitor in the manufacture of a medicament for the treatment of an inflammatory disease or disorder.

29. A dynamin-related protein 1 (DRP1) inhibitor for use in the treatment of cancer or an inflammatory disease/disorder in a subject.

This invention is further illustrated by the following example(s) which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the invention described herein. Such equivalents are intended to be encompassed by the following claims.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Unless otherwise explained, all technical and scientific terms used herein have the same meaning as commonly understood by one of ordinary skill in the art to which this disclosure belongs. It should be understood that this disclosure is not limited to the particular methodology, protocols, and reagents, etc., described herein and as such can vary. The terminology used herein is for the purpose of describing particular embodiments only, and is not intended to limit the scope of the present invention, which is defined solely by the claims.

Definitions of common terms in molecular biology can be found in The Merck Manual of Diagnosis and Therapy, 19th Edition, published by Merck Sharp & Dohme Corp., 2011 (ISBN 978-0-911910-19-3), (Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties. Further, unless otherwise required by context, singular terms shall include pluralities and plural terms shall include the singular.

Unless otherwise stated, the present invention was performed using standard procedures known to one skilled in the art, for example, in Michael R. Green and Joseph Sambrook, Molecular Cloning: A Laboratory Manual, Cold Spring Harbor Laboratory Press, Cold Spring Harbor, N.Y., USA (2012); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, Transgenesis Techniques by Alan R. Clark editor, second edition, 2002, Humana Press, and Methods in Molecular Biology, Vo. 203, 2003, Transgenic Mouse, edited by Marten H. Hofker and Jan van Deursen, which are all herein incorporated by reference in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The disclosure described herein, in a preferred embodiment, does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

It is also envisioned that the methods described herein can be used as prophylaxis.

EXAMPLES

Example 1: Background

Proteostasis, in which cells regulate protein homeostasis, is achieved through biogenesis, folding and maturation, transport, the ubiquitin-proteasome system, and autophagic/lysosomal-mediated protein degradation mechanisms. Dysfunctional proteostasis is associated with various disorders, including diabetes mellitus, cancer, neurodegenerative, and cardiovascular diseases[1]. Related to protein regulation in cardiovascular disease, proprotein convertase subtilisin/kexin type 9 (PCSK9), a crucial regulator of low-density lipoprotein metabolism, is involved in autophagy-mediated apolipoprotein B metabolism[2], vascular inflammation[3], and is associated with increased cardiovascular risk[4-6]. PCSK9 small molecule inhibitor development has proven difficult, but if achieved could provide a broader role for PCSK9 inhibition beyond antibody therapies that, due to high cost, are only available to a restricted patient population[7,8].

Nascent PCSK9 is transported from the endoplasmic reticulum (ER) via coat protein complex II (COPII) vesicles to the Golgi, it is then secreted and binds low-density lipoprotein receptor (LDLR), internalizes, and directs LDLR to the lysosome leading to its degradation. COPII cargo adaptor protein, SEC24A deficiency reduces PCSK9 secretion in mice[9]. Independent of its role in ER-to-Golgi trafficking, SEC24 is involved in autophagosome formation, an early step in autophagy[10]. PCSK9 also interacts with the molecular chaperone, glucose-regulated protein 94 in the early secretory pathway, and in its absence, LDLR is more sensitive to PCSK9 mediated degradation[11]. Glucose-regulated protein 94 clears misfolded proteins from the ER via the proteasome, whereas glucose-regulated protein 94 deficiency switches misfolded protein clearance from the proteasome to the autophagic/lysosomal pathway[12]. Taken together these studies associate PCSK9 with the early secretory pathway and ER-localized regulators of autophagy and proteasome-mediated protein degradation.

Dynamin-related protein 1 (DRP1), participates in mitochondrial membrane fission[13,14], and has been suggested as a therapeutic target in diseases associated with altered proteostasis, including: diabetes mellitus[15], cancer[16], neurodegenerative[17], and cardiovascular diseases[18-21]. In cardiovascular disease models, DRP1 inhibition prevents vascular neointima formation in rat balloon[18] and mouse wire[19] injury models, and suppresses lesion formation in diabetic apolipoprotein E-deficient mice[20]. It was recently reported that DRP1 inhibition suppresses osteogenic differentiation-induced collagen secretion and vascular smooth muscle and valve interstitial cell calcification[21]. Mice in which Drp1 is knocked out in the liver (Drp1LiKO) are resistant to diet-induced obesity, have less glucose tolerance impairment, reduced very low-density lipoprotein secretion, and lower serum total cholesterol and triglycerides on a high fat diet, with no alterations in liver lipid and ATP content, or mitochondrial respiratory activity[22].

Whether DRP1 is involved in protein secretion and proteostasis is unclear. Cytosolic DRP1 localizes to membranes, is enriched in fractions containing secretory proteins, and is partially ER localized in rat liver[23]. Dominant negative DRP1 decreased secretion of a co-transfected luciferase protein, and overexpressing wild-type DRP1 increased its secretion in Chinese hamster ovary cells[24]. DRP1 did not mediate effects on the secretory pathway analyzed by co-transfecting COS-7 cells with dominant negative DRP1 and GFP-tagged vesicular stomatitis virus glycoprotein, an exocytosed protein[25]. Ubiquitin binding protein p62, a component of ubiquitinated protein autophagy-mediated protein clearance and proteasomal degradation, is increased in the hearts of cardiomyocyte Drp1-deficient mice[26]. Cardiac Drp1-deficient mice have suppressed autophagic flux[27]; however, Drp1 deficiency does not significantly affect autophagy efficacy in mouse embryonic fibroblasts[28]. Mammalian cells express multiple DRP1 isoforms, with cell and tissue specificity[29]. Therefore, given the association of DRP1 with secretory proteins in the liver23 and the involvement of DRP1 in regulating lipoprotein secretion and serum lipids under high fat diet[22], the inventors sought to examine the role of DRP1 in hepatic proteostasis and protein secretion, including PCSK9 regulation.

Example 2

Clinical evidence has established that elevated levels of LDL cholesterol increase cardiovascular risk, with PCSK9 being a key regulator of LDL metabolism (1-3). Secreted PCSK9 binds LDL receptor (LDLR), internalizes and then directs LDLR to the lysosome leading to its degradation instead of recycling to the plasma membrane. Substantial effort has been made targeting PCSK9; however, small molecule inhibitor development has proven difficult, but if achieved could provide a broader role for PCSK9 therapies (4, 5). The data provided herein show that DRP1 regulates PCSK9 secretion likely through fission of select endoplasmic reticulum (ER) vesicles. It was found that DRP1 small molecule inhibition or CRISPR/Cas9-mediated knockout in human liver cells, and liver specific deletion in mice substantially reduced PCSK9 secretion.

DRP1 is a well-established regulator of mitochondrial fission (6, 7), although whether DRP1 regulates protein trafficking through ER membrane fission has not been established. DRP1 is enriched in fractions containing secretory proteins, and ER localized in rat liver (8). Dominant negative DRP1 in CHO cells decreased secretion of a co-transfected luciferase protein, while overexpressing wild-type DRP1 increased secretion (9). Liver specific Drp1 knockout mice (Drp1LiKO) on high fat diet have reduced very low density lipoprotein (VLDL) secretion without altering liver lipid and ATP content, or mitochondrial respiratory activity (10). Nascent VLDL particles exit the ER in coat protein complex (COP)II-dependent vesicles that are different from those of newly synthesized proteins (11). Standard COPII vesicles are typically described as 60-80 nm in diameter, but ER vesicles also have to accommodate larger cargos including lipoproteins and collagen that can well exceed 100 nm. Despite the fundamental importance of this transport process, the molecular details of how it occurs remain poorly understood. This raises the hypothesis that DRP1 may be an ER equivalent of plasma membrane dynamin, a GTPase involved in the scission of endocytic vesicles. As such, DRP1 may function in an auxiliary constriction/fission role for select ER secretory vesicles, particularly those transporting bulky cargos. However, no DRP1 mediated effects on the secretory pathway analyzed by co-transfecting COS-7 cells with dominant negative DRP1 and GFP-tagged VSV-G were observed (12). Given these results, this study seeks to clarify whether DRP1 regulates the secretion of select ER cargos.

DRP1 Facilitated Select Protein Secretion from Human Liver Cells

To assess DRP1 involvement in protein secretion, secretome changes were quantified using stable isotope labeling by amino acids in cell culture (SILAC). HepG2 human hepatocyte-like cells were treated for 24 hours with or without the selective DRP1 inhibitor Mdivi-1.[30] Mdivi-1 inhibits DRP1 mediated membrane fission by blocking DRP1 self-assembly stimulated GTPase activity without acting as a general GTPase inhibitor or as an inhibitor of other dynamin related protein family members, and does not change the actin cytoskeleton or ER network.[30,31] Mdivi-1 was added at a concentration that fully inhibits DRP1[30], and analyzed for changes in protein secretion. Six replicate SILAC experiments were performed and their data combined and filtered for proteins supported by two or more unique peptides.[32] 217 secreted proteins by two or more unique peptides were identified, of which 36 had a fold-change greater than two and a P-value less than 0.05 following Mdivi-1 treatment (data not shown). Comparison of the significantly changed HepG2 protein SILAC dataset with its closeness to disease modules showed association to both atherosclerosis and hypercholesterolemia (FIG. XX). Pathway network analysis of significantly altered proteins included several cardiovascular relevant pathways, including platelet degranulation (FIG. XX), in line with a previous report involving Mdivi-1 impairment of platelet granule exocytosis[33]. As the strongest secretion reduction was observed with PCSK9 (−74%; FIG. XX Figure IA), a clinically important target, the study was then focused on validating DRP1 regulation of PCSK9 secretion.

DRP1 Inhibition Reduced PCSK9 Secretion in Human Liver Cells

Figure 1B:
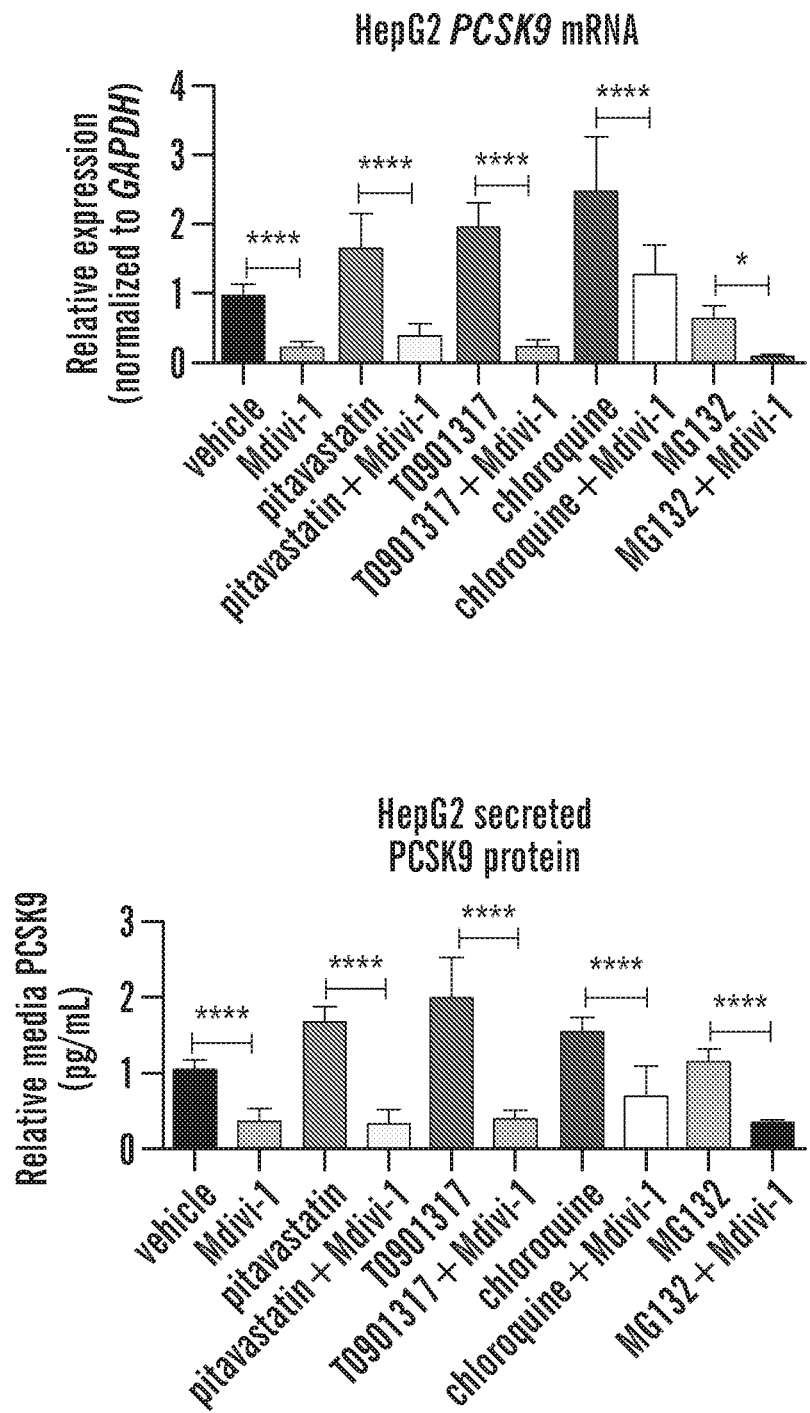
Figure 1C:
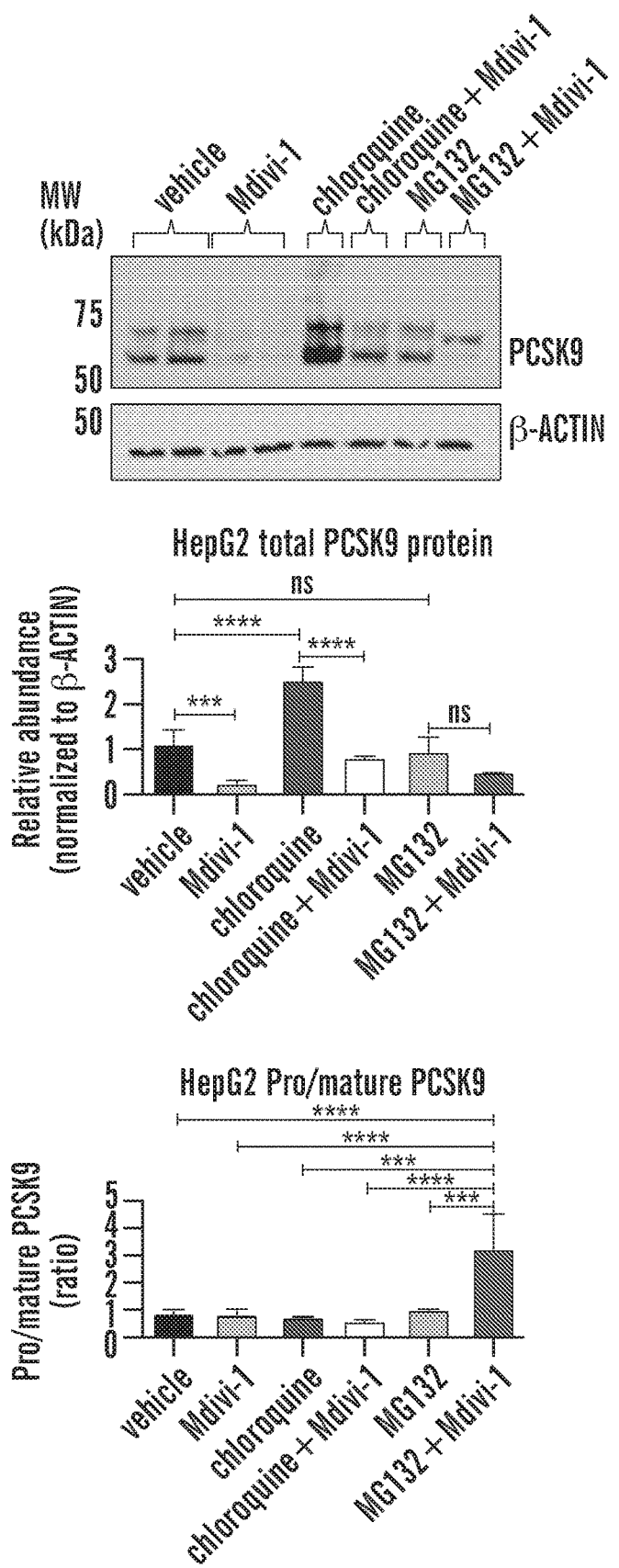
Figure 1D:
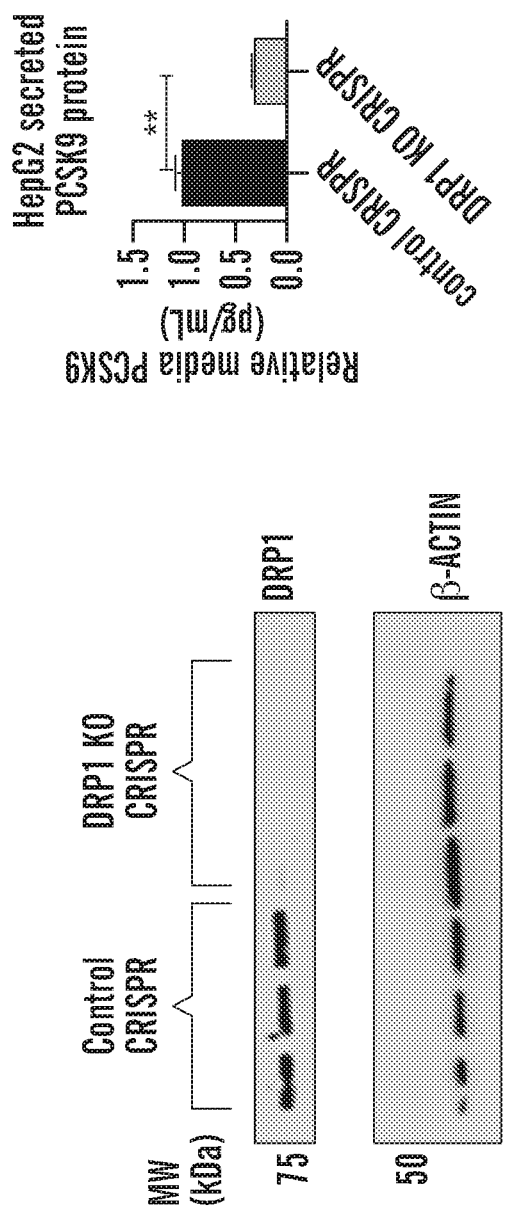
Figure 8A:
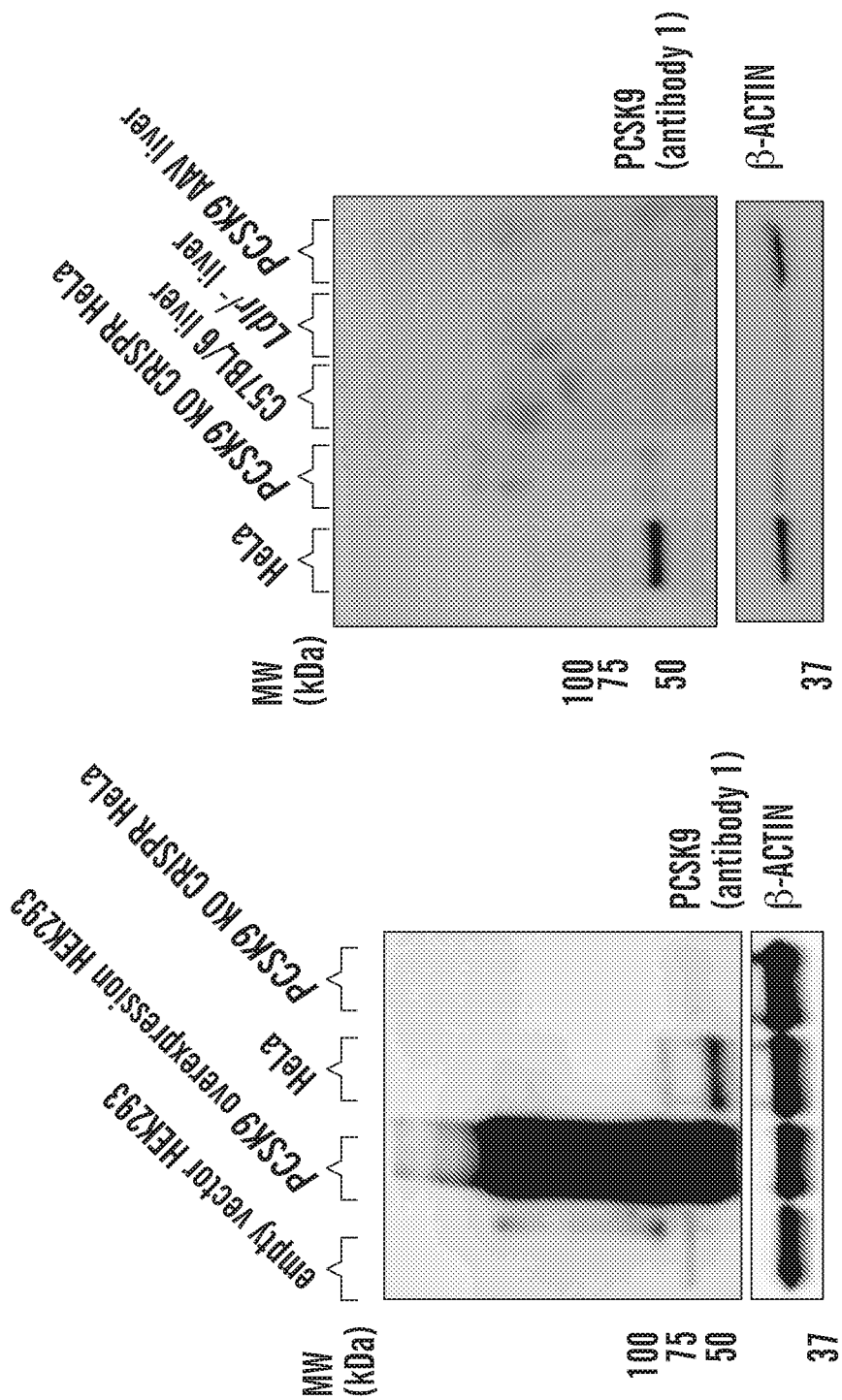
FIGS. 8A-8B PCSK9 and LDLR antibody confirmation.
Figure 8B:
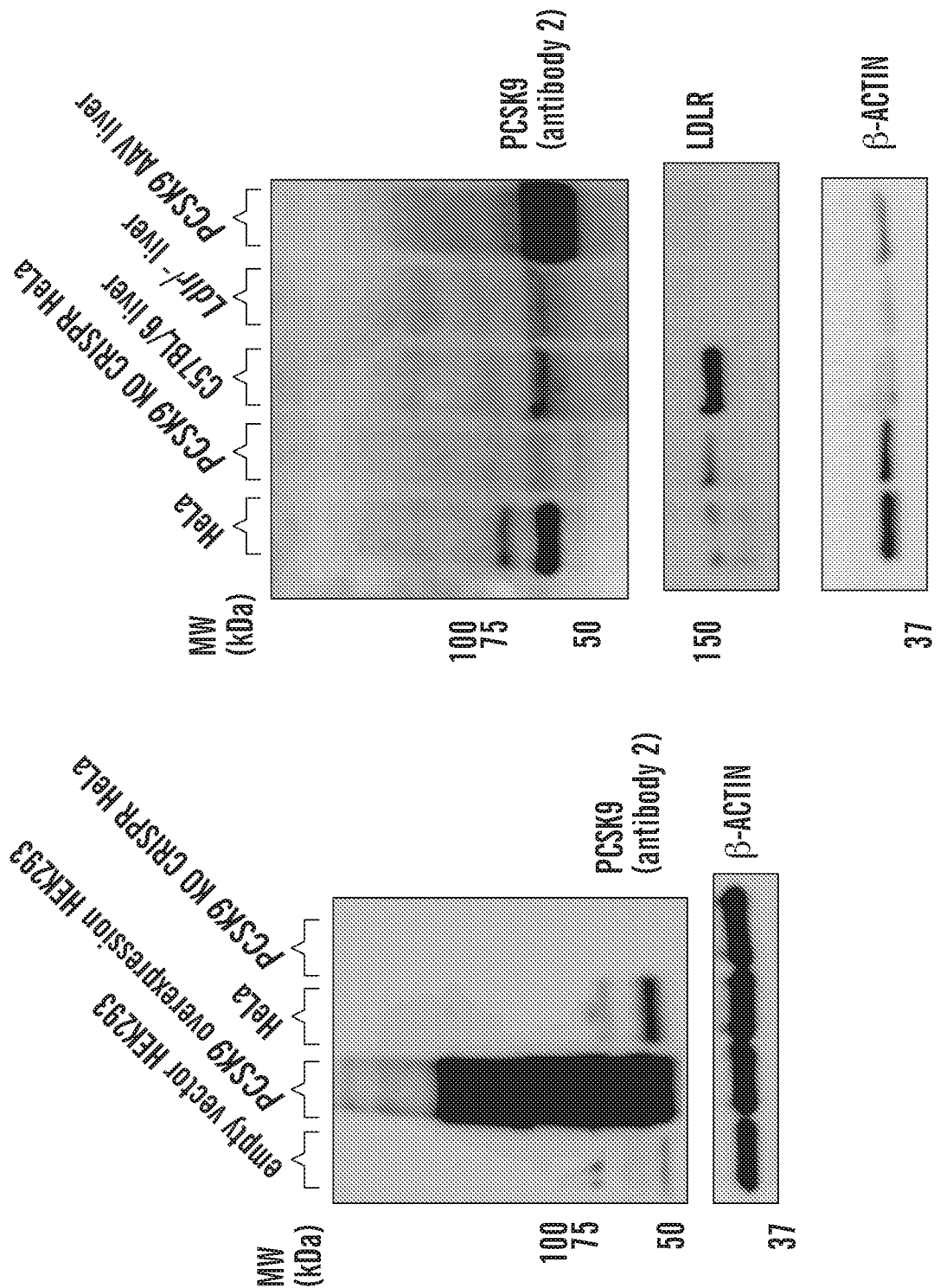
Figure 9A:
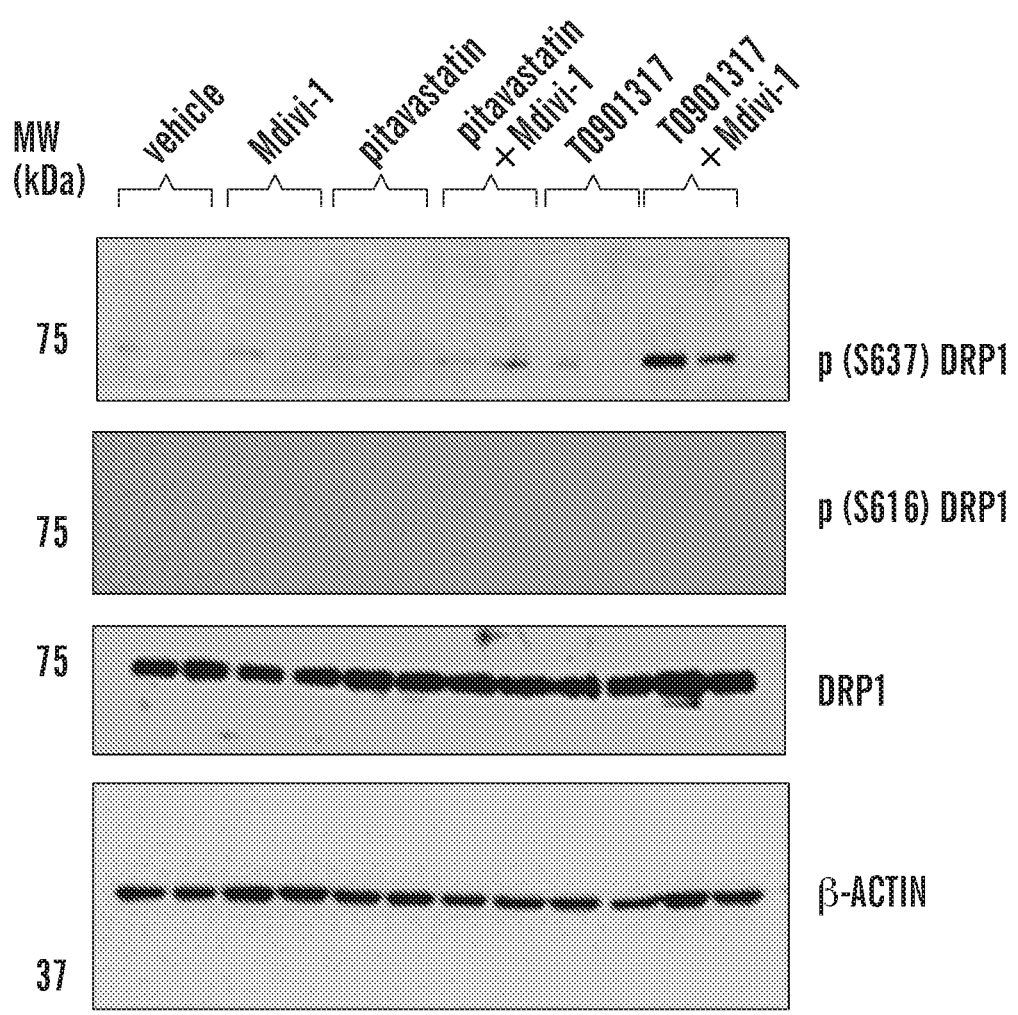
FIGS. 9A-9D DRP1 inhibition does not alter human liver cell DRP1 abundance.
Figure 9A:
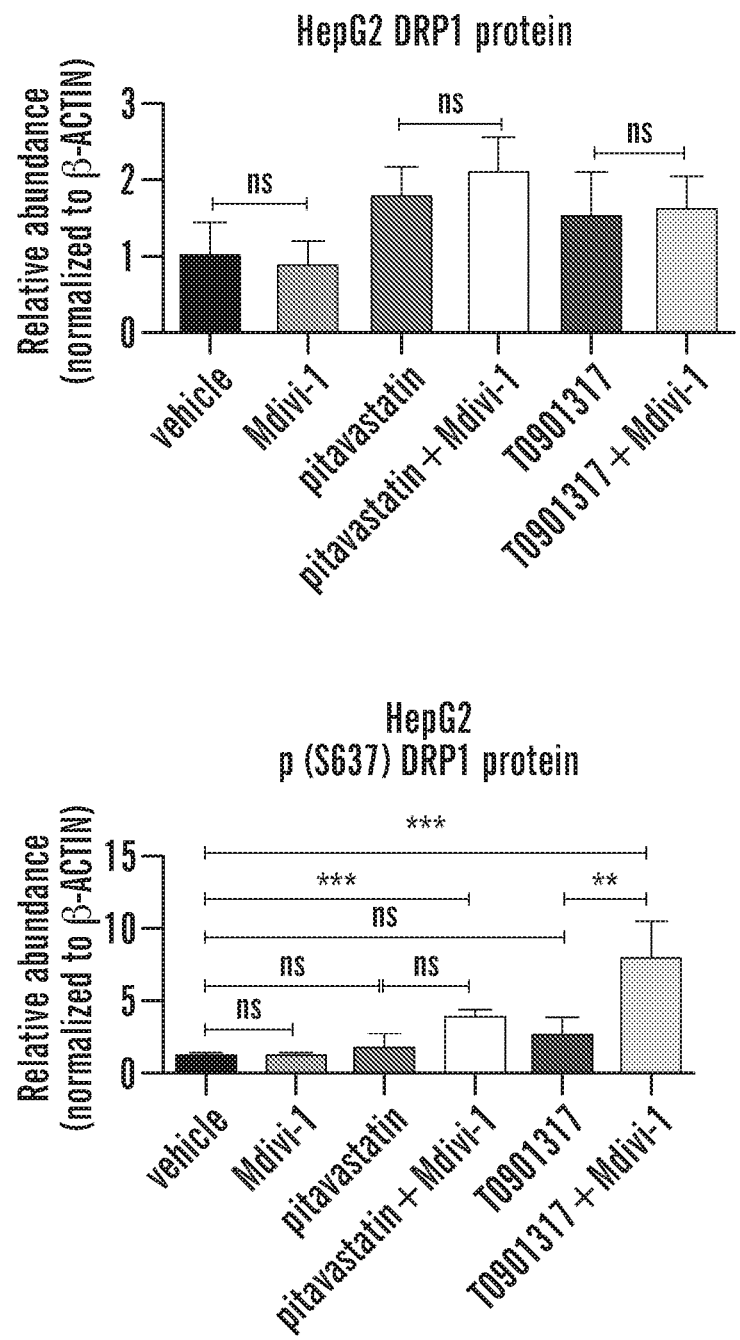
Figure 9B:
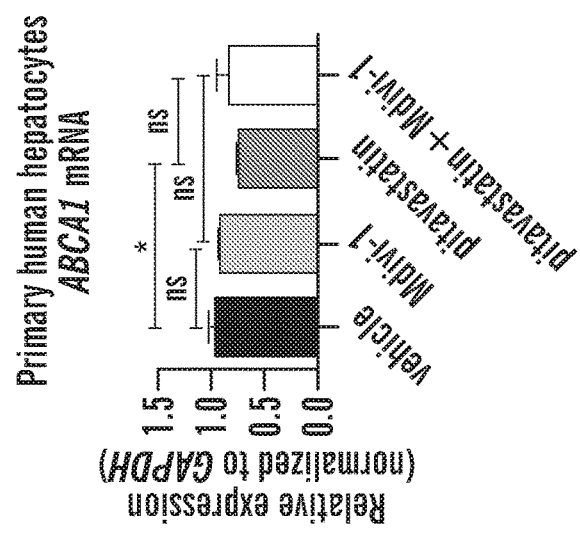

It was confirmed by ELISA that Mdivi-1 reduced PCSK9 secretion in HepG2 cells (−76.1%) (FIG. 1B). Cellular PCSK9 mRNA and protein abundance was also reduced by Mdivi-1 in HepG2 (FIGS. 1B and C; PCSK9 antibody confirmation FIG. 8), without altering DRP1 protein content or cell viability (FIGS. 9A & 9B). Treatment with the autophagosome-lysosome fusion and degradation inhibitor, chloroquine, increased PCSK9 secretion (FIG. 1B). Combining Mdivi-1 with the proteasome inhibitor, MG132 resulted in a buildup of ER pro-PCSK9 (FIG. 1C) while maintaining reduced PCSK9 secretion (FIG. 1B). Lipofectamine siRNA reagent reduced PCSK9 expression compared to non-treated HepG2. Therefore, to demonstrate inhibitor specificity CRISPR/Cas9 was used to knockout DRP1 in HepG2 cells, which in agreement with the Mdivi-1 data, reduced PCSK9 secretion (−66.8%) (FIG. 1D).

Figure 1E:
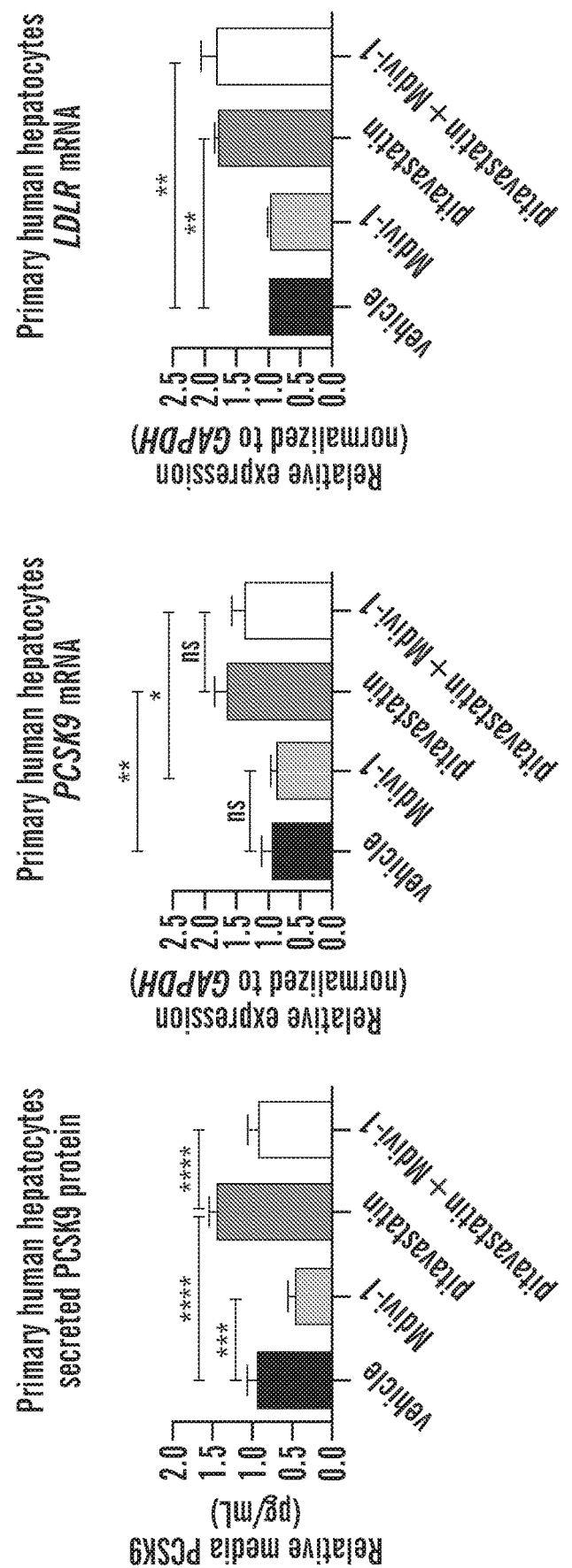
Figure 1F:
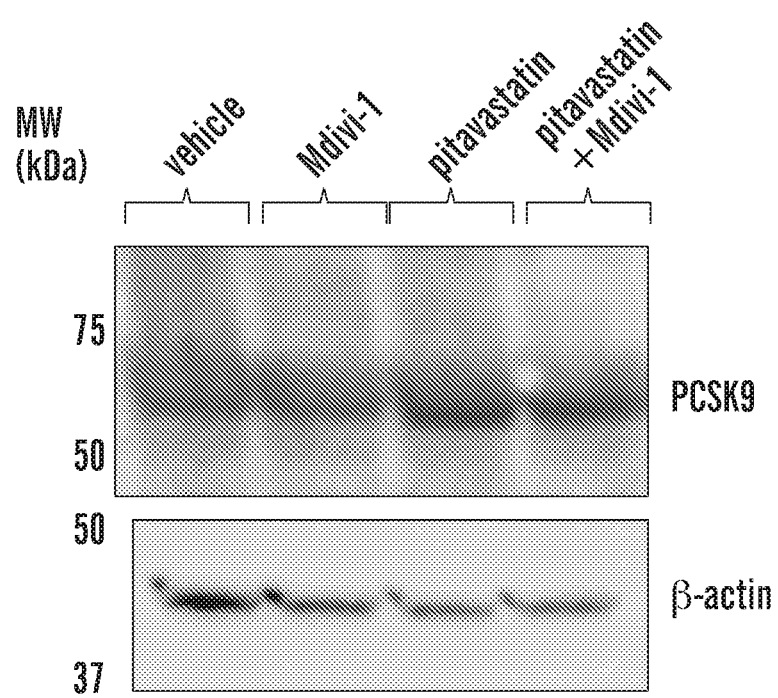
Figure 2A:
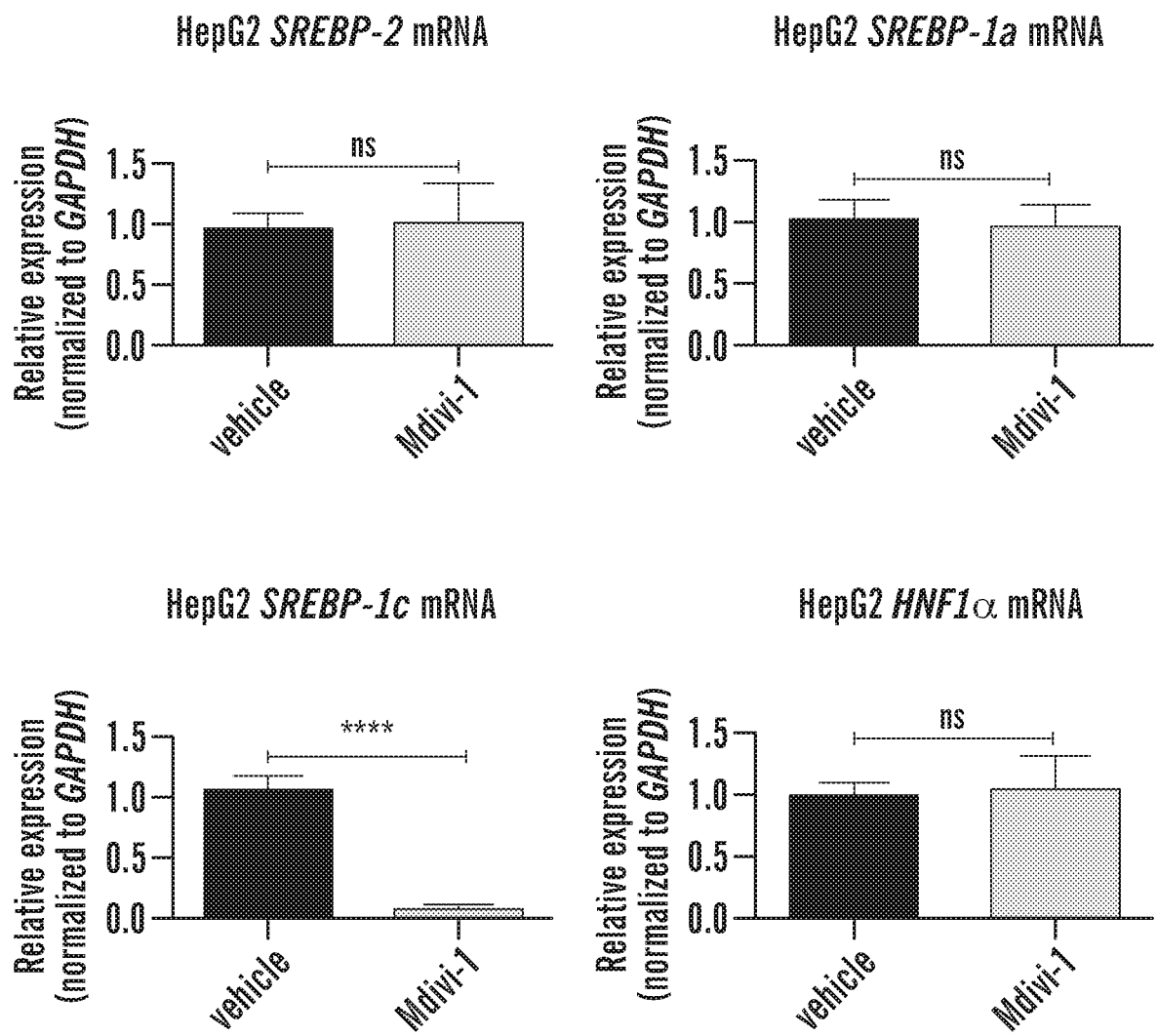
FIGS. 2A-2D. DRP1 inhibition increases HepG2 LDLR via c-Jun.
Figure 9C:
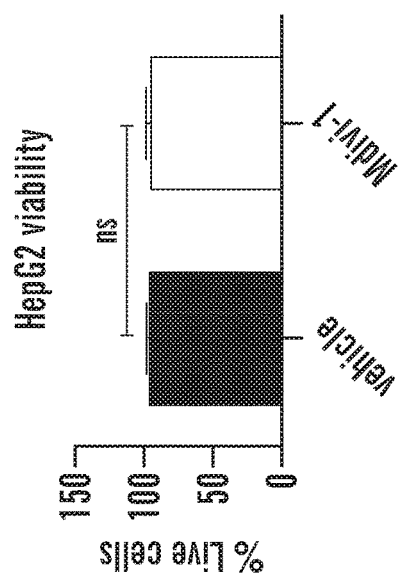
Figure 9C:
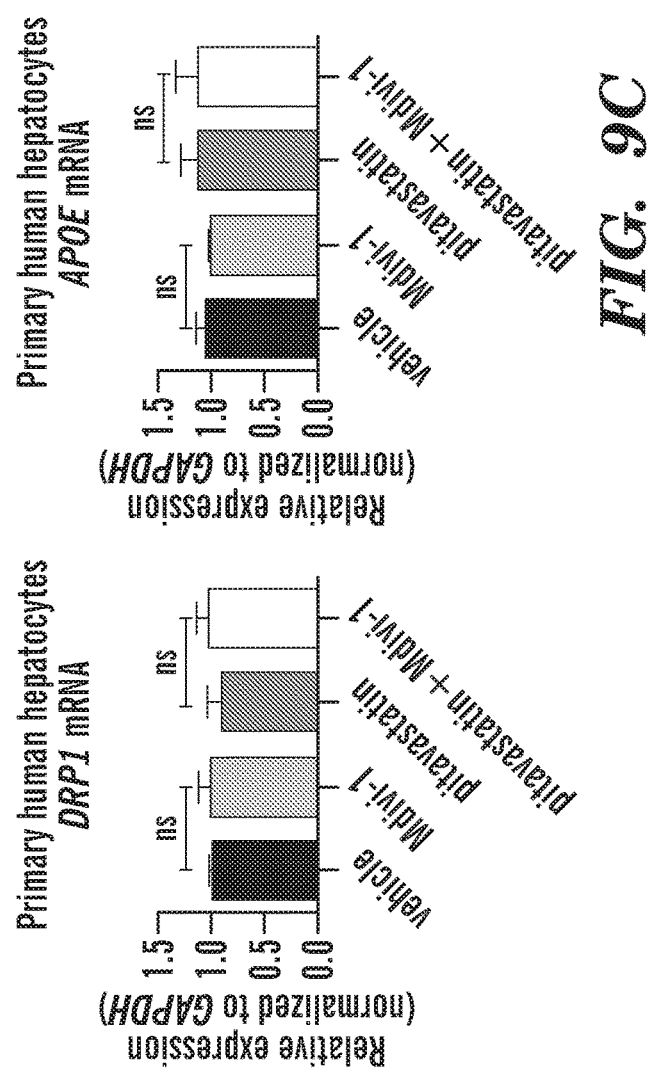
Figure 9D:
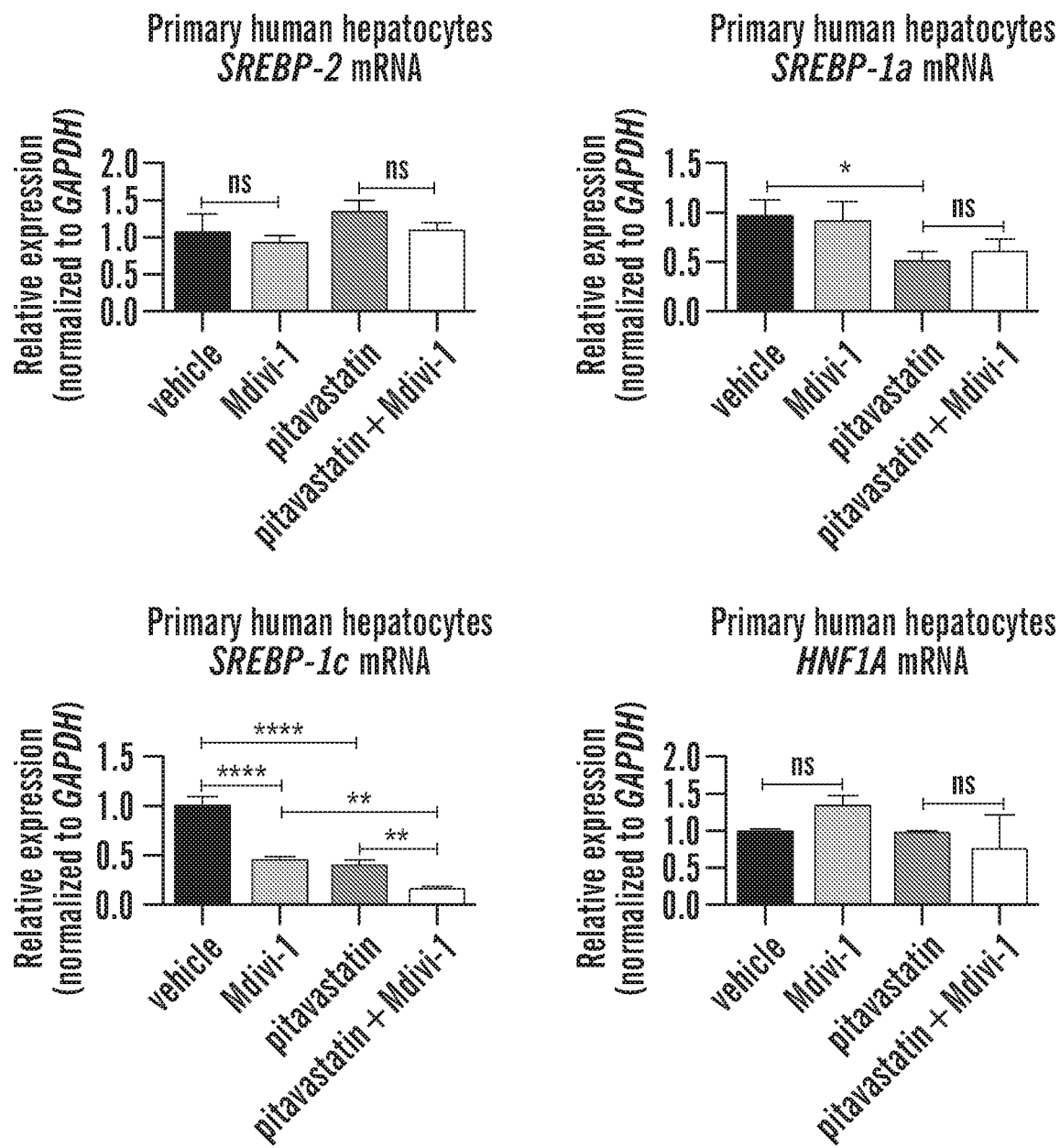

Sterol regulatory element binding-protein (SREBP), a regulator of PCSK9 expression, is transported from the ER to the Golgi by COPII34, resulting in its cleavage and activation. Reduced PCSK9 secretion via SEC24A deficiency does not inhibit SREBP9, indicating distinct PCSK9 and SREBP transport from the ER. To examine if DRP1 inhibition modulates SREBP trafficking, two different approaches were utilized to induce HepG2 PCSK9 expression by SREBP activation; both maintained reduced PCSK9 secretion when combined with DRP1 inhibition: pitavastatin[35] with Mdivi-1 (−75%) and liver X receptor agonist T090131736 with Mdivi-1 (−65.2%) (FIG. 1B). Mdivi-1 reduced PCSK9 secretion in primary human hepatocytes (FIG. 1E) while maintaining a statin-mediated SREBP transcriptional induction of PCSK9 and LDLR, without altering cellular PCSK9 protein (FIG. 1F), or the expression of DRP1 and the liver X receptor target genes, APOE and ABCA1 (FIG. 9C). This result supports selective PCSK9 transport modulation by DRP1 inhibition rather than global ER-to-Golgi trafficking disruption, along with indicating combinatory therapeutic potential for DRP1 inhibitors with statin and liver X receptor agonist. Expression of PCSK9 regulating transcription factors hepatic nuclear factor 1-alpha (HNF1A), SREBP-2, and SREBP-1a was not changed by Mdivi-1; whereas Mdivi-1 strongly reduced PCSK9 and SREBP-1c mRNA in HepG2, and SREBP-1c to a lesser extent, but not PCSK9 in primary human hepatocytes (FIG. 2A, FIG. 9D). These data suggest HepG2 PCSK9 expression may be more sensitive to SREBP-1c regulation than primary hepatocytes, while also supporting Mdivi-1 can reduce PCSK9 secretion in combination with and independent of SREBP1c-regulated PCSK9 expression.

Figure 2B:
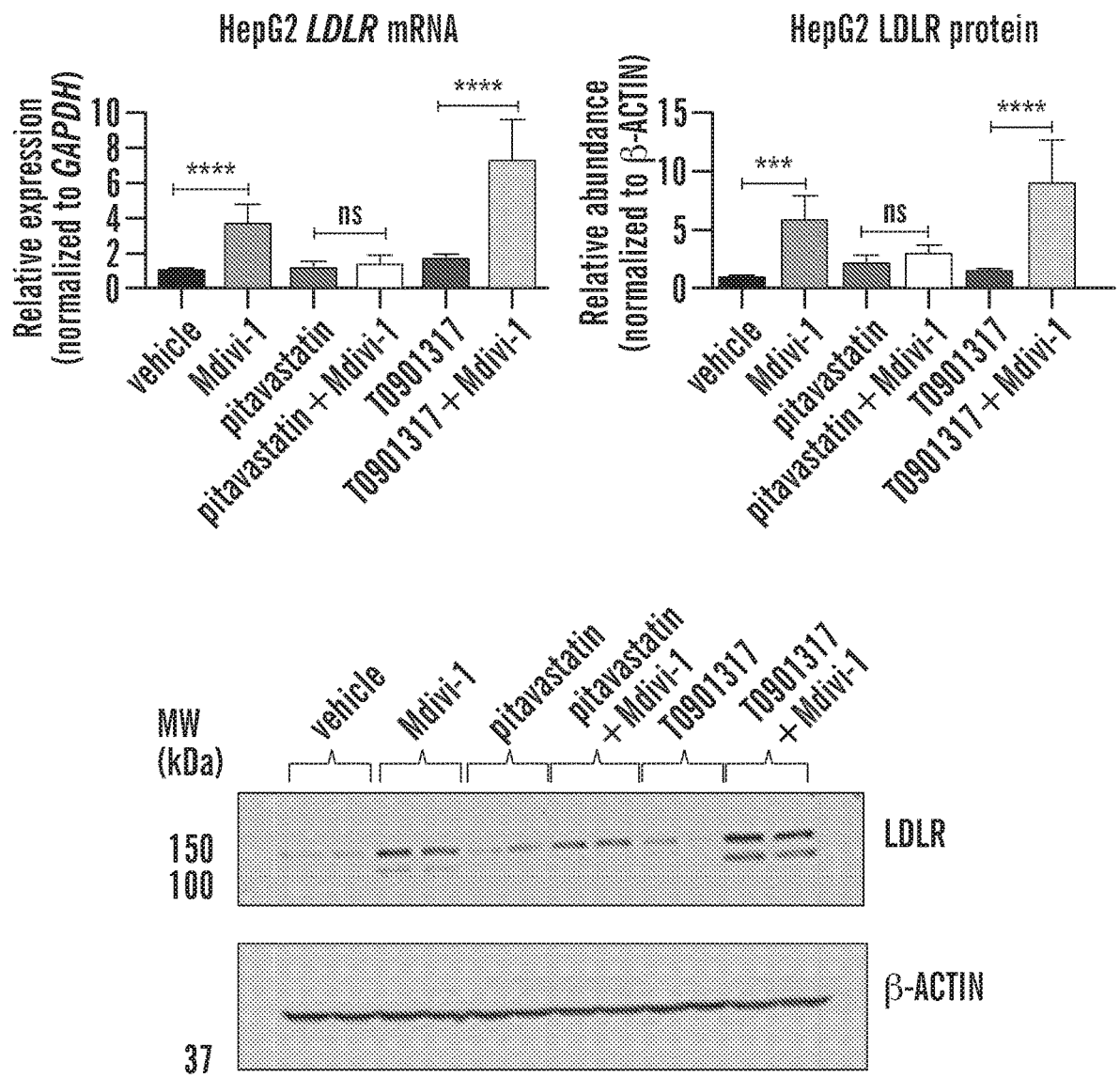
Figure 2C:
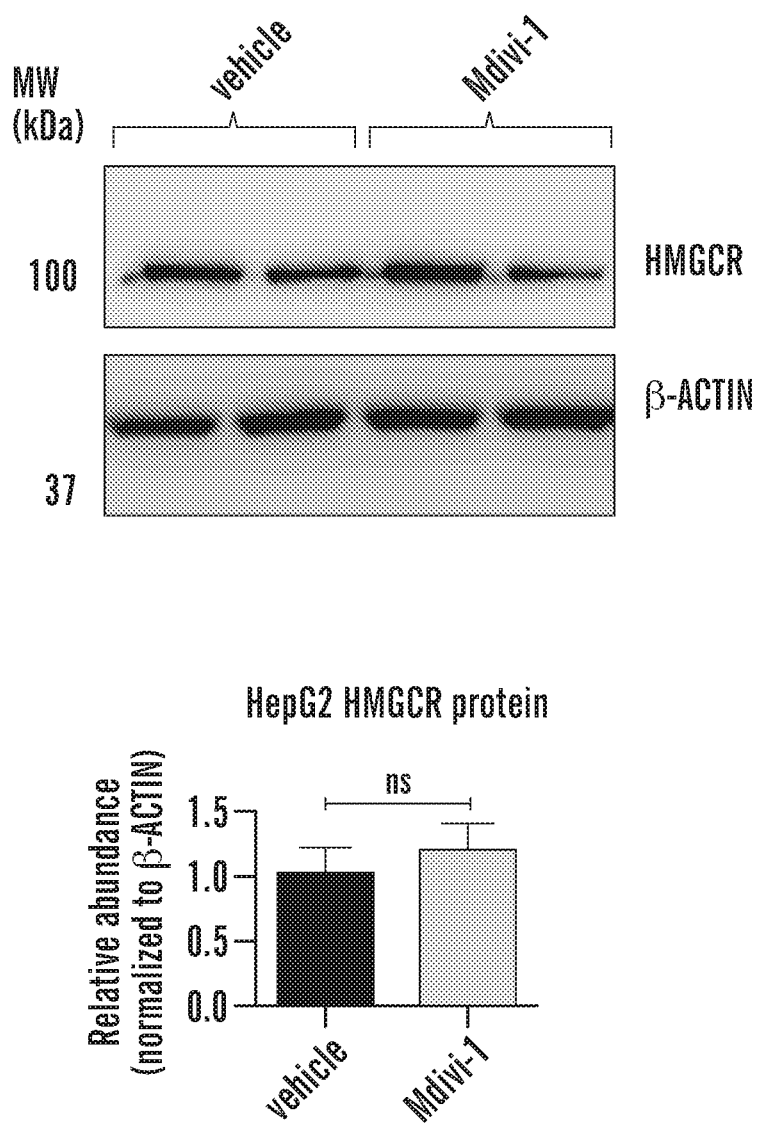
Figure 2D:
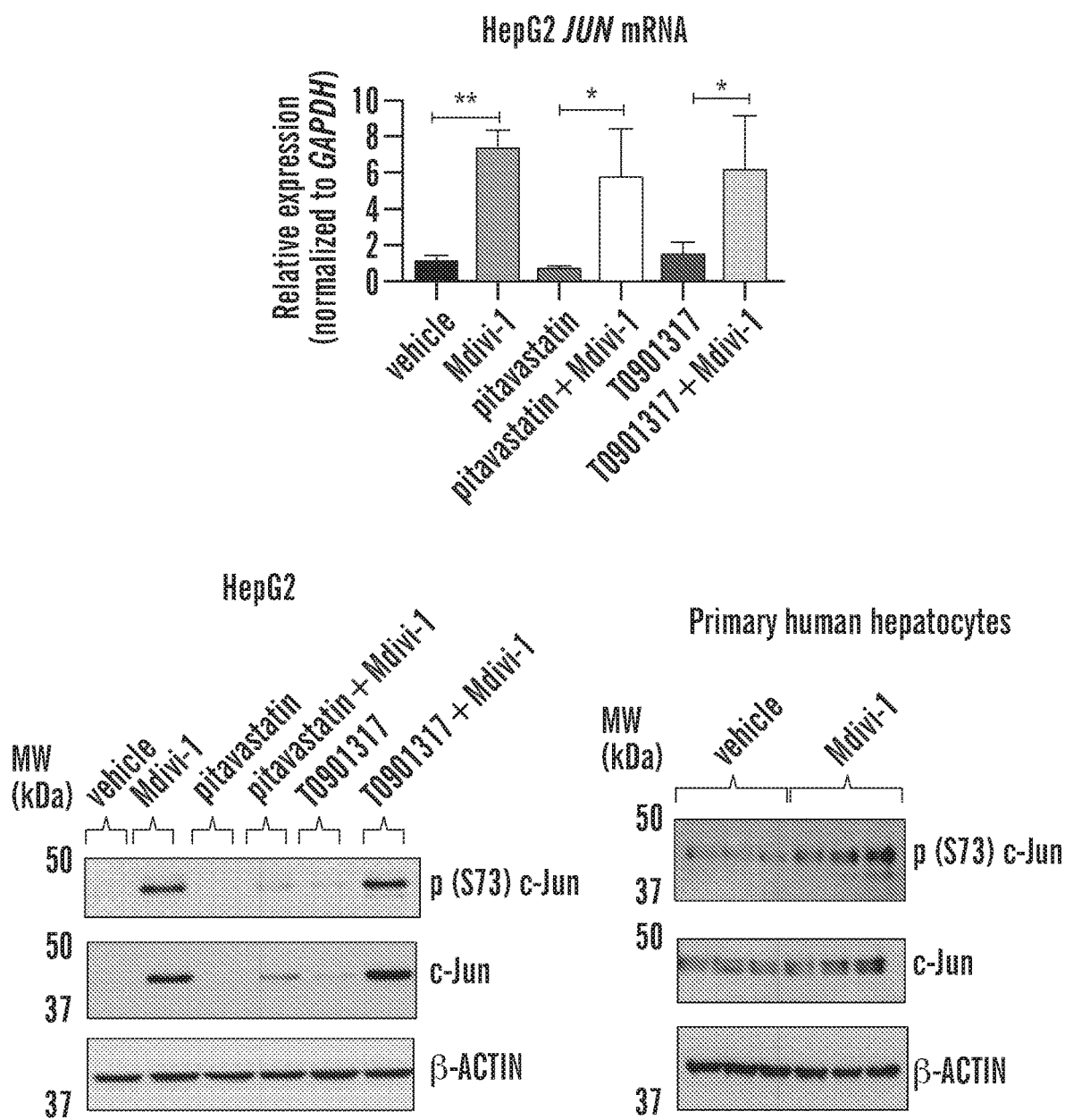

Mdivi-1 increased HepG2 LDLR protein treated alone (5.8-fold), or in combination with pitavastatin (3-fold) or T0901317 (9-fold) (FIG. 2B). As the LDLR protein increase was too large to be explained through PCSK9, LDLR transcriptional regulation was examined. Mdivi-1 increased HepG2 LDLR, but not the abundance of the SREBP target, 3-hydroxy-3-methylglutaryl-CoA reductase (HMGCR) (FIG. 2C), which excluded the LDLR induction from being SREBP mediated. DRP1 inhibition in HepG2, but noticeably much less in primary hepatocytes, increased the phosphorylation and total levels of the cell cycle regulator and LDLR transcriptional activator, c-Jun37. These changes mirrored HepG2 LDLR abundance, and were suppressed by statin treatment, which reduces c-Jun expression[38]. Without wishing to be bound by theory, SREBP response gene differences in HepG2 and primary hepatocytes may be due to cell density/cycle. Primary hepatocytes were obtained as 100% confluent monolayers, whereas HepG2 cells were treated around 60-70% confluency to avoid cell clumping. Again without wising to be bound by theory, as DRP1 inhibition induces cell cycle arrest[39], increased c-Jun may be a cell cycle induction attempt in highly proliferative subconfluent HepG2 cells resulting in increased LDLR expression.

DRP1 Partially Localized at ER in Human Liver Cells

Figure 3A:
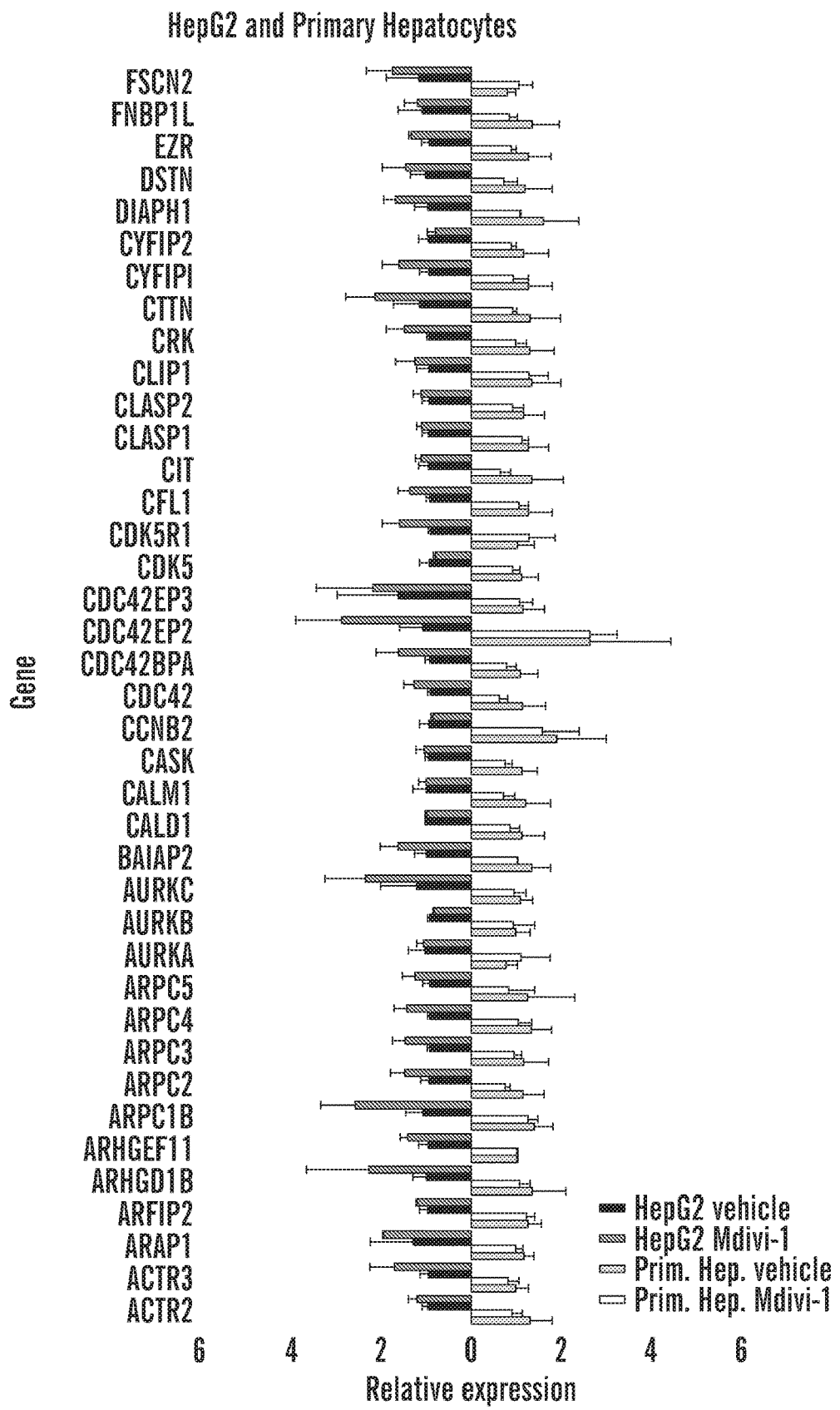
FIGS. 3A-3D DRP1 inhibition did not change human liver cell cytoskeleton or ER morphology, and DRP1 partially localizes to ER in HepG2.
Figure 3A:
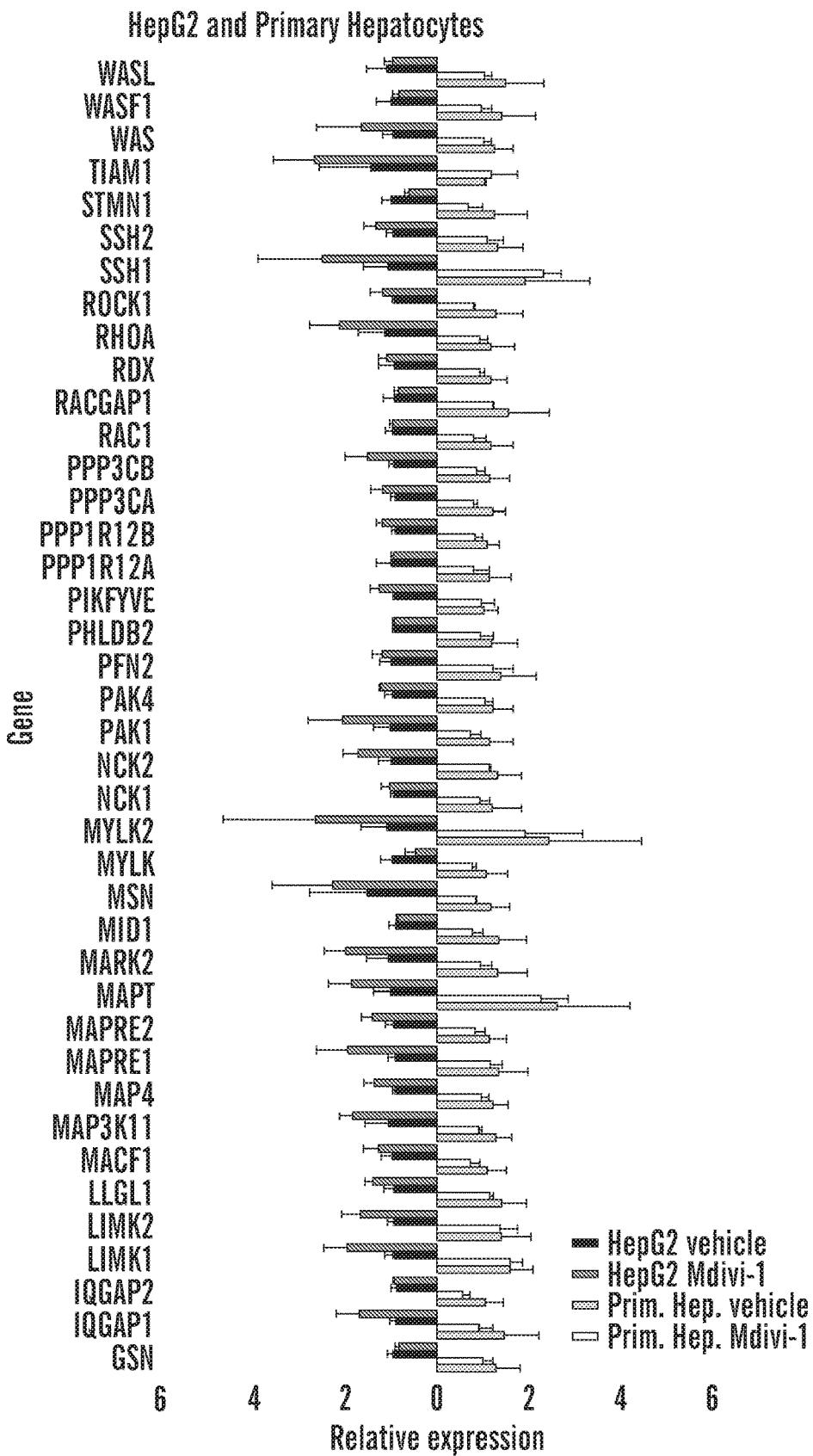
Figure 3B:
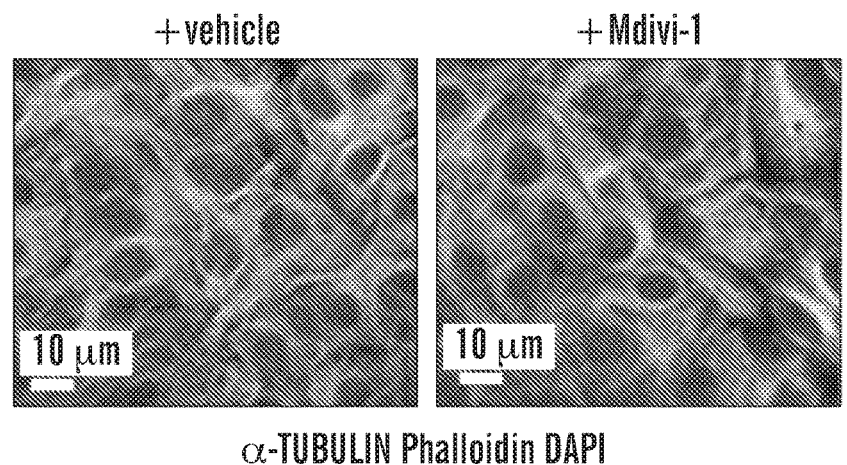
Figure 3C:
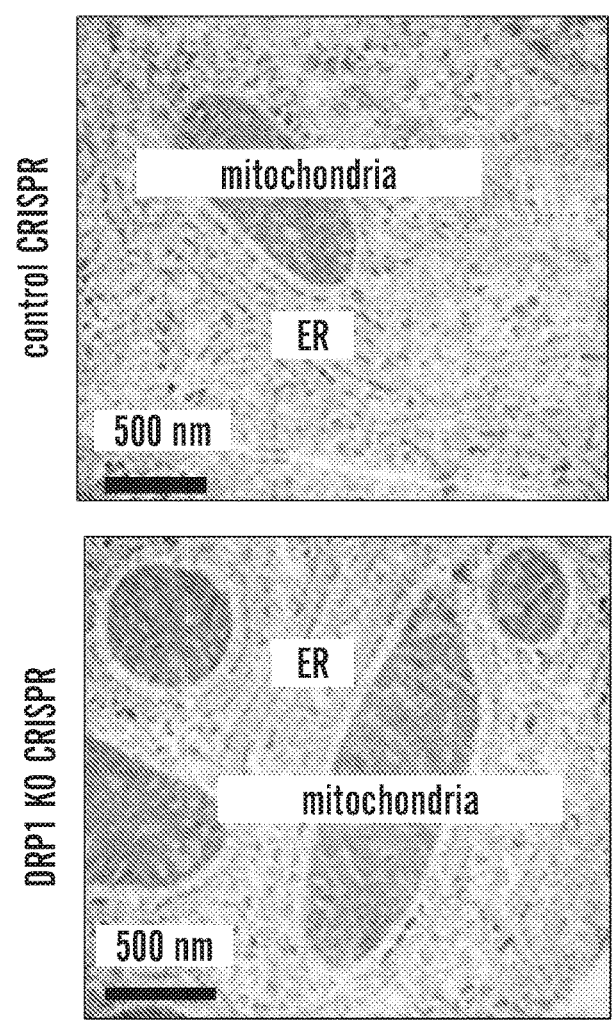
Figure 3D:
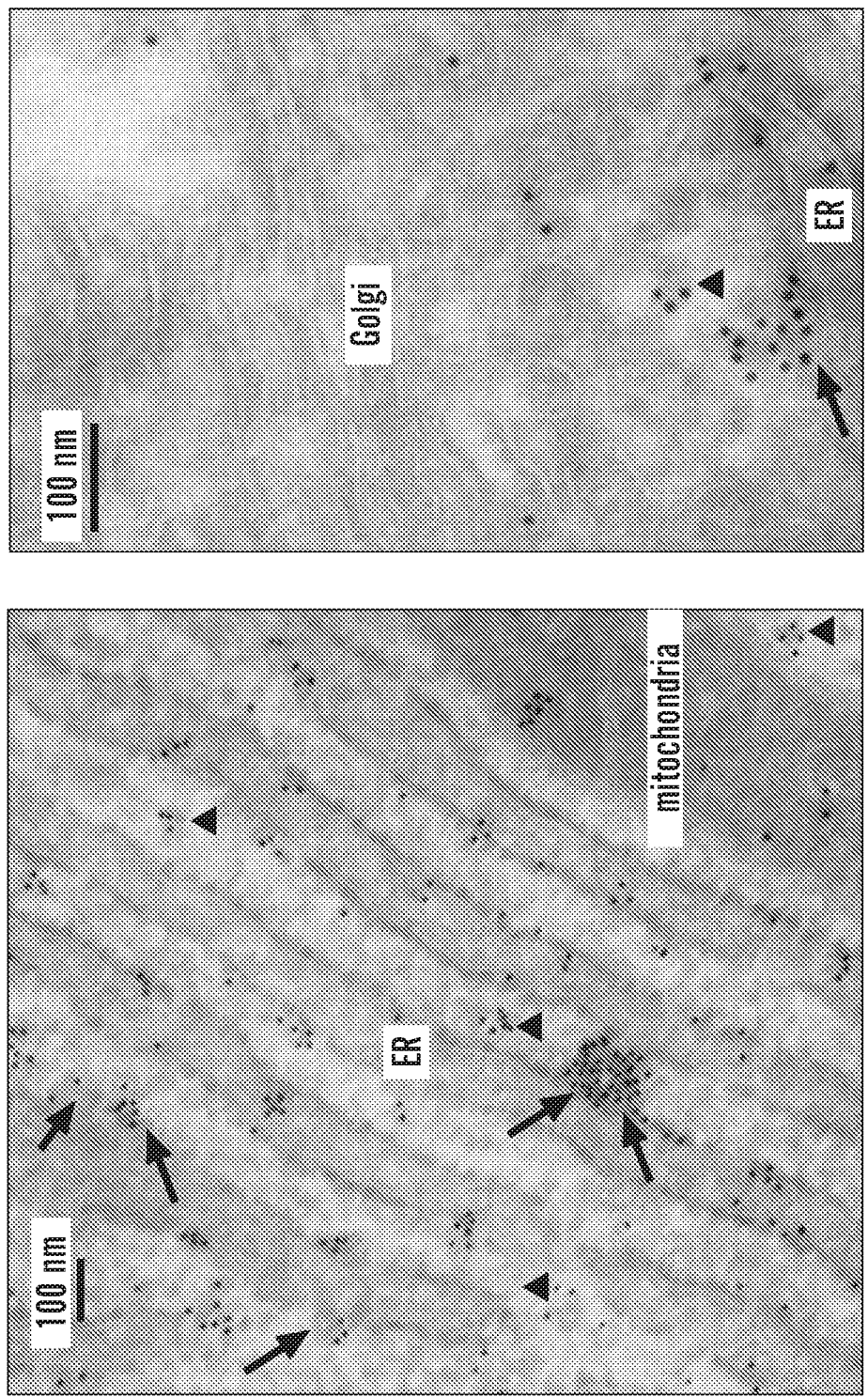
Figure 10A:
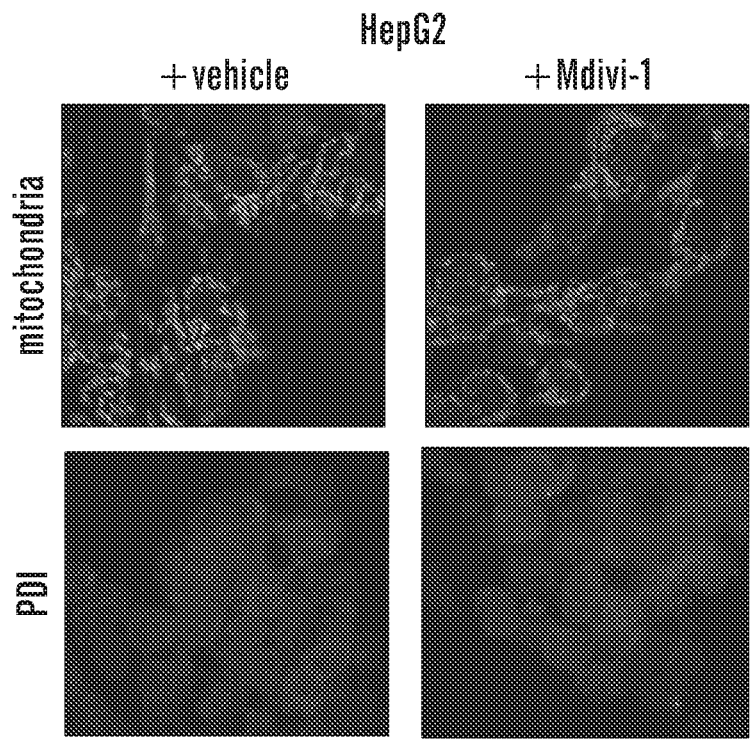
FIGS. 10A-10B Mdivi-1 did not appear to alter mitochondria or ER distribution and mitochondrial membrane potential in HepG2 CELLS.
Figure 10B:
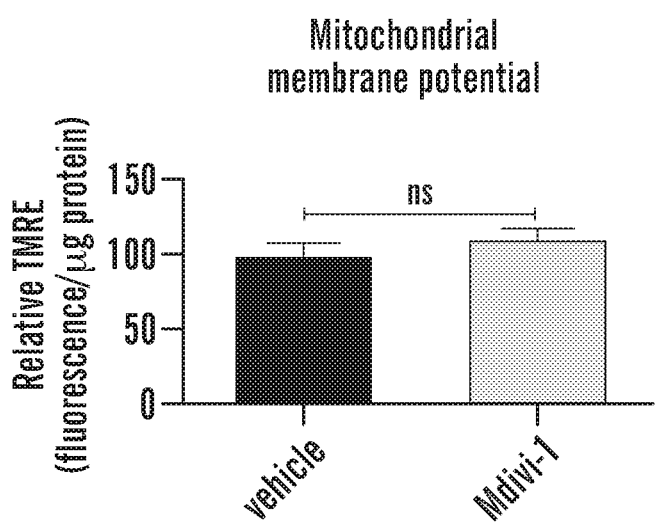

Mdivi-1 treatment did not alter hepatocyte cytoskeleton, as observed by assessing the expression of a panel of cytoskeleton related genes (FIG. 3A), and by actin and microtubule confocal immunofluorescence (FIG. 3B). Liver endoplasmic reticulum (ER) in Drp1LiKO mice appears swollen and dispersed on a high-fat diet, but more like control on normal chow diet[22]. To examine ER morphology in human liver cells, electron microscopy was performed using HepG2 cells in which DRP1 was deleted. HepG2 CRISPR/Cas9 DRP1 knockout cells had no apparent ER morphologic differences compared to control, which appeared as tubular networks alongside mitochondria (FIG. 3C). Mitochondrial function, assessed by mitochondrial membrane potential, and mitochondria and ER localization, viewed by immunofluorescence, was not noticeably different in HepG2 cells treated with Mdivi-1 (FIG. 10). Immunogold electron microscopy was used to assess intracellular DRP1 localization; DRP1 was detected in mitochondria, in the cytosol/cytosolic vesicles, and at the ER, including ER exit sites, while largely absent from the Golgi in HepG2 cells (FIG. 3D).

Mdivi-1 Impaired Autophagic Flux in HepG2

Figure 4A:
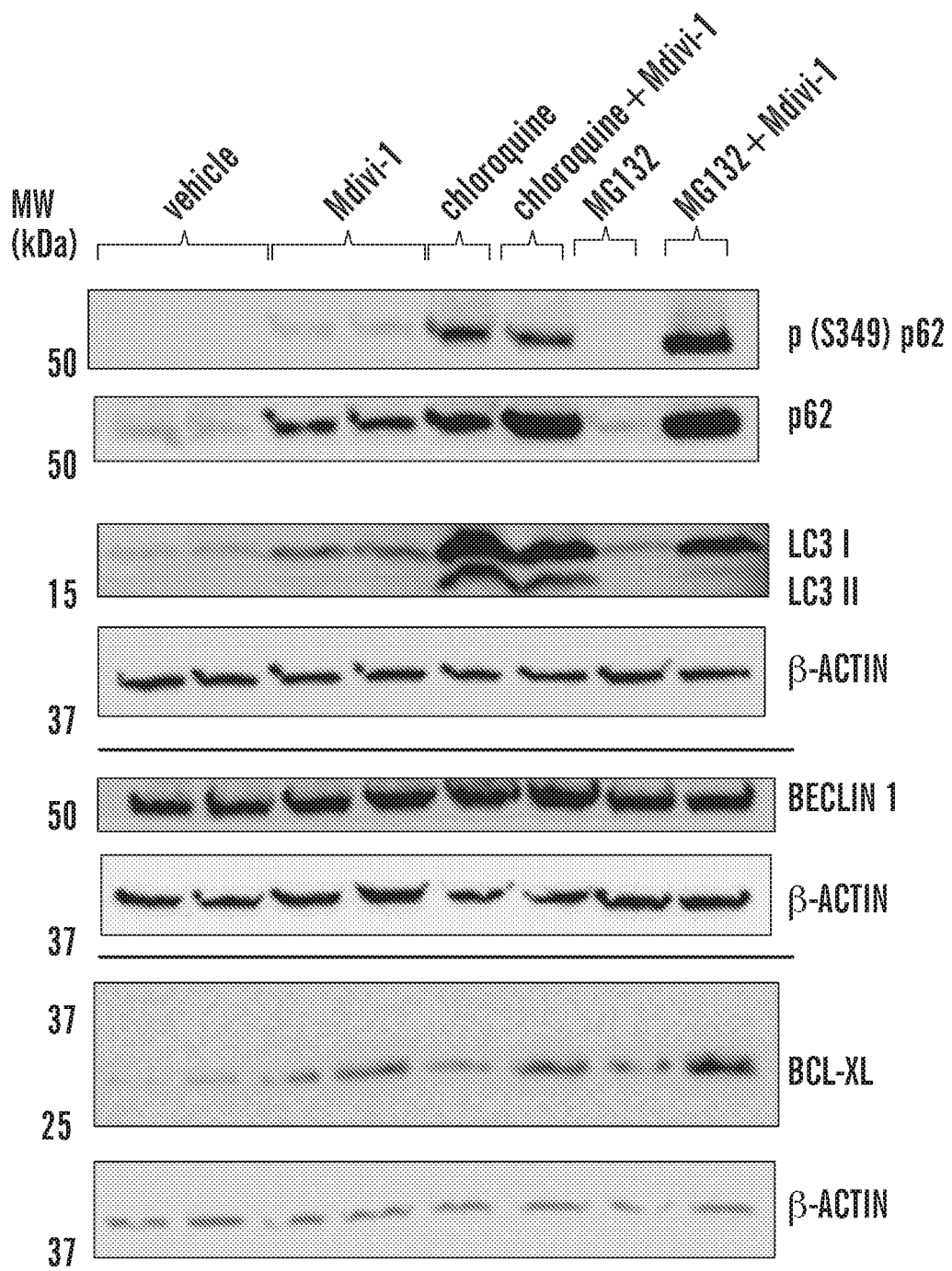
FIGS. 4A-4C Mdivi-1 impairs autophagic flux in HepG2.
Figure 4A:
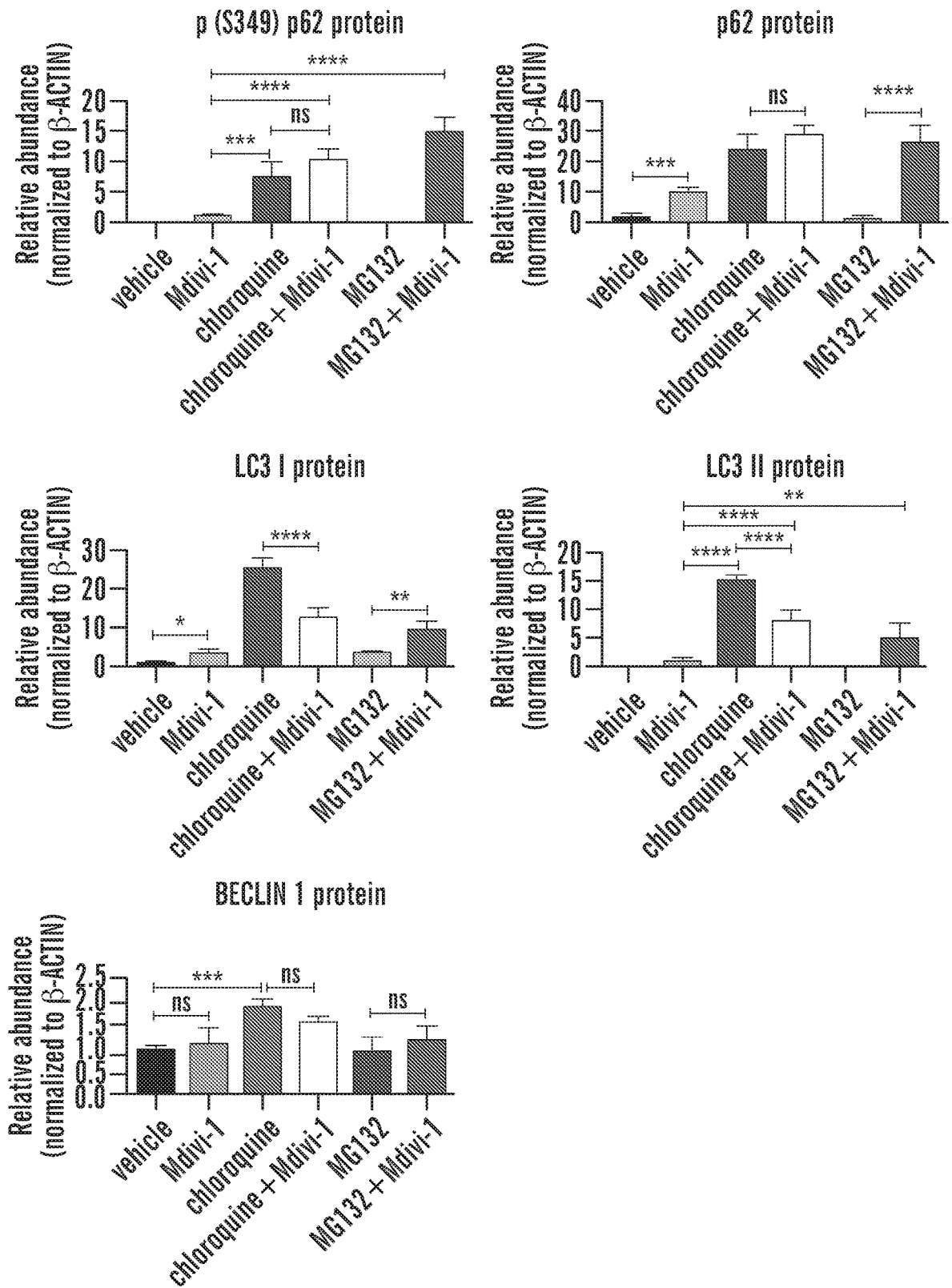
Figure 4B:
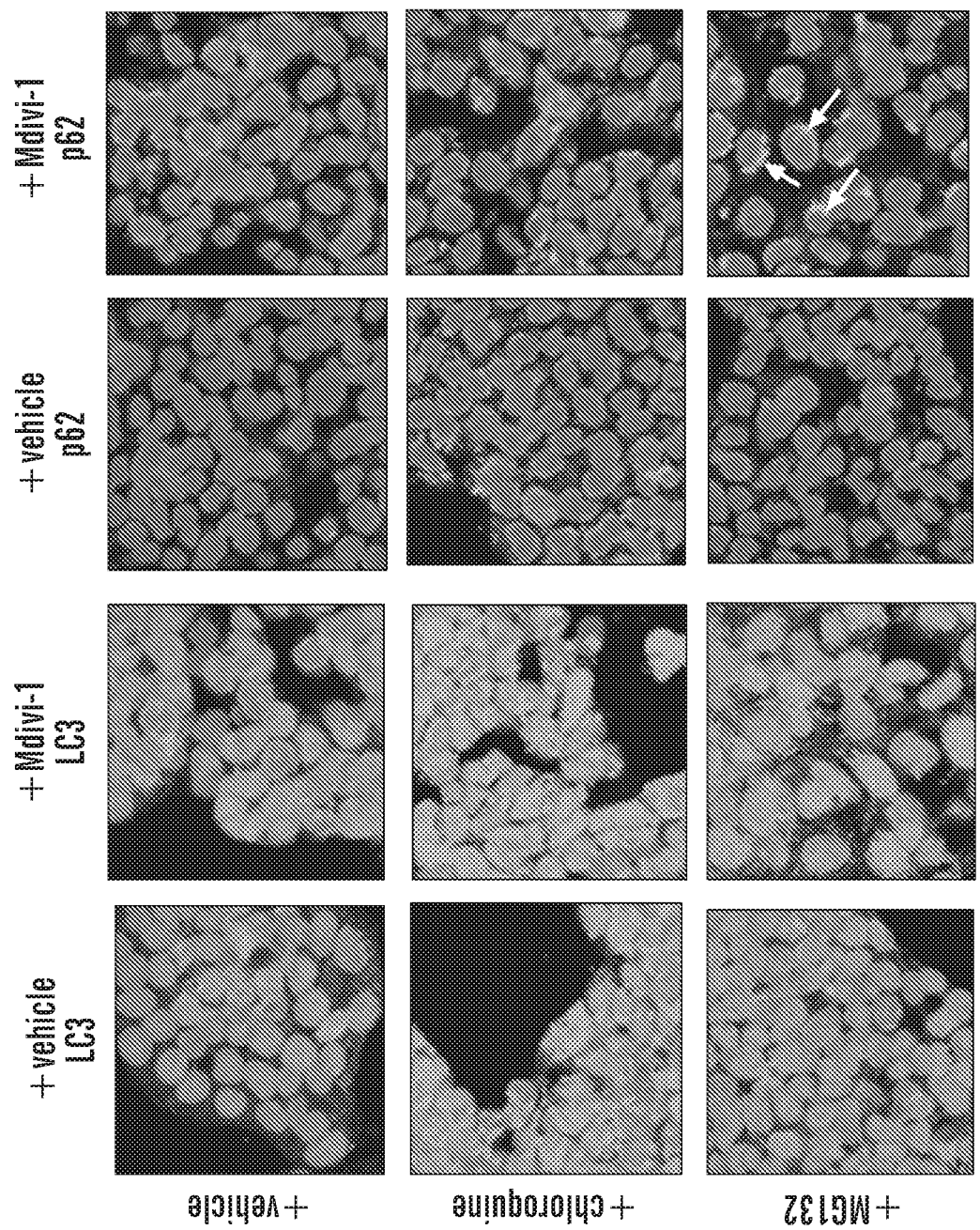
Figure 4C:
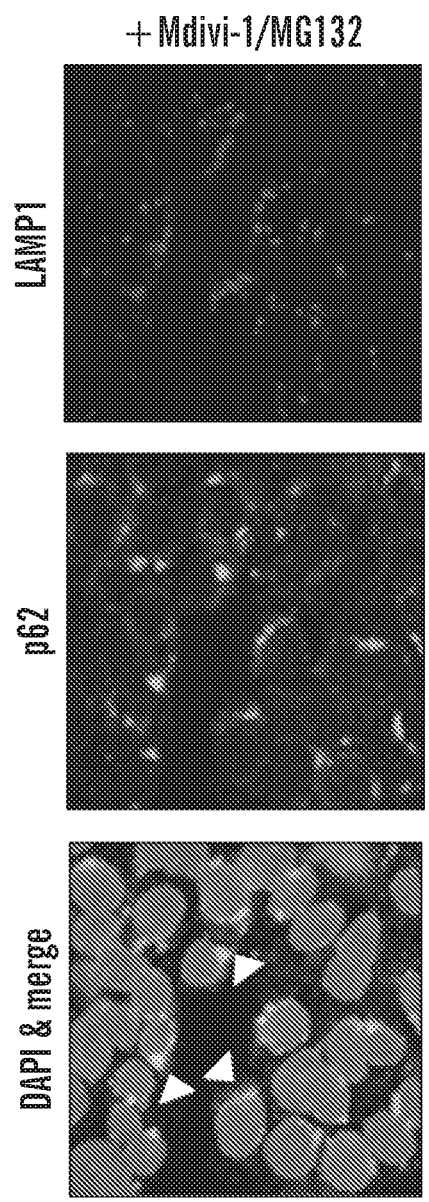
Figure 11A:
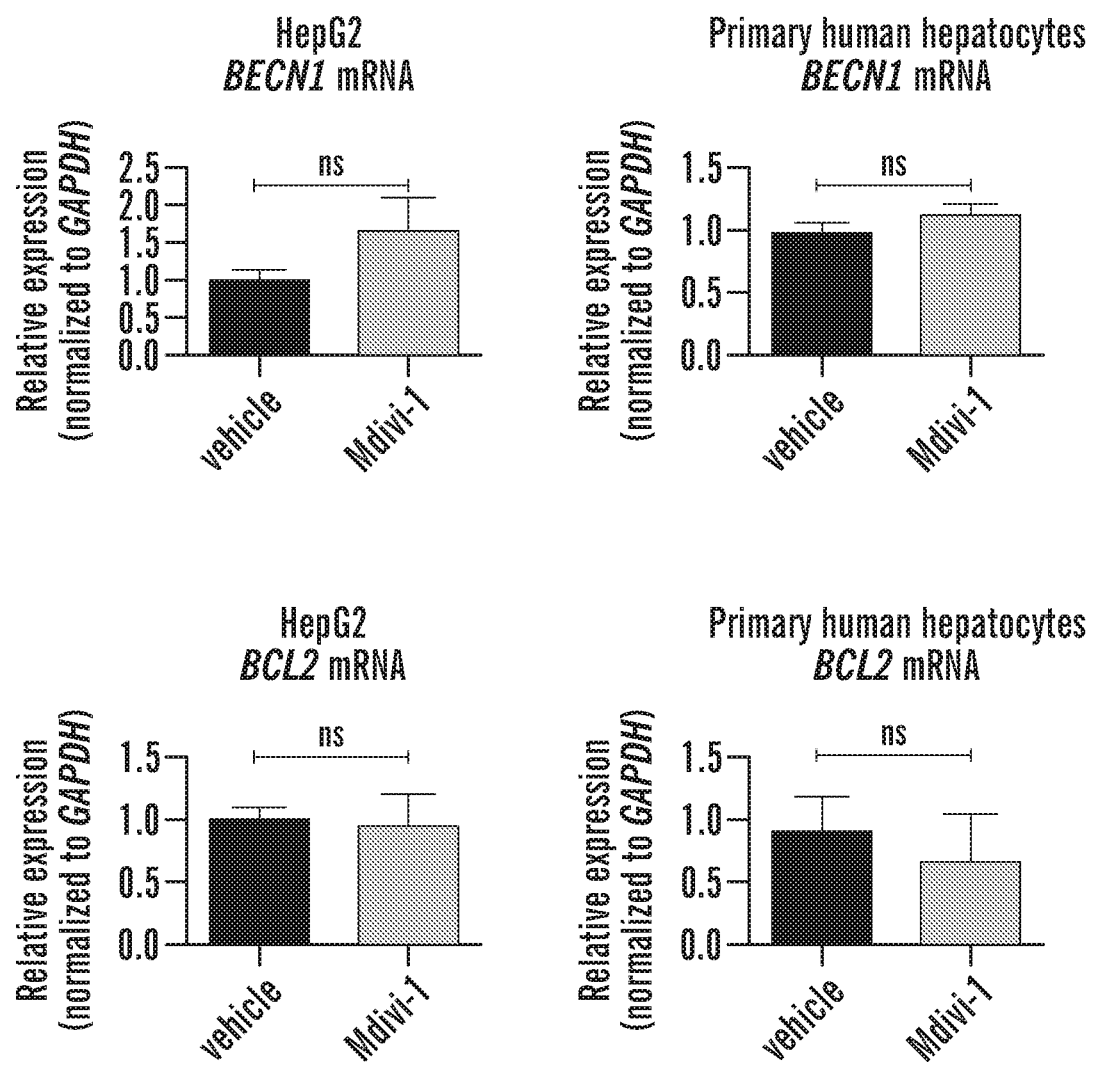
FIGS. 11A-11D HepG2 BCL2 protein was below detection and human liver S9 fraction contained DRP1 and BCL-XL.
Figure 11B:
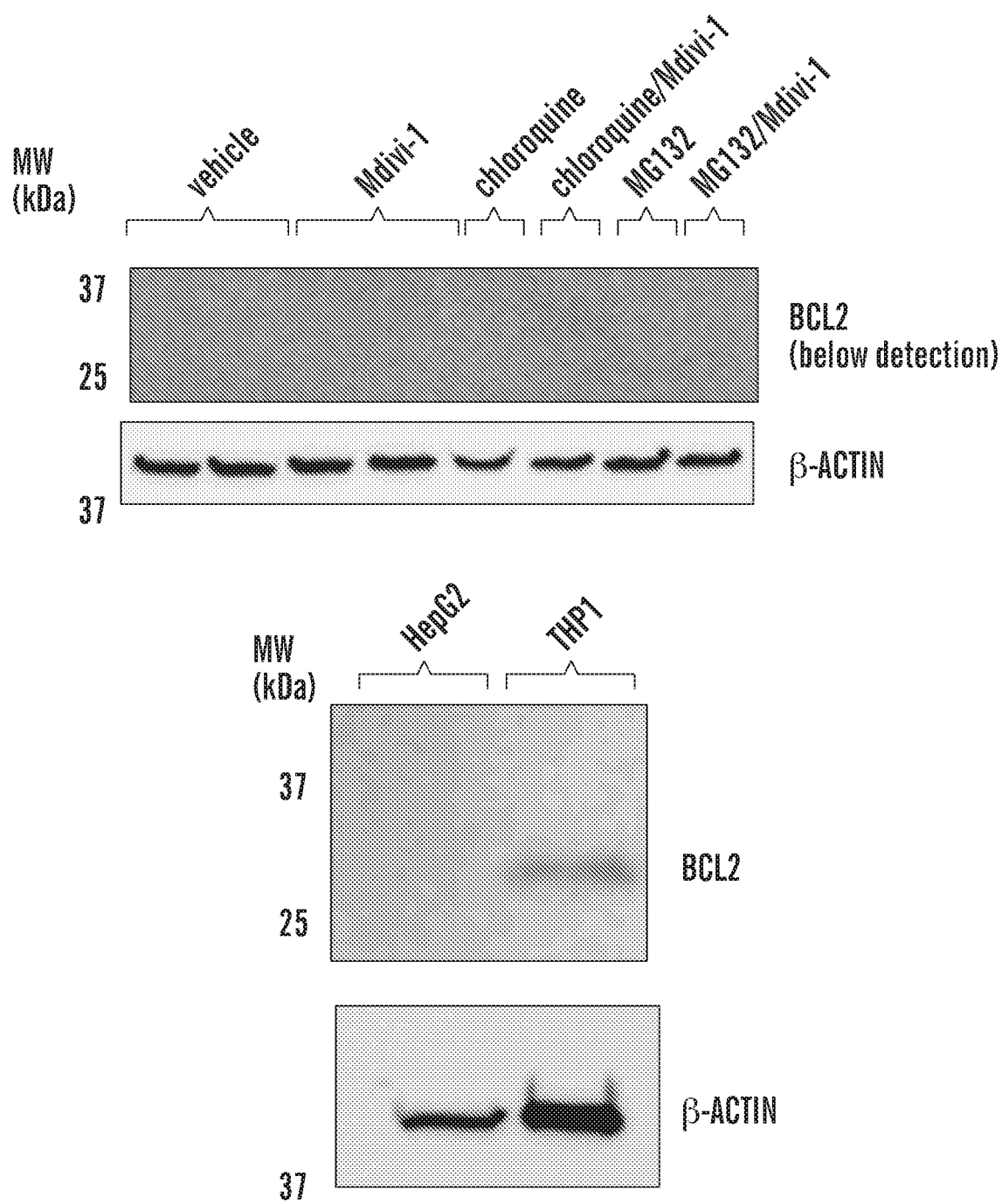
Figure 11D:
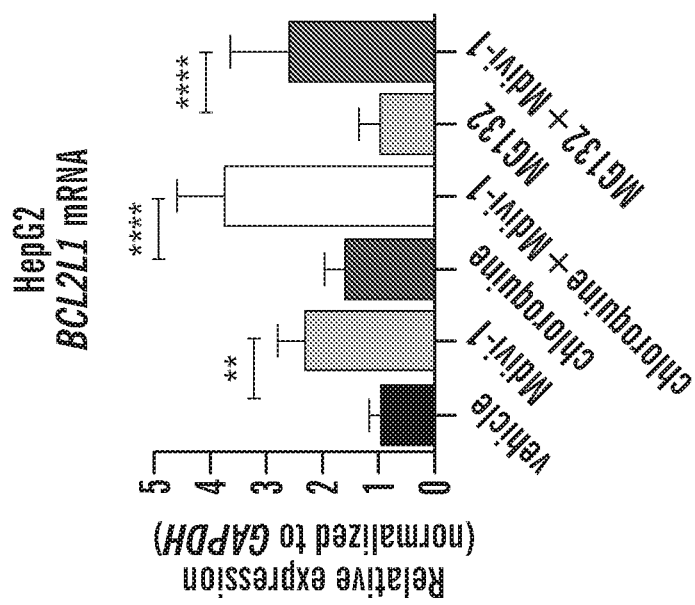
Figure 11C:
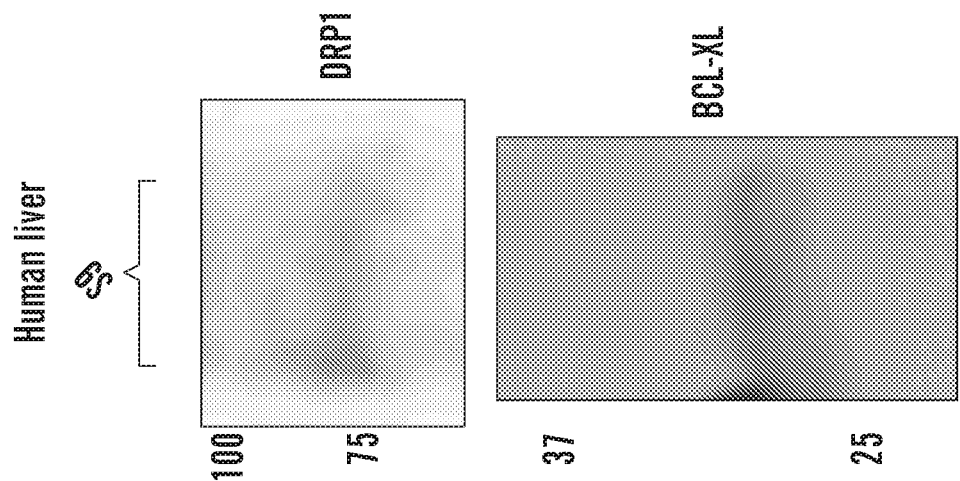

As DRP1 partially localized at ER exit sites, which serve a physical and functional role in autophagosome biogenesis[40] in addition to being the sites for COPII vesicle generation, the effects of DRP1 inhibition on autophagy were assessed. Mdivi-1 strongly increased p62 abundance, and similar to under chloroquine treatment Mdivi-1 increased p62 phosphorylation (FIG. 4A). To assess autophagic flux, HepG2 cells were treated with Mdivi-1 combined with chloroquine. Combined treatment increased light chain 3 (LC3), but to a lesser extent than chloroquine alone (FIG. 4A). Combining Mdivi-1 with a low concentration of the proteasome inhibitor MG132 lead to further increases in phosphorylated and total p62 in addition to LC3 compared to Mdivi-1 or MG132 treatment alone (FIG. 4A). Together these data demonstrate that the Mdivi-1 induced impairment of autophagic flux leads to increased protein clearance through the proteasome. Mdivi-1 did not alter BECLIN1 mRNA, an initiator of autophagosome formation, in human hepatocytes, or HepG2 BECLIN1 protein abundance (FIG. 4A and FIG. 11A). Similarly, mRNA of the BECLIN1 inhibitor, B-cell lymphoma 2 was unchanged in hepatocytes, with its protein level below detection by Western blot in HepG2 cell lysates (FIG. 11A-11B). Pooled human liver S9 fraction, which contains cytosol and ER, from 50 donors contained DRP1 and B-cell lymphoma-extra large (BCL-XL), which also acts to inhibit BECLIN1 assembly of the pre-autophagosomal structure (FIG. 11C). Mdivi-1 increased the expression and abundance of BCL-XL in HepG2 cells (FIG. 11D and FIG. 4A). Immunofluorescence confirmed the Western blot analysis of LC3 and p62 (FIG. 4B), along with revealing that when Mdivi-1 was combined with low levels of MG132, perinuclear lysosomal-associated membrane protein 1 and p62 positive aggregates formed. These data demonstrate Mdivi-1 autophagy impairment in HepG2 leads to proteasomal degradation that when also impaired further alters protein clearance mechanisms to maintain proteostasis.

Drp1 Liver Deficiency Reduced PCSK9 Secretion in Mice

Figure 5A:
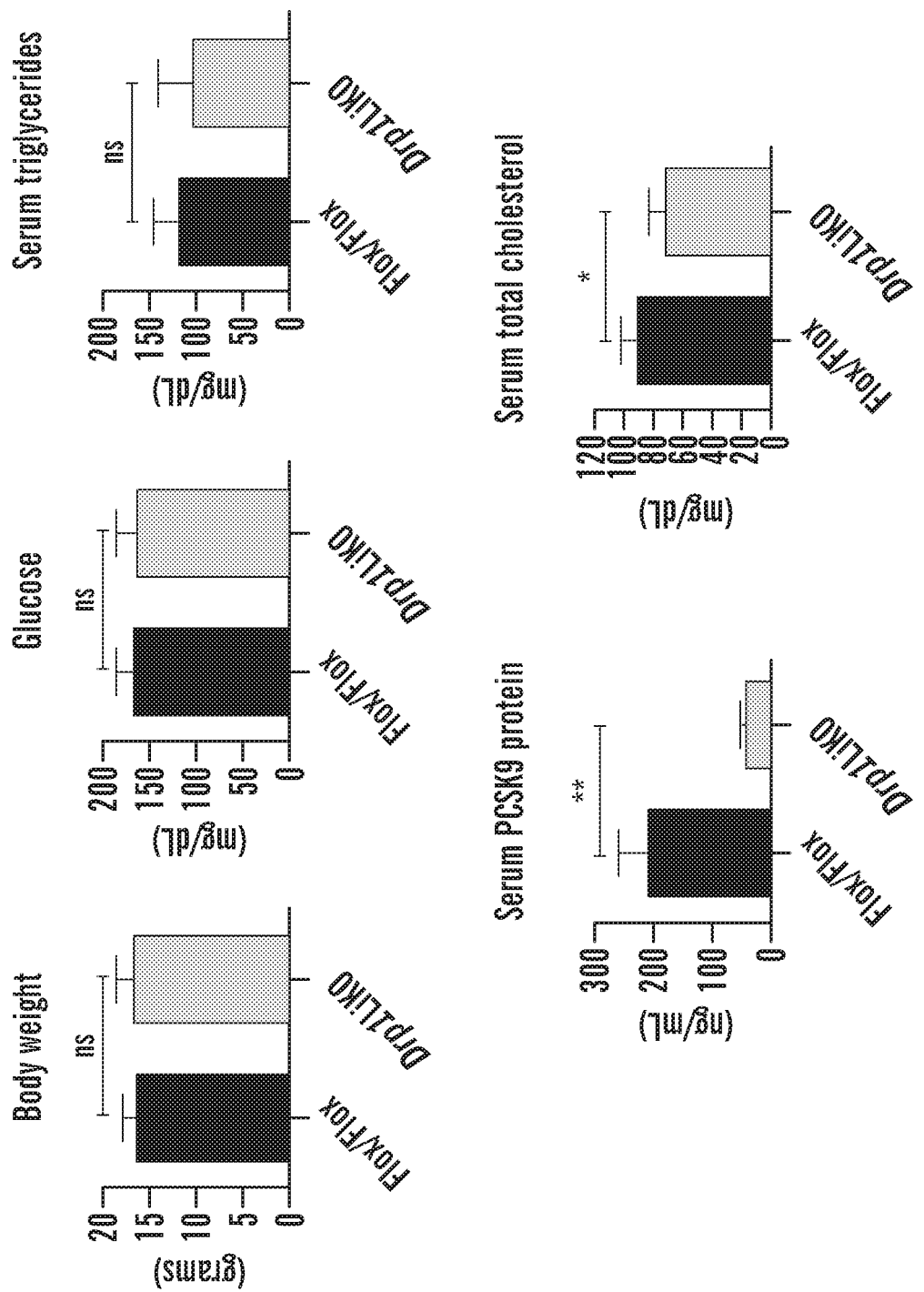
FIGS. 5A-5C Drp1 liver deficiency reduces PCSK9 secretion in mice.
Figure 5B:
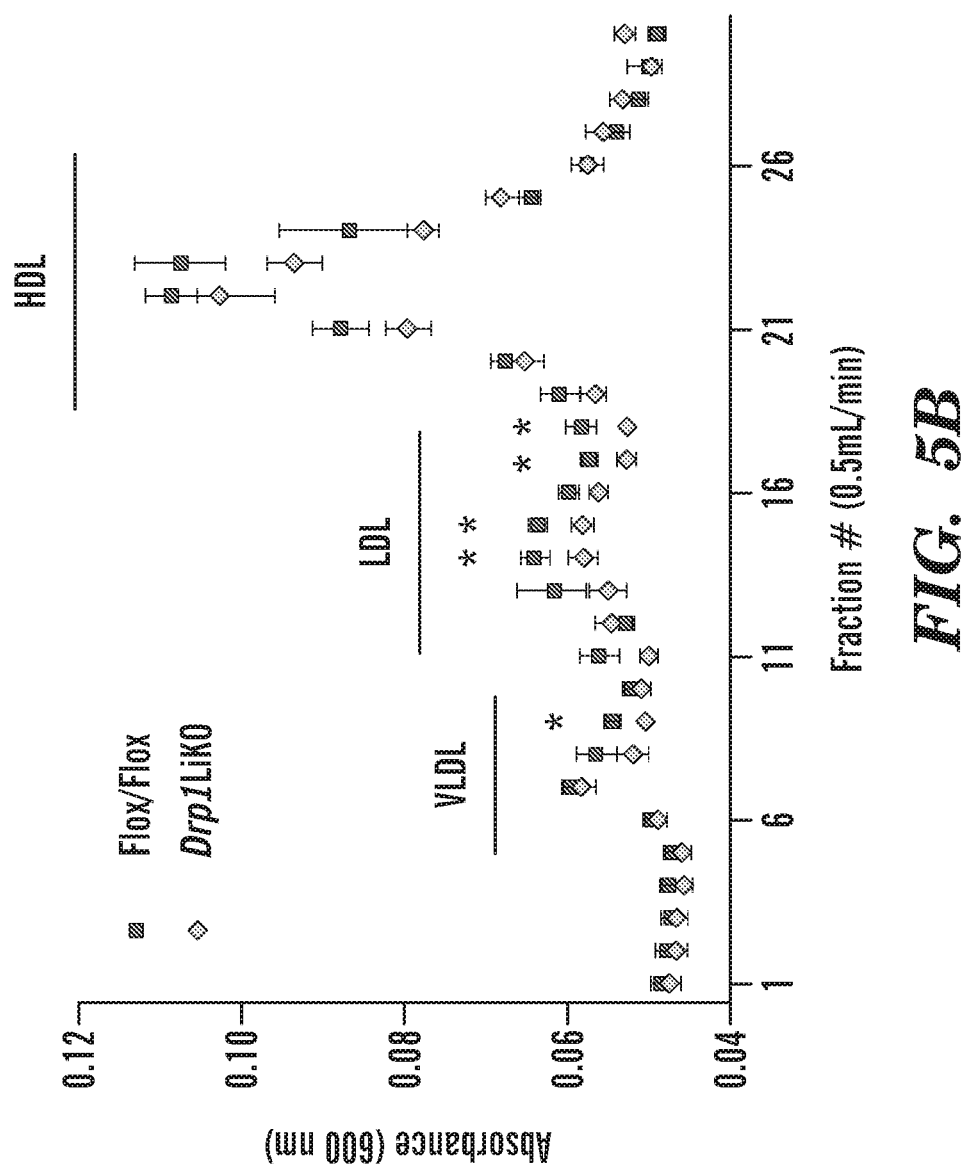
Figure 5C:
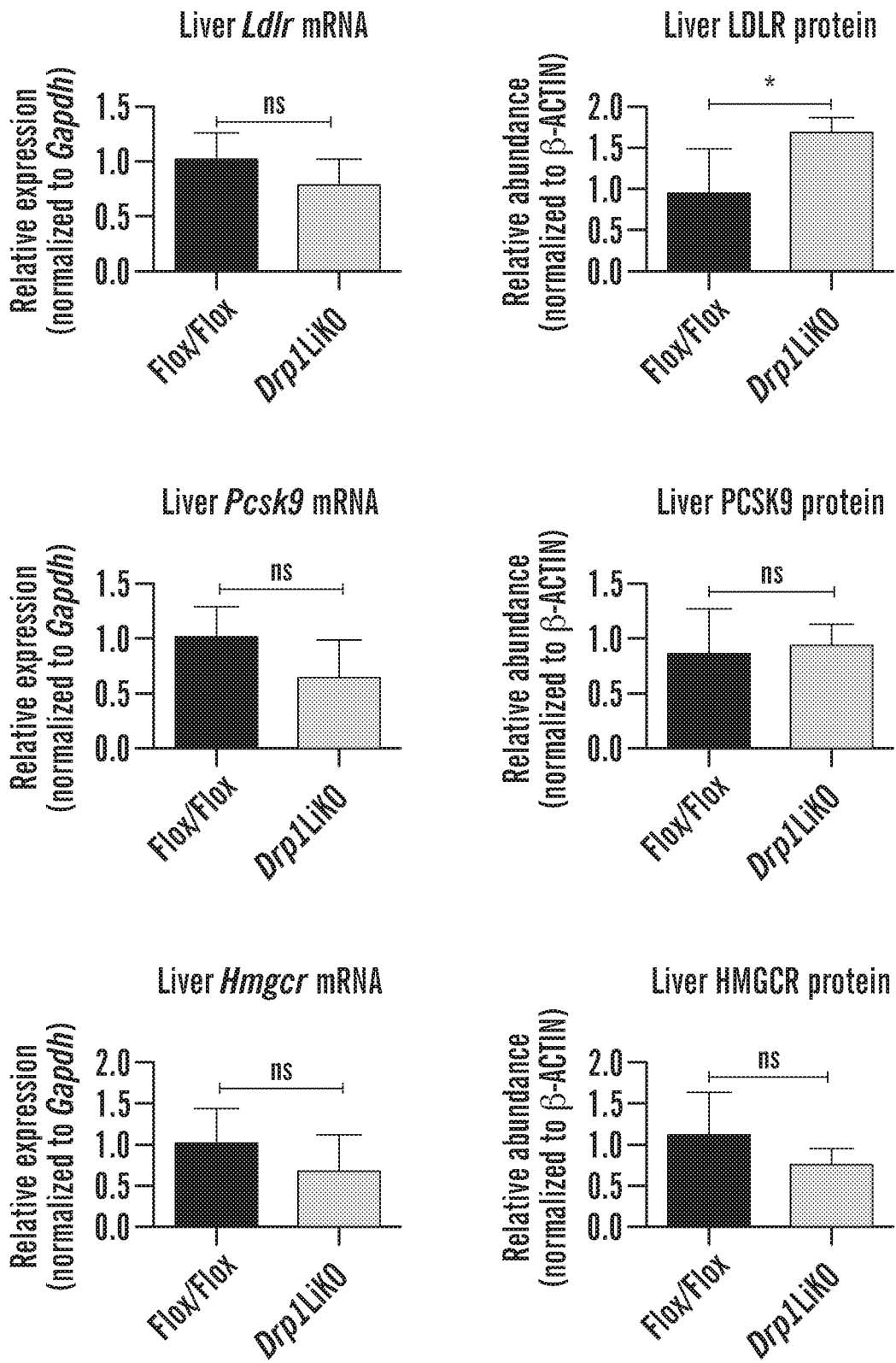
Figure 5C:
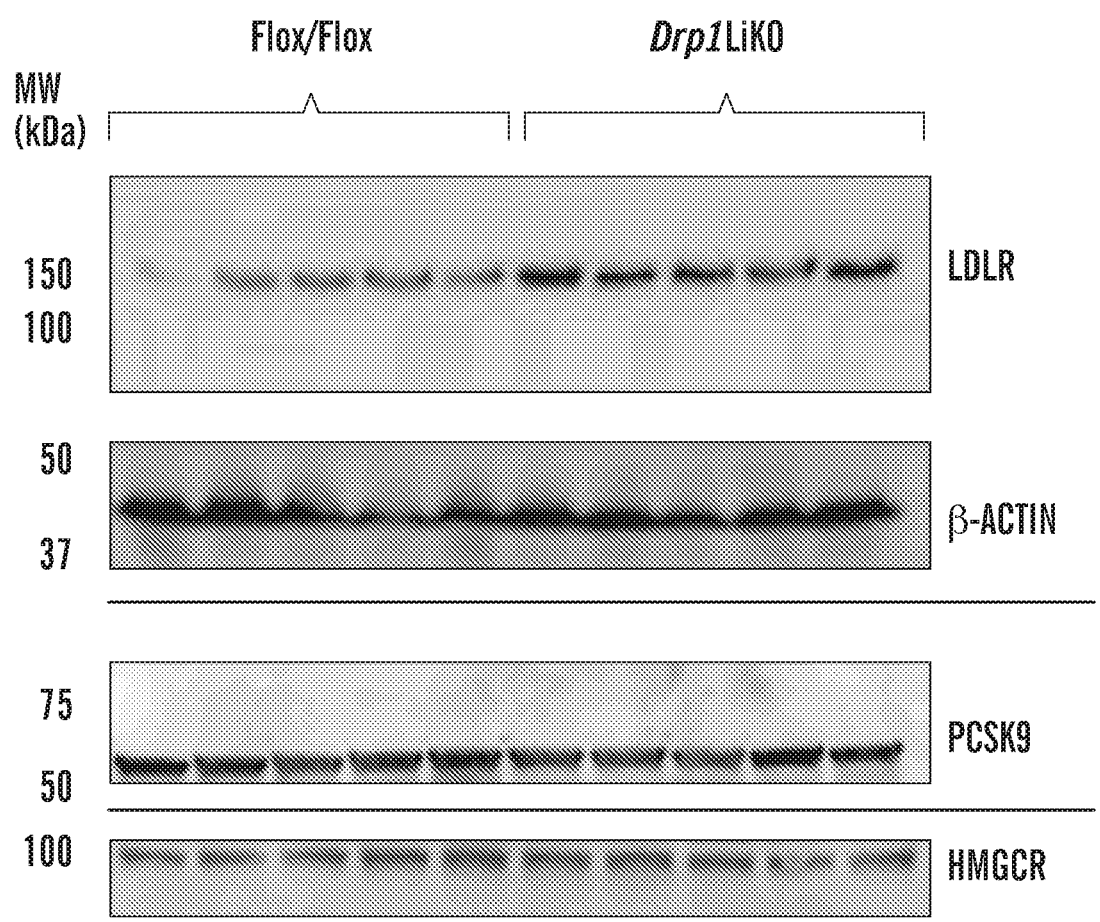
Figure 6A:
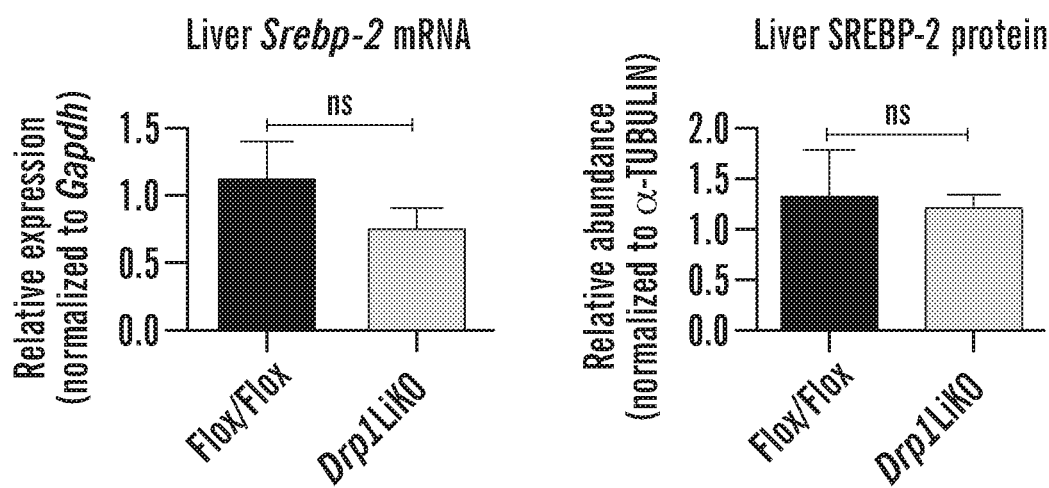
FIGS. 6A-6C Drp1 liver deficiency does not alter mouse liver SREBP.
Figure 6A:
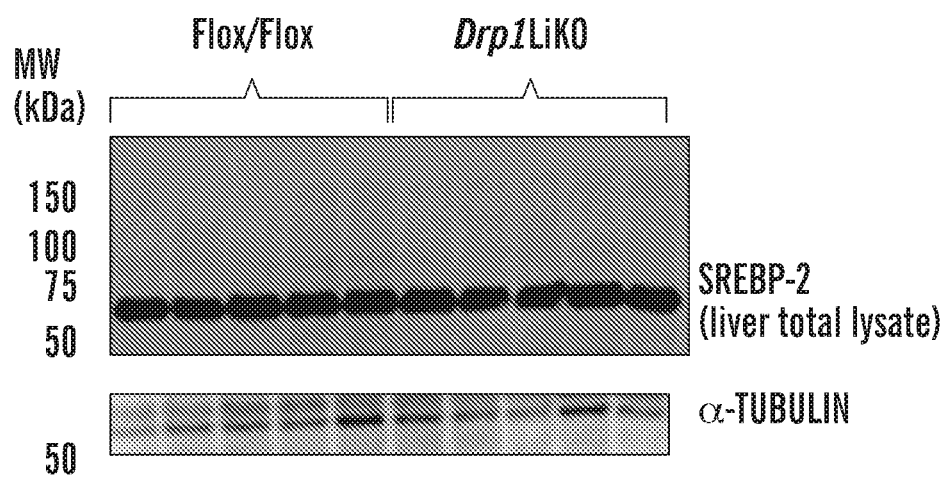
Figure 6A:
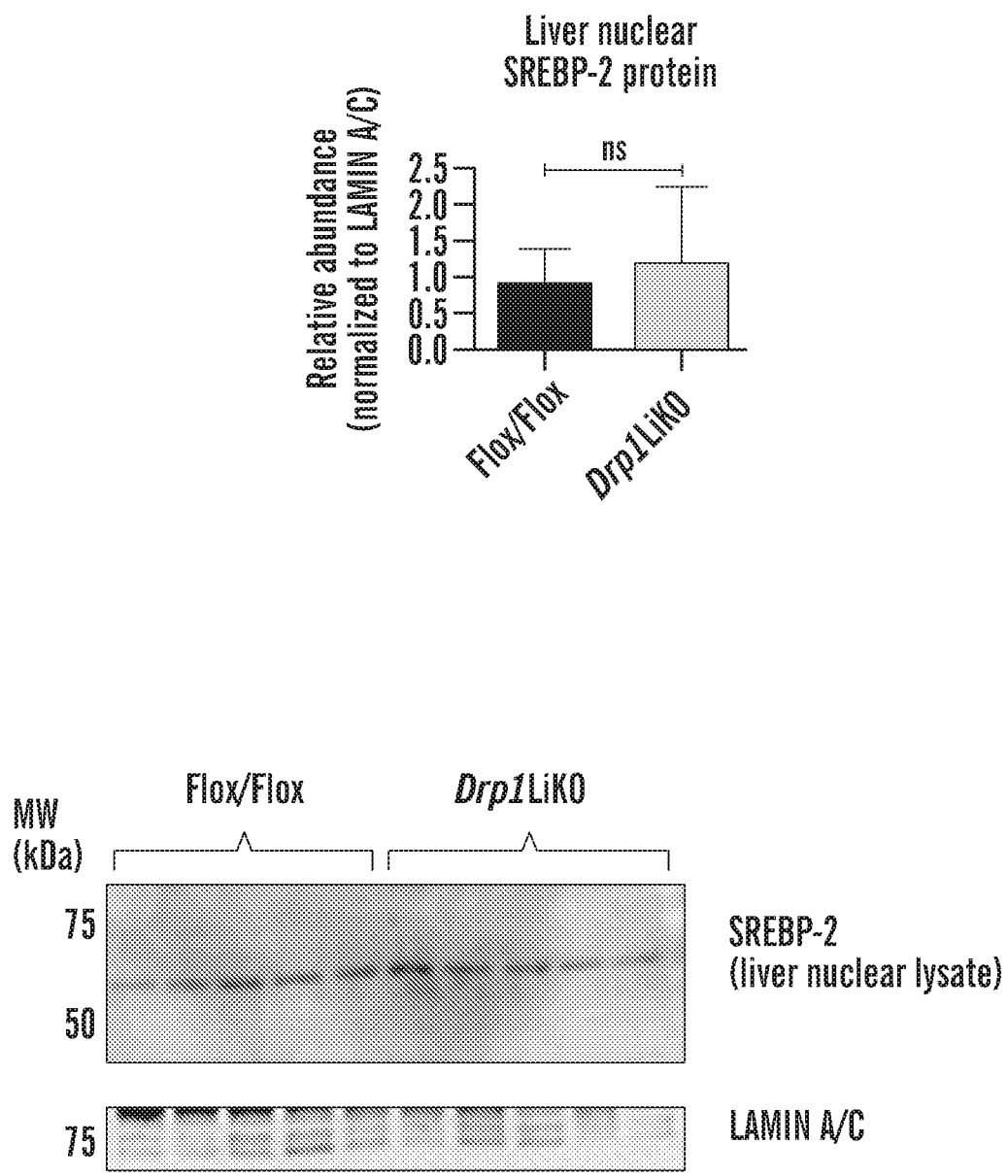
Figure 6B:
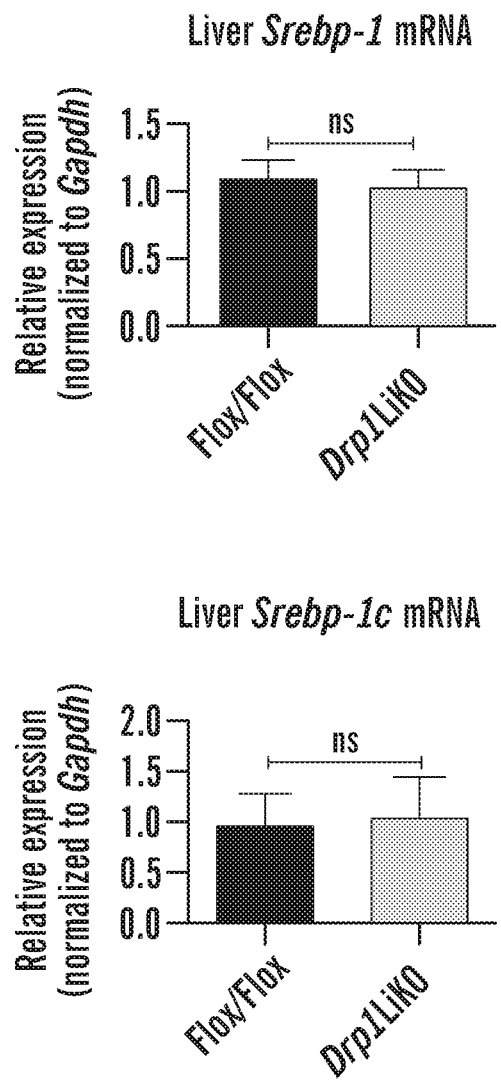
Figure 6B:
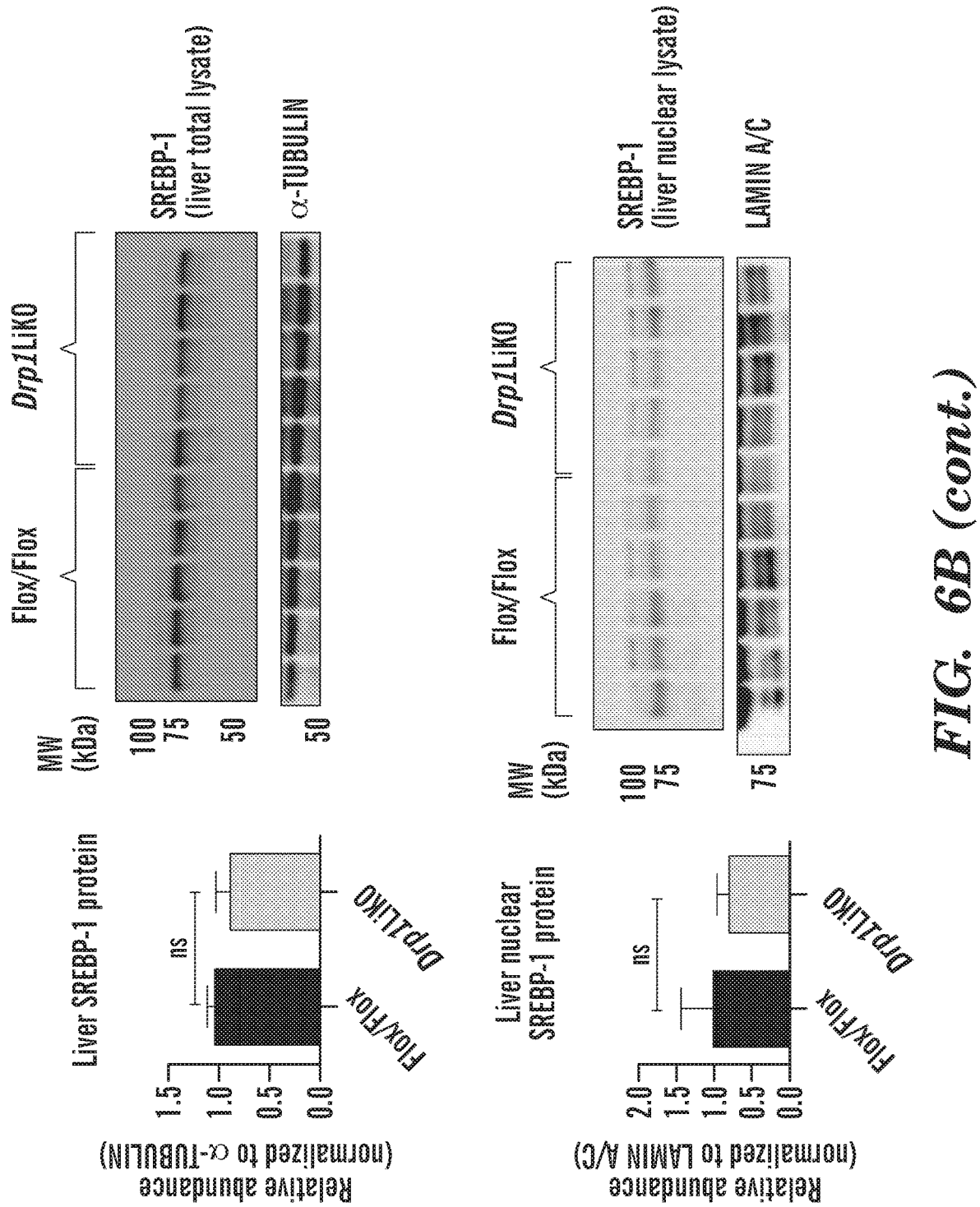
Figure 6C:
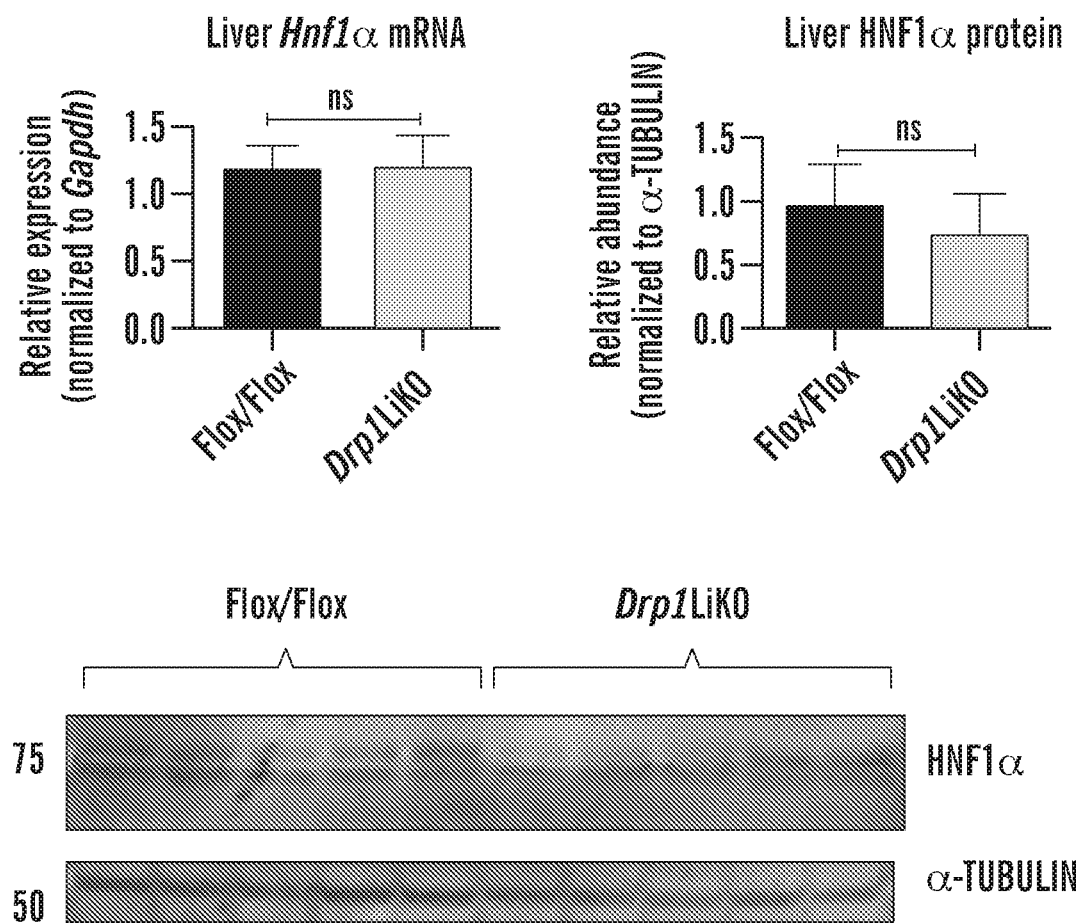

To test the role of DRP1 on hepatic PCSK9 secretion in vivo, Drp1LiKO mice that are deficient in liver DRP1 were used. 1-month-old male Drp1LiKO mice on a normal chow diet had reduced serum PCSK9 (−78.5%) compared to Flox/Flox controls (FIG. 5A), providing in vivo confirmation that inhibiting DRP1 reduces PCSK9 secretion. Body weight, glucose, and triglycerides were unchanged in these experimental conditions (FIG. 5A). Total cholesterol (−21%) and LDL fractions, observed by complete lipoprotein profiling of serum, modestly but significantly decreased in Drp1LiKO mice on a chow diet (FIGS. 5A and B). Liver HMGCR and PCSK9 protein and mRNA levels in Drp1LiKO were not significantly different whereas liver LDLR protein but not mRNA increased (FIG. 5C). Total and nuclear liver SREBP (FIGS. 6A and B) and HNF1A (FIG. 6C) protein and mRNA were unchanged in Drp1LiKO (FIGS. 6A and B).

Drp1 Liver Deficiency Increased p62 in Mouse Liver

Figure 7A:
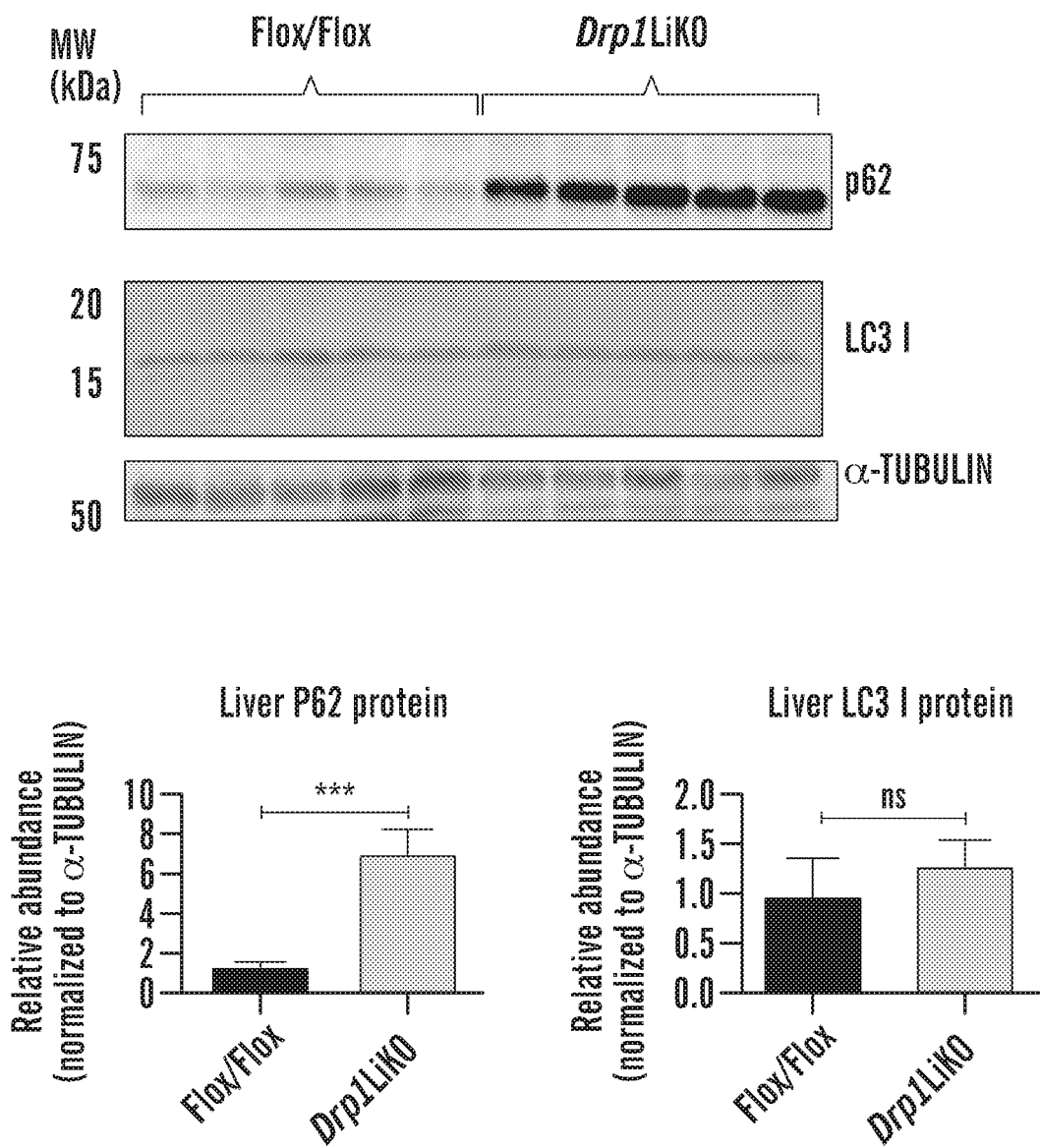
FIGS. 7A-7B Drp1 liver deficiency increases p62 in mice.

To assess whether the proteostasis alterations observed following Mdivi-1 treatment of human liver cells also occurred in vivo, p62 abundance was measured in the liver of non-fasted Drp1LiKO mice on a chow diet. Drp1LiKO increased liver p62 without significantly altering LC3 abundance (FIG. 7A), supporting a similar alteration in proteostasis.

Figure 7B:
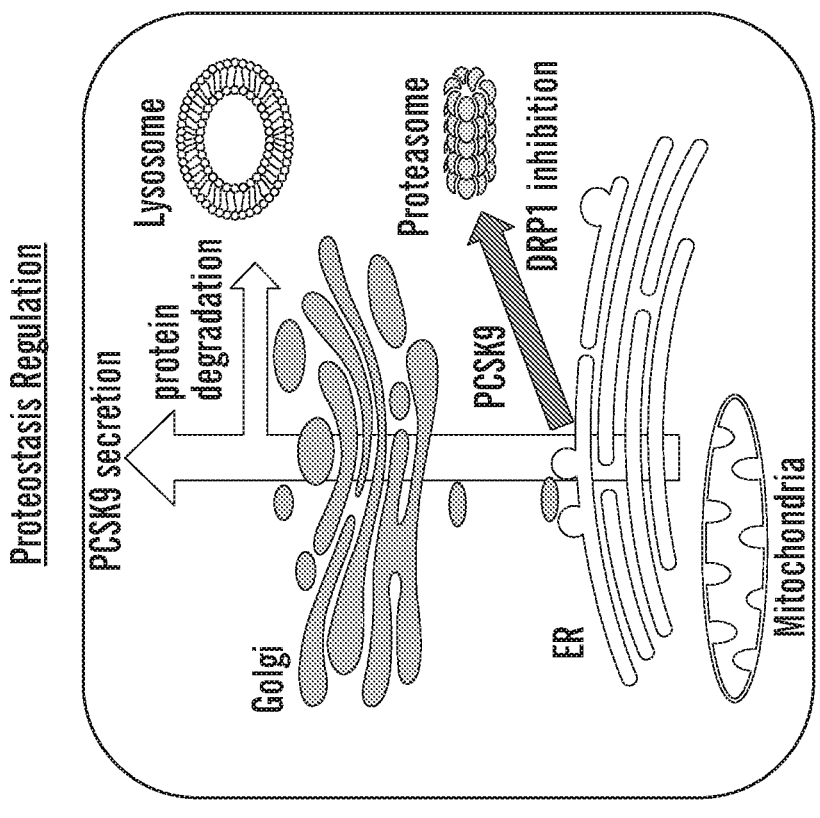
Figure 7B:
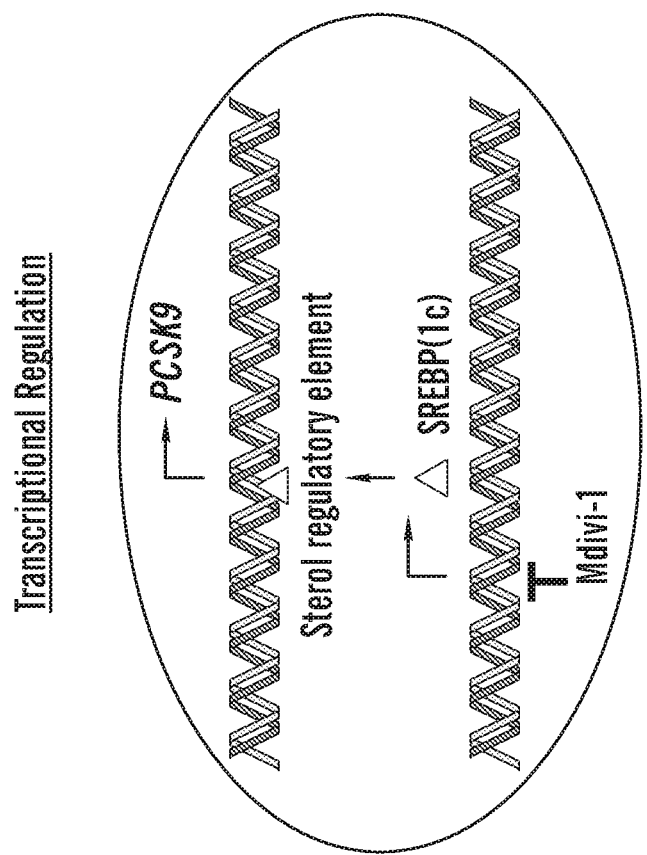

This study reports the following novel findings: (1) DRP1 inhibition via Mdivi-1 or CRISPR/Cas9 gene knockout in human liver cells, and Drp1 knockout in mouse liver reduces PCSK9 secretion; and (2) hepatic DRP1 inhibition alters proteostasis by impairing autophagic flux and inducing protein clearance through the proteasome. Without wishing to be bound by theory, presented herein is a working model involving both transcriptional and trafficking mechanisms to explain the findings of the present study (FIG. 7B). Transcriptional regulation may occur in select conditions where Mdivi-1 reduces PCSK9 expression by downregulating the transcription factor SREBP-1c. While Mdivi-1 reduced SREBP-1c in both HepG2 and primary human hepatocytes, PCSK9 mRNA was only reduced in HepG2; as such, SREBP-1c regulation of PCSK9 may occur under select metabolic-related conditions[36]. Further supporting metabolic regulation, in the present study Drp1LiKO chow fed mice did not have reduced liver SREBP-1c expression, whereas these mice have reduced SREBP-1c on high fat diet[22]. DRP1 inhibition did not alter SREBP-1a or SREBP-2 in the experimental conditions of the present study, which may act as dominant SREBP transcriptional regulators of PCSK9 in cases where reduced SREBP-1c did not suppress PCSK9. As PCSK9 secretion was reduced by DRP1 inhibition in HepG2, primary hepatocytes, and mice, these findings could not be entirely explained through transcriptional regulation. DRP1 inhibition may more broadly reduce PCSK9 secretion through regulation of trafficking and cellular proteostasis.

Mdivi-1 treatment combined with a low amount of the proteasome inhibitor MG132 led to intracellular pro-PCSK9 accumulation when compared to Mdivi-1 or MG132 treatment alone in HepG2 cells. The buildup of the ER precursor pro-PCSK9 form indicates that DRP1 inhibition responds to reductions in PCSK9 secretion, possibly mediated by alterations of ER-related processes like autophagy, by increasing PCSK9 degradation via the proteasome. PCSK9 secretion requires ER-to-Golgi trafficking[9]. As DRP1 inhibition in human liver cells and mice did not suppress LDLR maturation, which occurs in the Golgi, or SREBP processing and nuclear localization that is dependent on COPII ER-to-Golgi trafficking[34], and Mdivi-1 did not significantly alter the secretion of the majority of HepG2 proteins identified by SILAC, DRP1 inhibition likely did not inhibit PCSK9 secretion by blocking conventional ER-to-Golgi trafficking. DRP1 localized to mitochondria, cytosol/cytosolic vesicles, and ER/ER exit sites in human liver cells. ER exit sites also serve a functional role in autophagy nucleation aside from COPII trafficking[40]. Cytosolic DRP1 at the ER-mitochondrial associated membranes can function in ER-associated mitochondrial division[13]. Beyond mitochondrial division the role of DRP1 at the ER is unclear, although DRP1 may have a functional role in ER maintenance in select tissues. In mouse β-cells DRP1 is an ER resident protein[41]. Overexpression of dominant negative DRP1 in β-cells does not alter ER morphology under control conditions, while DRP1 inhibition attenuates ER expansion induced by free fatty acid treatment[41]. As cytosolic DRP1 partially localizes to the ER and DRP1 inhibition impaired autophagic flux, along with PCSK9 being associated to the early secretory and protein degradation pathways, DRP1 inhibition may alter PCSK9 trafficking through ER and proteostasis regulation. DRP1 inhibition appeared to impair, but not fully inhibit autophagy in both human liver cells and mouse liver. Mdivi-1 increased BCL-XL in HepG2, thus without wishing to be bound by theory, can impair BECLIN1-dependent autophagy by BECLIN1 retention thus prohibiting BECLIN1 initiation of pre-autophagosome formation. DRP1 can bind with BCL-XL, and BCL-XL stimulates DRP1 activity[42], supporting a functional interaction with these proteins and raising the possibility of a compensatory response to inhibition. In addition to DRP1 membrane constriction activity, DRP1 can also function to tether membranes[43], raising the possibility that these functions may also be involved in DRP1 regulation of proteostasis. Mitochondria are a source of reactive oxygen species, which also act on cellular proteostasis[1]. No changes in mitochondrial membrane potential or cell viability were observed in HepG2 cells treated with Mdivi-1; however, whether additional mitochondrial alterations, related signaling molecules like calcium, or apoptosis-related pathways, including calpains and caspases participate in DRP1 inhibition-mediated changes in proteostasis requires further investigation.

In mice on a normal chow diet circulating cholesterol is largely in the form high-density lipoprotein, as such only a modest reduction in total cholesterol like that which was observed would be expected with the reduced PCSK9 secretion seen in Drp1LiKO mice. Drp1LiKO mice on normal chow diet had modest but significant increased liver LDLR and reduced serum LDL, despite a 78.5% reduction in circulating PCSK9. Similarly, mice that are heterozygous for PCSK9-deficiency have approximately 70% reduction in circulating PCSK9 with about a 1.3-fold increase in LDLR compared to about a 3.4-fold LDLR increase in homozygous PCSK9-defiencent mice[44]; therefore, even a small remaining fraction of circulating PCSK9 in mice on normal chow diet can majorly impact PCSK9-mediated LDLR degradation. On high-fat diet Drp1LiKO mice have reduced serum triglycerides and a reduction in total serum cholesterol about twice of that observed on a normal chow diet, along with reduced VLDL secretion[12]. There is emerging evidence of PCSK9 being involved in additional cardiovascular disease risk factors, independent of LDL regulation, including inflammation[3]. Mdivi-1 reduces oxidative stress and inflammation in diabetic apolipoprotein E-deficient mice[20], although the complete mechanisms of DRP1-mediated inflammation regulation remain to be fully elucidated.

Humans heterozygous for DRP1 deficiency, like heterozygous deletion mice, are viable and healthy, whereas homozygous DRP1 systemic-deficient mice have neurodevelopment defects and are embryonic lethal[28]. A small number of humans without any wild type DRP1, have been reported to survive postnatally with mutations in the dynamin 1-like gene that encodes the DRP1 protein, including dominant negative and complete loss of protein mutations that result in a range of pathologies from normal early development to distinct neuronal development issues[45,46]. In mice, cardiac DRP1 genetic deficiency results in heart failure[26,27], but pharmacologic DRP1 inhibition via Mdivi-1 reduces ischemia/reperfusion injury-induced myocardial infarction[47]. In humans lacking wild type DRP1, normal electrocardiogram and echocardiogram test results have been reported[46]. Worth mentioning is that lethality has been observed in systemic and liver specific[48] HMGCR (the target of statins) deficient mice, demonstrating key differences between pharmacologic inhibition and genetic deletion for cardiovascular therapy development.

Currently, Mdivi-1 is the only identified selective small molecule DRP1 inhibitor. A recent report[49] raised questions about the potency of Mdivi-1 in inhibiting mammalian DRP1; however, an independent report[31] using recombinant DRP1 confirmed the original findings[30] of mammalian DRP1 activity inhibition by Mdivi-1. In naïve wild type rodents, no abnormal phenotypes or cytotoxicity have been detected up to ten weeks after DRP1 inhibitor treatment, whether by Mdivi-1 injection, DRP1 inhibitor peptide, or by localized gene therapy[17]. Additionally, Drp1LiKO mice are viable, reducing but not eliminating concerns of targeting hepatic DRP1 as a therapeutic strategy. Therefore, targeting hepatic DRP1 may be a plausible approach to PCSK9 inhibition, in addition to providing cardiometabolic therapeutic benefit through additional means[18-21].

REFERENCES FOR EXAMPLES 1 & 2

1. Henning R H, Brundel B J J M. Proteostasis in cardiac health and disease. Nat Rev Cardiol; 2017: doi: 10.1038
2. Sun H, et al. Proprotein convertase subtilisin/kexin type 9 interacts with apolipoprotein B and prevents its intracellular degradation irrespective of the low-density lipoprotein receptor. Arterioscler Thromb Vasc Biol. 2012; 7:1585-1595.
3. Tang Z H, et al. New role of PCSK9 in atherosclerotic inflammation promotion involving the TLR4/NF-κB pathway. Atherosclerosis 2017; 262:113-122.
4. Abifadel M, et al. Mutations in PCSK9 cause autosomal dominant hypercholesterolemia. Nat Genet. 2003; 34:154-156.
5. Chapman M J et al.; PCSK9 Forum. PCSK9 inhibitors and cardiovascular disease: heralding a new therapeutic era. Curr Opin Lipidol. 2015; 26:511-520.
6. Park S W, Moon Y A, Horton J D. Post-transcriptional regulation of low density lipoprotein receptor protein by proprotein convertase subtilisin/kexin type 9a in mouse liver. J Biol Chem. 2004; 279:50630-50608.
7. Cohen J C, Hobbs H H. Genetics. Simple genetics for a complex disease. Science. 2013; 340:689-690.
8. Miyosawa K et al. New CETP inhibitor K-312 reduces PCSK9 expression: a potential effect on LDL cholesterol metabolism. Am J Physiol Endocrinol Metab. 2015; 309: 177-190.
9. Chen X W et al. SEC24A deficiency lowers plasma cholesterol through reduced PCSK9 secretion. Elife. 2013; 2:00444.
10. Ishihara N et al. Autophagosome requires specific early Sec proteins for its formation and NSF/SNARE for vacuolar fusion. Mol Biol Cell. 2001; 12:3690-3702.
11. Poirier S et al. GRP94 regulates circulating cholesterol levels through blockade of PCSK9-induced LDLR degradation. Cell Rep. 2015; 13:2064-2071.
12. Suntharalingam A et al. Glucose-regulated protein 94 triage of mutant myocilin through endoplasmic reticulum-associated degradation subverts a more efficient autophagic clearance mechanism. J Biol Chem. 2012; 287:40661-40669.
13. Friedman J R, Nunnari J. Mitochondrial form and function. Nature. 2014; 505:335-343.
14. Smirnova E, Griparic L, Shurland D L, van der Bliek A M. Dynamin-related protein Drp1 is required for mitochondrial division in mammalian cells. Mol Biol Cell. 2001; 12:2245-2256.
15. Jhen H F et al. Mitochondrial fission contributes to mitochondrial dysfunction and insulin resistance in skeletal muscle. Mol Cell Biol. 2012; 32:309-319.
16. Rehman J et al. Inhibition of mitochondrial fission prevents cell cycle progression in lung cancer. FASEB J. 2012; 26:2175-2186.
17. Bido S, Soria F N, Fan R Z, Bezard E, Tieu K. Mitochondrial division inhibitor-1 is neuroprotective in the A53T-α-synuclein rat model of Parkinson's disease. Sci Rep. 2017; 7:7495.
18. Lim S et al. Regulation of mitochondrial morphology by positive feedback interaction between PKCδ and Drp1 in vascular smooth muscle cell. J Cell Biochem. 2015; 116:648-660.
19. Wang L et al. Decreasing mitochondrial fission diminishes vascular smooth muscle cell migration and ameliorates intimal hyperplasia. Cardiovasc Res. 2015; 106:272-283.
20. Wang Q et al. Metformin suppresses diabetes-accelerated atherosclerosis via the inhibition of Drp1-mediated mitochondrial fission. Diabetes. 2017; 66:193-205.
21. Rogers M A et al. Dynamin-related protein 1 inhibition attenuates cardiovascular calcification in the presence of oxidative stress. Circ Res. 2017; 121:220-233.
22. Wang L et al. Disruption of mitochondrial fission in the liver protects mice from diet-induced obesity and metabolic deterioration. Diabetologia. 2015; 58:2371-2380.
23. Yoon Y, Pitts K R, Dahan S, McNiven M A. A novel dynamin-like protein associates with cytoplasmic vesicles and tubules of the endoplasmic reticulum in mammalian cells. J Cell Biol. 1998; 140:779-793.
24. Imoto M, Tachibana I, Urrutia R. Identification and functional characterization of a novel human protein highly related to the yeast dynamin-like GTPase Vps1p. J Cell Sci. 1998; 111:1341-1349.
25. Smirnova E et al. A human dynamin-related protein controls the distribution of mitochondria. J Cell Biol. 1998; 143:351-358.
26. Kageyama Y et al. Parkin-independent mitophagy requires Drp1 and maintains the integrity of mammalian heart and brain. EMBO J. 2014; 33:2798-2813.
27. Ikeda Y et al. Endogenous Drp1 mediates mitochondrial autophagy and protects the heart against energy stress. Circ Res. 2015; 116:264-278.
28. Ishihara N et al. Mitochondrial fission factor Drp1 is essential for embryonic development and synapse formation in mice. Nat Cell Biol. 2009; 11:958-966.
29. Macdonald P J, et al. Distinct splice variants of dynamin-related protein 1 differentially utilize mitochondrial fission factor as an effector of cooperative GTPase activity. J Biol Chem.

2016; 291:493-507.
30. Cassidy-Stone A, Chipuk J E, Ingerman E, Song C, Yoo C, Kuwana T, Kurth M J, Shaw J T, Hinshaw J E, Green D R, Nunnari J. Chemical inhibition of the mitochondrial division dynamin reveals its role in Bax/Bak-dependent mitochondrial outer membrane permeabilization. Dev Cell. 2008; 14:193-204.
31. Numadate A et al. Development of 2-thioxoquinazoline-4-one derivatives as dual and selective inhibitors of dynamin-related protein 1 (Drp1) and puromycin-sensitive aminopeptidase (PSA). Chem Pharm Bull (Tokyo). 2014; 62:979-988.
32. Ong S E, Mann M. Mass spectrometry-based proteomics turns quantitative. Nat Chem Biol. 2005; 1:252-262.
33. Koseoglu S et al. Dynamin-related protein-1 control fusion pore dynamics during platelet granule exocytosis. Arterioscler Thromb Vasc Biol. 2013; 33:481-488.
34. Nohturfft A et al. Regulated step in cholesterol feedback localized to budding of SCAP from E R membranes. Cell. 2000; 102:315-323.
35. Nozue T et al. Comparison of effects of pitavastatin versus pravastatin on serum proprotein convertase subtilisin/kexin type 9 levels in statin-naive patients with coronary artery disease. Am J Cardiol. 2013; 111:1415-1219.
36. Costet P et al. Hepatic PCSK9 expression is regulated by nutritional status via insulin and sterol regulatory element-binding protein 1c. J Biol Chem. 2006; 281:6211-6218.
37. Lee S et al. Berberine-induced LDLR up-regulation involves JNK pathway. Biochem Biophys Res Commun. 2007; 362:853-857.
38. Hogue A et al. Statin induces apoptosis and cell growth arrest in prostate cancer cells. Cancer Epidemiol Biomarkers Prev. 2008; 17:88-94.
39. Qian W et al. Mitochondrial hyperfusion induced by loss of the fission protein Drp1 causes ATM-dependent G2/M arrest and aneuploidy through DNA replication stress. J Cell Sci. 2012; 125:5745-5757.
40. Graef M et al. E R exit sites are physical and functional core autophagosome biogenesis components. Mol Biol Cell. 2013; 24:2918-2931.
41. Wikstrom J D et al. AMPK regulates E R morphology and function in stressed pancreatic β-cells via phosphorylation of DRP1. Mol Endocrinol. 2013; 27:1706-1723.
42. Li H et al. Bcl-xL induces Drp1-dependent synapse formation in cultured hippocampal neurons. Proc Natl Acad Sci USA. 2008; 105:2169-2174.
43. Ugarte-Uribe B et al. Dynamin-related protein 1 (Drp1) promotes structural intermediates of membrane division. J Biol Chem. 2014; 289:30645-30656.
44. Butkinaree C et al. J Biol Chem. 2015; 290:18609-18620.
45. Nasca A et al. Biallelic mutations in DNM1L are associated with a slowly progressive infantile encephalopathy. Hum Mutat. 2016; 37:898-903.
46. Sheffer R et al. Postnatal microcephaly and pain insensitivity due to a de novo heterozygous DMN1L mutation causing impaired mitochondrial fission and function. Am J Med Genet A. 2016; 170:1603-1607.
47. Ong S B et al. Inhibiting mitochondrial fission protects the heart against ischemia/reperfusion injury. Circulation. 2010; 121:2012-2022.
48. Nagashima S et al. Liver-specific deletion of the 3-hydroxy-3-methylglutaryl coenzyme A reductase causes hepatic steatosis and death. Arterioscler Thromb Vasc Biol. 2012; 32:1824-1831.
49. Bordt E A et al. Dev Cell. 2017; 40:583-594.
50. Rosdah A A et al. Mitochondrial fission—a drug target for cytoprotection or cytodestruction? Pharmacol Res Perspect. 2016; 4:e00235.

Methods & Materials

Reagents:

Pitavastatin and T0901317 were synthesized and provided by Kowa Company, Ltd. (Tokyo, Japan), and treated at a dose of 1 µM in all experiments. DMSO (vehicle; final concentration 0.01%) and Mdivi-1 (>99.85% purity) were purchased from Sigma (St. Louis, Mo.). Mdivi-1 in DMSO vehicle was added at a concentration of 50 µM in all experiments. Mdivi-1 in DMSO vehicle was added to cell culture media in a 50 mL tube, vortexed hard for several minutes and then incubated at 37° C. prior to adding to cells to ensure the compound was fully solubilized.

Human Cells:

HepG2 cells were obtained from ATCC (Manassas, Va.), and cultured in EMEM with L-glutamine (ATCC) medium, 1% pen/strep, with and without 10% FBS (Thermo Fisher Scientific, Waltham, Mass.) in 12-well plates (Corning, Durham, N.C.). HepG2 cells were plated at a density of 60-70% prior to treatment to avoid clumping. Freshly isolated primary human hepatocytes plated at 100% confluency on 12-well plates were obtained from Thermo Fisher Scientific. Three donors were used to obtain experimental data: 43-year-old Caucasian female, 23-year-old Caucasian female, and a 43-year-old Caucasian male. Primary hepatocytes were treated immediately upon arrival and cultured in William's E medium with hepatic maintenance supplement pack (Thermo Fisher Scientific), 1% pen/strep (VWR; Radnor, Pa.), and 10% FBS (Thermo Fisher Scientific). Cell viability was assessed by Trypan Blue exclusion using live/dead cell counting on a Countess™ II LT automated cell counter (Thermo Fisher Scientific).

Mouse Tissue:

Generation of Drp1LiKO and Flox/Flox control mice has been previously described.[22] Mice were fed ad libitum with a normal chow diet (5.4% fat, CRF-1; Orient Yeast, Tokyo, Japan), and housed under a 12 hour light-dark cycle in accordance with the Guide for the Care and Use of Laboratory Animals. All procedures were approved by the Ethics Committees on Animal Experimentation (Kyushu University, Graduate School of Medicine). Liver tissue and blood was isolated from one month old male Drp1LiKO (n=5) and Flox/Flox control (n=5) mice. All tissues were isolated under non-fasting conditions and at nine in the morning to avoid differences in diurnal regulation. Blood glucose was measured as previously described[22]. Liver and serum samples were shipped from Japan to the USA on dry ice and stored at −80° C. prior to processing. Serum total cholesterol was measured using the Wako™ total cholesterol E kit (Wako Chemicals, Japan), and serum triglycerides by the LabAssay™ triglyceride kit (Wako), both according to manufacturer's instructions. Lipoprotein distribution was determined by fast protein liquid chromatography. Lipoproteins were resolved from serum of individual mice (50 µl) by a Superose 6 column (HR 10/30) eluted with EDTA/NaCl/NaN3 (1 mmol/L; 0.154 mol/L; 0.02%) at a rate of 0.5 mL/min followed by fraction cholesterol analysis using the Wako kit.

Human Liver Tissue and Immunofluorescence Microscopy:

Liver from autopsies (n=4) were collected within 8-18 hours postmortem interval from Brigham and Women's Hospital according to IRB protocol #2013P002517/BWH. Cryo-preserved liver samples were cut into 7-µm thin slices, and fixed in acetone. After blocking in 4% serum, sections were incubated with primary antibody (human SEC31A, 1:20; ab86600, Abcam, Cambridge, Mass.), followed by anti-rabbit Alexa Fluor 488 antibody (1:200; Thermo Fisher Scientific). After avidin/biotin blocking (Vector Laboratories, Burlingame, Calif.), the second primary antibody (DRP1, 1:20; ab56788, Abcam, Cambridge, Mass.) was applied overnight at 4° C., followed by anti-mouse Alexa Fluor 594 antibody (Thermo Fisher Scientific). Sections were washed in PBS and embedded in mounting medium containing DAPI (Vector Laboratories).

HepG2 Cells and Immunofluorescence Microscopy:

HepG2 cells were grown on 0.1% gelatin coated Lab-Tek II chambered cover glass #1.5 borosilicate slides (Lab-Tek, Rochester, N.Y.), washed with PBS, fixed in 4% paraformaldehyde for 15 minutes, followed by permeabilization using 0.3% Triton X-100 for 5 minutes, washed, and then blocked with 1% BSA in PBS for 30 minutes. Filamentous actin was stained using CytoPainter Phallodin iFluor 555 Reagent (2 μl phalloidin in 2000 μl PBS with 1% BSA; Abcam), with a 60 minute incubation at room temperature. Slides were incubated with anti-alpha tubulin (1:200, Abcam, ab15246), PDI (1:100; 3501, Cell Signaling Technology), and anti-mitochondria (ab92824, Abcam) for 2 hours at room temperature or overnight at 4° C., followed by incubation with Alexa Fluor 488-labelled secondary antibody (1:200, Thermo Fisher Scientific). Nuclear staining was performed with DAPI (Thermo Fisher Scientific). Prior to visualization 200 μL PBS was added to each well. Liver tissue and cells were examined using a confocal microscope Al (Nikon Instruments Inc., Melville, N.Y.), and all images were processed with Elements 3.20 software (Nikon Instruments Inc.).

Mitochondrial Membrane Potential:

Mitochondrial membrane potential was assessed by TMRE reagent (Abcam) as previously described[21].

SILAC and Mass Spectrometry:

HepG2 cells were cultured on 100 mm dishes at a confluency of ~60-70%. Cells were cultured in either light labeled lysine or heavy labeled lysine containing SILAC media for about two weeks until heavy lysine was found to be >99% incorporated by mass spectrometry. Media was prepared with DMEM (no lysine, no arginine; A14431-01, Thermo Fisher Scientific) to which L-glutamine (2 mM, Lonza, Walkersville, Md.), L-arginine HCl (0.17 mM; Sigma), either light L-lysine HCl (0.339 mM; Sigma) or heavy L-lysine 2HCl (0.339 mM; Cambridge Isotopes, Tewksbury, Mass.), 10% dialyzed FBS (Thermo Fisher Scientific), 1% pen/strep was added. Media was changed every two days, and cells were split as required. At time of experiment, media was switched to SILAC DMEM without FBS, but with the addition of either Mdivi-1 (50 μM) or vehicle (0.01% DMSO). After 24 hours incubation, 9 mL heavy labeled media with vehicle was collected and pooled with 9 mL light media with Mdivi-1. Similarly, 9 mL heavy labeled media with Mdivi-1 was pooled with 9 mL light media with vehicle. Media was concentrated in Vivaspin™ 20 Concentrator 5,000 MWCO columns (GE Healthcare, Little Chalfont, UK) according to manufacturer's instructions. 100 μg samples were lysed and proteolysed (1 μg trypsin/100 μg protein; Promega, Madison, Wis. or 0.5 μg Lys-C/100 ug protein) using the in-solution urea+RapiGest™ (Waters). Peptides were desalted using Oasis Hlb 1 cc (10 mg) columns (Waters, Milford, Mass.) and then dried using a tabletop speed vacuum (Thermo Fisher Scientific) and resuspended in 40 μL of 5% acetonitrile (Thermo Fisher Scientific), 5% formic acid (Sigma) for subsequent analysis by liquid chromatography/mass spectrometry (LC/MS).

The peptide sample was diluted [1/10-fold] and analyzed with the high resolution/accuracy Q Exactive™ mass spectrometer fronted with a Nanospray™ FLEX ion source, and coupled to an Easy-nLC1000 HPLC pump (Thermo Fisher Scientific). The peptides were subjected to a dual column set-up: an Acclaim PepMap™ RSLC C18 trap column, 75 mm×20 mm; and an Acclaim PepMap™ RSLC C18 analytical column 75 mm×250 mm (Thermo Fisher Scientific). The analytical gradient was run at 300 nl/min from 5 to 18% Solvent B (acetonitrile/0.1% formic acid) for 130 minutes, continuously 18 to 28% for 35 minutes, 28 to 65% for 10 minutes followed by 5 minutes of 95% Solvent B. Solvent A was 0.1% formic acid. All reagents were HPLC-grade. The instrument was set to 140 K resolution, and the top 10 precursor ions (within a scan range of 380-2000 m/z) were subjected to higher energy collision induced dissociation (HCD, collision energy 25% (+/−10%), isolation width 1.6 m/z, dynamic exclusion enabled (20s), and resolution set to 17.5 K). The MS/MS data were queried against the Human UniProt™ database (downloaded on Aug. 1, 2014) using the HT-SEQUEST™ search algorithm, via the Proteome Discoverer™ Package (version 1.4, Thermo Scientific), using a 10 ppm tolerance window in the MS1 search space, and a 0.02 Da fragment tolerance window for HCD. Methionine oxidation was set as a variable modification, and carbamidomethylation of cysteine residues were set as fixed modifications. The peptide false discovery rate (FDR) was calculated using Percolator™ provided by Proteome Discoverer. Peptides were filtered based on a 1% FDR. Quantification of SILAC peak pairs was also done in Proteome Discoverer™ using up to the top three most abundant peptides. To ensure proper identification and reproducibility, proteins that had reduced secretion following Mdivi-1 treatment were identified by having two or more unique peptides and observed in at least three experiments including at least once in both light and heavy labeled cells treated with Mdivi-1. Significant changes were determined as proteins with an average value (ratio of Mdivi-1 treated/vehicle treated peak intensity) plus two standard deviations being less than the control value (vehicle treated/vehicle treated peak intensity=1).

PCSK9 ELISA:

Mouse serum PCSK9 was measured using the mouse proprotein convertase 9/PCSK9 quantikine ELISA kit (MPC900, R&D Systems, Minneapolis, Minn.), and human liver cell secreted PCSK9 using the human proprotein convertase 9/PCSK9 DuoSet ELISA (DY3888, R&D Systems), both according to manufacturers' protocols.

CRISPR/Cas9 Gene Editing:

HepG2 cells were plated at 60-70% confluency on 150 mm plates (Corning) in EMEM with 10% FBS without pen/strep. The following day cells were detached by 0.25% trypsin-EDTA solution (ATCC), and transfected while still in suspension using the Lipofectamine™ 3000 reagent (Thermo Fisher Scientific) according to manufacturer's protocol. Cells were co-transfected with human DRP1 CRISPR/Cas9 KO plasmid (sc-400459, Santa Cruz, Dallas, Tex.) and human DRP1 HDR plasmid (sc-400459-HDR, Santa Cruz). Control cells were transfected with control CRISPR/Cas9 plasmid (sc-41-8922, Santa Cruz). Cells were incubated for 72 hours at 37° C., changing media after 48 hours. GFP and RFP fluorescence was examined by confocal microscopy. Cells were then sorted to isolate GFP-positive cells by FACS using a BDFACS Aria™ II cell sorter (BD Biosciences;

Franklin Lakes, N.J.). GFP-positive cells were plated and KO plasmid cells were further selected by puromycin selection (2 μg/mL in EMEM with 10% FBS for five days, changing the medium every two days). Cells were then plated to obtain colonies that were assessed for DRP1 gene editing by Western blot analysis.

RNA Extraction and Real Time PCR:

Human cells and mouse liver was homogenized with TriZol™ (Life Technologies, Grand Island, N.Y.) to isolate RNA. QuantiTect™ Reverse Transcription Kit (Qiagen, Hilden, Germany) was used for reverse transcription on total RNA. cDNA was generated using the Quanta gScript™ cDNA Synthesis Kit (Bioscience Inc., Gaithersburg, Md.). mRNA levels were quantified on a 7900HT real-time PCR system (Thermo Fisher Scientific) using TaqMan™ real-time PCR with the following probes: Hs02758991_g1 (human GAPDH); Mm99999915_g1 (mouse Gapdh); Hs00236329 m1 (human BCL2L1); Hs00247147_m1 (human DRP1); Hs00545399_m1 (human PCSK9); Mm01263610_m1 (mouse Pcsk9); Hs00168352_m1 (human HMGCR); Mm01282499_m1 (mouse Hmgcr); Hs00181192_m1 (human LDLR); Mm00440169_m1 (mouse Ldlr); Hs01088691_m1 (human SREBP1); Mm00550338_m1 (mouse Srebp1); Hs00231674_m1 (human SREBP1a); custom primer (human SREBP1c); Hs01081784_m1 (human SREBP2); Mm01306292_m1 (mouse Srebp2); Hs01005622_m1 (human FASN); Mm00662319_m1 (mouse Fasn); Hs00167041_m1 (human HNF1A); Mm00493434_m1 (mouse Hnf1a); Hs00171168 (human APOE); Hs01059118_m1 (human ABCA1); Hs01103582_s1 (human JUN). Mouse SREBP-1c was analyzed by SYBER™ green PCR with the following primers: F-GGAGCCATGGATTGCACATT; R-GGCCCGG-GAAGTCACTGT. All expression levels were normalized to GAPDH using the ΔΔCT method.

Protein Extraction and Western Blotting:

S9 fraction from human liver (n=50 pooled donors) was obtained from Thermo Fisher. Native PCSK9 overexpression lysate and control HEK293 lysate was obtained from Novus. HeLa PCSK9 CRISPR knockout and control lysate was obtained from Origene. THP1 lysate was isolated from cells obtained from ATCC. LDLR-deficient (#002207) and control (#000664) mice were obtained from Jackson lab, and liver tissue was collected for Western blot antibody controls. Overexpressed murine PCSK9 liver tissue lysate was obtained from mice injected with PCSK9 gain-of-function adeno-associated virus as previously described[21]. Human cells and mouse liver was homogenized in ice cold RIPA buffer (Thermo Fisher Scientific) containing 1X Halt combined protease and phosphatase inhibitor cocktails (Thermo Fisher Scientific) for whole cell/tissue lysate. Nuclear protein lysates were isolated from mouse liver tissues using the NE-PER nuclear isolation kit (Thermo Fisher Scientific) according to manufacturer's protocol. Protein concentrations were determined by the Pierce BCA Assay™ (Thermo Fisher Scientific). Protein lysate was loaded onto 4-15% gels (Bio-Rad, Hercules, Calif.) in SDS loading buffer (Boston BioProducts, Ashland, Mass.). Gels were transferred onto iBlot™ Nitrocellulose membranes (Thermo Fisher Scientific), incubated with primary and secondary antibodies, and imaged on an ImageQuant™ LA54000 (GE Healthcare). Primary antibodies used for Western blot analysis included: β-actin (1:5,000, NB600-501, Novus, Littleton, Colo.); α-TUBULIN (1:1000, ab15246, Abcam); DRP1 (1:1,000, ab56788, Abcam); PCSK9 used for human cells (BAF3888, R&D Systems) and mouse liver (AF3985, R&D Systems); PCSK9 used for human cells only (1:1000, ab28770, Abcam); LDLR (1:1000, 3839-100, BioVision Inc, Milpitas, Calif.); SREBP2 (1:1000, ab30682, Abcam); SREBP1(1:500, ab3259, Abcam); LAMIN A/C (1:1000, 39288, Activ Motif, Carlsbad, Calif.); FASN (1:200, sc-55580, Santa Cruz); HMGCR (1:1000, ab174830, Abcam); c-Jun (1:1000, 9165S, Cell Signaling Technology, Danvers, Mass.); p (S73) c-Jun (1:1000, 3270s, Cell Signaling Technology); p (S616) DRP1 (1:1000, 3455s, Cell Signaling); p (S637) DRP1 (1:1000, 4867s, Cell Signaling); BIP (1:1000, 3177P, Cell Signaling Technology); CHOP (1:1000, 2895P, Cell Signaling Technology™); HNF1a (1:200, sc-6547, Santa Cruz); BCL-2 (1:200, sc-7382, Santa Cruz; 1:1000, 4223S, Cell Signaling Technology); BCL-XL (1:1000, 2764S, Cell Signaling Technology); p62 (1:1000, 5114S, Cell Signaling Technology); p (S349) p62 (1:1000, 95697S, Cell Signaling Technology); LC3 (1:1000, NB100-222, Novus). Protein levels were normalized to β-ACTIN, α-TUBULIN, or LAMIN A/C with the use of NIH ImageJ software for quantification.

Endo H Assay:

Endo H assay was performed as described in (14) with some minor modifications. Briefly 20 μg of whole mouse liver lysate in RIPA buffer was incubated with or without 10 milliunits Endo H enzyme (New England Biolabs™, Ipswich, Mass.) overnight at 37° C., followed by heating samples for 20 minutes at 70° C., and western blot analysis was performed. Endo H resistance was quantified as the ratio of Endo H resistant PCSK9 of total PCSK9 (Endo resistant+sensitive PCSK9) using NIH ImageJ software.

Electron Microscopy:

HepG2 cells were grown at a density of about 60-70% on 150 mm plates. Medium was decanted and room temperature fixative added directly to the plate to cover the cells. For ER morphology cells were fixed with 2% glutaraldehyde in 0.1M sodium cacodylate buffer; for immune-EM, cells were fixed in 4.0% paraformaldehyde with 0.2% glutaraldehyde in 0.1M sodium cacodylate buffer (fixatives and EM wash buffer were freshly prepared and provided by the Mass General PMB microscopy core). Cells were fixed for 2 hours at room temperature. Fixative was decanted, and cells were rinsed three times with 0.1M sodium cacodylate buffer. Cells were gently scraped with a polyethylene cell lifter (Corning) and transferred into 15 mL centrifuge tubes (Corning). Dishes were rinsed with 2 mL 0.1M sodium cacodylate buffer and the wash was added to the 15 mL tubes. Cell suspensions were spun down at 2,000 rpm for 10 minutes in a 4° C. centrifuge. Supernatant was removed and 2 mL 0.1M sodium cacodylate buffer was added to the tubes without disturbing the pullet. Pelleted samples were stored at 4° C. and submitted to the Mass General PMB microscopy core for EM processing as ultracyrosections. DRP1 immunogold labeling was performed using DRP1 antibody (1:100, ab56788, Abcam).

Network Analysis:

Network representation of pathway enrichment was generated from the SILAC dataset. Node size was made proportional to the significance of enrichment measured in units of −log(q-value), where the q-value was calculated by testing for over-representation by a hypergeometric test and adjusting for multiple comparisons using the Benjamini-Hochberg method for controlling false discovery rate (FDR). Edge thickness was made proportional to the number of overlapping proteins between the two connected pathways in units of the Jaccard index, which is defined as $$J = \frac{s_A \cap s_B}{s_A \cup s_B}$$

where $s_A$ and $s_B$ are the set of proteins detected in proteomics that belong to pathway A and pathway B, respectively. Edges with a Jaccard index <0.1 were discarded in the visualization for clarity. For the pathway enrichment analysis, the canonical pathways from KEGG, Biocarta and Reactome were considered.

Statistical Analysis:

PRISM software (GraphPad, San Diego, Calif.) was used to analyze data with t-test or ANOVA with post hoc test where appropriate. SILAC mass spectrometry data analysis was performed using a 1-sample t-test to assess how significant each protein's ratio was from 1 (the ideal ratio if there is no effect of Mdivi-1 treatment), the p-value was then adjusted using Benjamini and Hochberg method (FDR), and the results visualized using a volcano plot.

The references cited herein and throughout the specification are incorporated herein by reference.

The invention claimed is:

1. A method for reducing blood cholesterol levels in a subject, the method comprising:
   administering an effective amount of an inhibitor of dynamin-related protein 1 (DRP1); or
   administering an effective amount of a composition comprising an inhibitor of DRP1 to a human or non-human subject in need thereof,
   wherein the inhibitor of DRP1 is a nucleic acid,
   and wherein the nucleic acid is selected from the group consisting of: a DRP1 specific RNA interference agent, a vector encoding a DRP1-specific RNA interference agent, and an aptamer that binds DRP1.

2. The method of claim 1, wherein the DRP1-specific RNA interference agent is targeted for delivery to the liver.

3. The method of claim 1, wherein the DRP1 inhibitor is administered with a pharmaceutically acceptable carrier.

4. The method of claim 1, wherein the DRP1 inhibitor is administered with at least one additional cholesterol lowering agent.

5. The method of claim 4, wherein the at least one additional cholesterol lowering agent is selected from the group consisting of: statin, 7-alpha hydroxylase, liver X receptor agonist, bile acid binding resins, cholesterol absorption inhibitors, fibrates, niacin, omega-3 fatty acids, and pterostilbene.

6. The method of claim 1, wherein the DRP1 inhibitor causes a reduction of low density lipoprotein in the subject.

7. The method of claim 1, wherein the DRP1 inhibitor causes a reduction of serum proprotein convertase subtilisin/kexin type 9 (PCSK9) in the subject.

8. The method of claim 1, wherein the DRP1 inhibitor causes a reduction of PCSK9 mRNA in cells of the subject.

9. The method of claim 1, wherein the subject has a high level of cholesterol or a high level of low density lipoprotein.

10. The method of claim 1, wherein the subject has exhibited intolerance to conventional statin therapy.

11. A method for decreasing proprotein convertase subtilisin/kexin type 9 (PCSK9) serum levels in a mammal in need thereof, the method comprising:
    administering a pharmaceutical composition comprising:
      an effective amount of an inhibitor of dynamin-related protein 1 (DRP1), and a pharmaceutically acceptable carrier to a mammal in need thereof,
    whereby the level of PCSK9 expression and/or secretion is decreased in said mammal, relative to the level of PCSK9 expression and/or secretion prior to said administering.

12. The method of claim 11, wherein the inhibitor of dynamin-related protein 1 (DRP1) increases the level of LDLR expression in a cell of the mammal relative to the level of LDLR expression in a cell of a mammal that was not administered the DRP1 inhibitor.

13. The method of claim 11, wherein the inhibitor of DRP1 is a small molecule or a nucleic acid.

14. The method of claim 11, wherein the small molecule is selected from the group consisting of: Mdivi-1, P110; 3-Hydroxynaphthalene-2-carboxylic acid-(3,4-dihydroxybenzylidene)-hydrazide; and 3-Hydroxynaphthalene-2-carboxylic acid (3,4-dihydroxybenzylidene)hydrazide.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggaggcgcta attcctgtca t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gcaactggtc catgtttcac a                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gctgctcagt atcagtctct t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gaatctgctc atgtggagac t                                              21

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5
```

```
Leu Val Phe Ala Gln
1               5

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(21)
<223> OTHER INFORMATION: a, c, t, g, unknown or other

<400> SEQUENCE: 6
aannnnnnnn nnnnnnnnnn ntt                                           23

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggagccatgg attgcacatt                                               20

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggcccgggaa gtcactgt                                                 18
```